US012629197B2

(12) United States Patent
Scott et al.

(10) Patent No.: US 12,629,197 B2
(45) Date of Patent: May 19, 2026

(54) ELECTROSURGICAL DEVICE

(71) Applicant: Palladium Medical LLC, Lake Elmo, MN (US)

(72) Inventors: Paul Daniel Scott, Lake Elmo, MN (US); Evan Charles Tornell, Edina, MN (US); Daniel A. Friedrichs, Mendota Heights, MN (US); Rachael L. Rich, Blaine, MN (US); Rachel J. Anderson, Minneapolis, MN (US); Lori E. Lucke, Rosemount, MN (US); Timothy L. Clarke, Stillwater, MN (US); Parker J. Blezek, Minneapolis, MN (US); Sarah J. Blair, Bloomington, MN (US)

(73) Assignee: Palladium Medical, LLC, Lake Elmo, MN (US)

( * ) Notice: Subject to any disclaimer, the term of this patent is extended or adjusted under 35 U.S.C. 154(b) by 879 days.

(21) Appl. No.: 17/747,970

(22) Filed: May 18, 2022

(65) Prior Publication Data

US 2022/0370116 A1     Nov. 24, 2022

Related U.S. Application Data

(60) Provisional application No. 63/190,423, filed on May 19, 2021.

(51) Int. Cl.
*A61B 18/14* (2006.01)
*A61B 18/00* (2006.01)

(52) U.S. Cl.
CPC .... *A61B 18/14* (2013.01); *A61B 2018/00059* (2013.01); *A61B 2018/00589* (2013.01);
(Continued)

(58) Field of Classification Search
CPC ........... A61B 2018/00589; A61B 2018/00601; A61B 2018/00607; A61B 18/14; A61B 2018/1475
See application file for complete search history.

(56) References Cited

U.S. PATENT DOCUMENTS

| | | | |
|---|---|---|---|
| 4,307,720 A | 12/1981 | Weber | |
| 4,907,599 A | 3/1990 | Taylor | |
| (Continued) | | | |

FOREIGN PATENT DOCUMENTS

| | | |
|---|---|---|
| CN | 110099528 A | 8/2019 |
| CN | 211911793 U | 11/2020 |
| (Continued) | | |

OTHER PUBLICATIONS

International Search Report and Written Opinion dated Sep. 19, 2022 for International Application No. PCT/US2022/029923.

*Primary Examiner* — Bradford C. Blaise
(74) *Attorney, Agent, or Firm* — Seager, Tufte & Wickhem, LLP

(57) ABSTRACT

Example electrosurgical devices and systems are disclosed. An example electrosurgical device includes a body, an electrosurgical electrode secured to the body, the electrosurgical electrode including a distal tip. The electrosurgical device also includes a shroud translatable relative to the electrosurgical electrode between a first position and a second position, a first magnetic component which is operably connected to the body, and a second magnetic component which is operably connected to the shroud, wherein the first and second magnetic components magnetically interact to releasably maintain the shroud in the first position.

16 Claims, 38 Drawing Sheets

(52) U.S. Cl.
    CPC ............... *A61B 2018/00601* (2013.01); *A61B 2018/00607* (2013.01); *A61B 2018/1475* (2013.01)

(56) References Cited

U.S. PATENT DOCUMENTS

| | | | |
|---|---|---|---|
| 4,919,129 A | | 4/1990 | Weber, Jr. et al. |
| 5,035,695 A | | 7/1991 | Weber, Jr. et al. |
| 5,234,428 A | | 8/1993 | Kaufman |
| 5,350,355 A | | 9/1994 | Sklar |
| 5,380,321 A | | 1/1995 | Yoon |
| 5,496,314 A | * | 3/1996 | Eggers ................. A61B 18/082 606/29 |
| 5,674,219 A | | 10/1997 | Monson et al. |
| 5,712,543 A | | 1/1998 | Sjostrom |
| 6,500,169 B1 | | 12/2002 | Deng |
| 6,524,307 B1 | | 2/2003 | Palmerton et al. |
| 6,616,658 B2 | | 9/2003 | Ineson |
| 6,986,768 B2 | | 1/2006 | Allen et al. |
| 7,060,064 B2 | | 6/2006 | Allen et al. |
| 7,156,842 B2 | | 1/2007 | Sartor et al. |
| 7,156,844 B2 | | 1/2007 | Reschke et al. |
| 7,198,625 B1 | | 4/2007 | Hui et al. |
| 7,244,257 B2 | | 7/2007 | Podhajsky et al. |
| 7,291,145 B2 | | 11/2007 | Seid |
| 7,296,571 B2 | | 11/2007 | Foltz et al. |
| 7,500,974 B2 | | 3/2009 | Sartor |
| 7,503,917 B2 | | 3/2009 | Sartor et al. |
| 7,582,244 B2 | | 9/2009 | Allen et al. |
| 7,879,033 B2 | | 2/2011 | Sartor et al. |
| 7,959,633 B2 | | 6/2011 | Sartor et al. |
| 8,016,824 B2 | | 9/2011 | Buchman, II et al. |
| 8,057,470 B2 | | 11/2011 | Lee et al. |
| 8,100,902 B2 | | 1/2012 | Sartor |
| 8,128,622 B2 | | 3/2012 | Podhajsky et al. |
| 8,133,223 B2 | | 3/2012 | Docimo |
| 8,211,103 B2 | | 7/2012 | Greep |
| 8,235,987 B2 | | 8/2012 | Craig |
| 8,287,534 B2 | | 10/2012 | Balog |
| 8,449,540 B2 | | 5/2013 | Sartor et al. |
| 8,460,289 B2 | | 6/2013 | Sartor |
| 8,506,565 B2 | | 8/2013 | Decarlo |
| 8,518,018 B2 | | 8/2013 | Minskoff et al. |
| 8,591,509 B2 | | 11/2013 | Fry et al. |
| 8,597,292 B2 | | 12/2013 | Kerr |
| 8,608,732 B2 | | 12/2013 | Seid |
| 8,632,536 B2 | | 1/2014 | Kerr et al. |
| 8,636,733 B2 | | 1/2014 | Heard |
| 8,663,218 B2 | | 3/2014 | Heard et al. |
| 8,663,219 B2 | | 3/2014 | Heard et al. |
| 8,690,872 B2 | | 4/2014 | Jayaraj |
| 8,721,638 B2 | | 5/2014 | Deutscher et al. |
| 8,784,416 B2 | | 7/2014 | Balog |
| 8,845,616 B2 | | 9/2014 | Minskoff et al. |
| 8,845,634 B2 | | 9/2014 | Deutscher et al. |
| 8,858,550 B2 | | 10/2014 | Busch-Madsen et al. |
| 8,858,554 B2 | | 10/2014 | Kerr et al. |
| 8,882,767 B2 | | 11/2014 | Greep et al. |
| 8,882,768 B2 | | 11/2014 | Greep et al. |
| 8,932,286 B2 | | 1/2015 | Terry et al. |
| 8,932,292 B2 | | 1/2015 | Terry et al. |
| 8,945,124 B2 | | 2/2015 | Craig |
| 9,138,289 B2 | | 9/2015 | Conley et al. |
| 9,198,720 B2 | | 12/2015 | Heard et al. |
| 9,216,051 B2 | | 12/2015 | Fischer et al. |
| 9,259,260 B2 | | 2/2016 | Greep et al. |
| 9,289,261 B2 | | 3/2016 | Shvetsov et al. |
| 9,345,535 B2 | | 5/2016 | Kerr et al. |
| 9,370,394 B2 | | 6/2016 | Jayaraj |
| 9,375,252 B2 | | 6/2016 | Coe et al. |
| 9,375,253 B2 | | 6/2016 | Greep et al. |
| 9,474,572 B2 | | 10/2016 | Lowry |
| 9,486,562 B2 | | 11/2016 | Minskoff et al. |
| 9,763,729 B2 | | 9/2017 | Minskoff et al. |
| 9,808,306 B2 | | 11/2017 | Balog |
| 9,867,653 B2 | | 1/2018 | Minskoff et al. |
| 9,877,773 B2 | | 1/2018 | Minskoff et al. |
| 9,877,774 B2 | | 1/2018 | Minskoff et al. |
| 9,895,191 B2 | | 2/2018 | Conley et al. |
| 9,901,391 B2 | | 2/2018 | Busch-Madsen et al. |
| 9,907,621 B2 | | 3/2018 | Jayaraj |
| 9,987,074 B2 | | 6/2018 | Ineson |
| 10,022,479 B2 | | 7/2018 | Minskoff et al. |
| 10,034,970 B2 | | 7/2018 | Minskoff et al. |
| 10,085,794 B2 | | 10/2018 | Kerr et al. |
| 10,105,917 B2 | | 10/2018 | Schlegelmilch |
| 10,143,831 B2 | | 12/2018 | Juergens et al. |
| 10,149,715 B2 | | 12/2018 | Busch-Madsen et al. |
| 10,405,917 B2 | | 9/2019 | Shvetsov et al. |
| 10,478,244 B2 | | 11/2019 | Busch-Madsen et al. |
| 10,561,459 B2 | | 2/2020 | Fleenor |
| 10,595,934 B2 | | 3/2020 | Cosmescu |
| 10,631,917 B2 | | 4/2020 | Ineson |
| 10,631,923 B2 | | 4/2020 | Ineson |
| 10,675,084 B2 | | 6/2020 | Lowry |
| 10,695,120 B2 | | 6/2020 | Hagg |
| 2005/0017526 A1 | | 1/2005 | Arrotta |
| 2005/0080408 A1 | | 4/2005 | Seid |
| 2006/0058784 A1 | | 3/2006 | Gedebou |
| 2006/0069387 A1 | | 3/2006 | Gedebou |
| 2007/0112343 A1 | | 5/2007 | Mische et al. |
| 2008/0033427 A1 | | 2/2008 | Seid |
| 2008/0319441 A1 | | 12/2008 | Seid |
| 2009/0024125 A1 | | 1/2009 | Docimo |
| 2009/0062791 A1 | * | 3/2009 | Lee .................... A61B 18/1402 606/45 |
| 2011/0098600 A1 | * | 4/2011 | Matsumura ...... A61B 5/150022 600/583 |
| 2011/0301602 A1 | * | 12/2011 | Roy ....................... A61B 17/29 606/205 |
| 2014/0081086 A1 | | 3/2014 | Shvetsov et al. |
| 2015/0141983 A1 | | 5/2015 | Jadhav et al. |
| 2015/0335376 A1 | | 11/2015 | Hufnagel et al. |
| 2016/0135868 A1 | * | 5/2016 | Joseph ............... A61B 18/1445 606/34 |
| 2016/0228176 A1 | | 8/2016 | Colquhoun |
| 2016/0346029 A1 | | 12/2016 | Colquhoun |
| 2017/0020599 A1 | | 1/2017 | Brooke |
| 2017/0303989 A1 | | 10/2017 | Kirwan, Jr. |
| 2017/0360499 A1 | | 12/2017 | Greep et al. |
| 2018/0028255 A1 | | 2/2018 | Miller et al. |
| 2018/0036064 A1 | | 2/2018 | Shvetsov et al. |
| 2018/0036068 A1 | | 2/2018 | Miller et al. |
| 2018/0153610 A1 | | 6/2018 | Minskoff et al. |
| 2018/0153635 A1 | | 6/2018 | Preissman |
| 2018/0228530 A1 | | 8/2018 | Yates et al. |
| 2018/0243025 A1 | | 8/2018 | Smits et al. |
| 2018/0250060 A1 | | 9/2018 | Mandavia et al. |
| 2018/0271585 A1 | | 9/2018 | Ineson |
| 2018/0333201 A1 | | 11/2018 | Greep et al. |
| 2019/0021782 A1 | | 1/2019 | Segit et al. |
| 2019/0269452 A1 | | 9/2019 | Cosmescu |
| 2020/0054381 A1 | | 2/2020 | Kao |
| 2020/0054383 A1 | | 2/2020 | Kao |
| 2020/0093535 A1 | | 3/2020 | Manley et al. |
| 2020/0197074 A1 | | 6/2020 | Brooke |
| 2020/0229839 A1 | * | 7/2020 | Lai .................... A61B 17/3421 |
| 2020/0237428 A1 | | 7/2020 | Fleenor |
| 2022/0104803 A1 | * | 4/2022 | Desjardin .......... A61B 17/0483 |

FOREIGN PATENT DOCUMENTS

| | | |
|---|---|---|
| EP | 3265007 A1 | 1/2018 |
| WO | 2020106993 A1 | 5/2020 |

* cited by examiner

ELECTROSURGICAL DEVICE

TECHNICAL FIELD

The present disclosure pertains to medical devices, and methods for manufacturing medical devices. More particularly, the present disclosure pertains to electrosurgical medical devices including electrosurgical devices having electrically conductive electrodes for cutting or coagulating tissue.

BACKGROUND

During a medical surgery, a surgeon may use an electrosurgical device to cauterize, coagulate and/or cut tissue. For example, coagulating blood vessels is a necessary part of a medical surgery and is commonly performed by an electrosurgical device known as an electrosurgical pen. An electrosurgical pen may include an electrically conductive metal electrode which extends outwardly from the end of a hollow main body, whereby the main body acts as a hand grip for the surgeon during surgery.

When the electrosurgical electrode touches or is near the tissue at a surgical site, a high frequency electrical current flows from the electrode to the tissue, thus cutting and/or coagulating the tissue. However, when the pen is activated (or remains activated after cutting or coagulating tissue or has been recently activated) the intense heat generated at the electrically conductive electrode tip has the potential to cause fires (e.g., if the electrode tip contacts flammable materials). Furthermore, if the heated electrode does not cause a fire, it has the potential to cause burns to users with whom the heated electrode makes unintended contact. Therefore, in some instances it may be desirable to design an electrosurgical pen which includes an actuatable shroud which shields the electrode tip from undesirable contact with flammable materials, clinicians, patients, etc. Example electrosurgical devices having actuatable, protective shrouds are disclosed herein.

BRIEF SUMMARY

This disclosure provides design, material, manufacturing method, and use alternatives for medical devices. An example electrosurgical device includes a body, an electrosurgical electrode secured to the body, the electrosurgical electrode including a distal tip. The electrosurgical device also includes a shroud translatable relative to the electrosurgical electrode between a first position and a second position, a first magnetic component which is operably connected to the body, and a second magnetic component which is operably connected to the shroud, wherein the first and second magnetic components magnetically interact to releasably maintain the shroud in the first position.

Alternatively or additionally to any of the embodiments above, wherein the first magnetic component is selected from one or more of a permanent magnet, a magnetic material, and an electromagnet.

Alternatively or additionally to any of the embodiments above, wherein the second magnetic component is selected from one or more of a permanent magnet, a magnetic material, and an electromagnet.

Alternatively or additionally to any of the embodiments above, wherein at least one of the first magnetic component and the second magnetic component includes a permanent magnet.

Alternatively or additionally to any of the embodiments above, wherein at least one of the first magnetic component and the second magnetic component includes a magnetic material.

Alternatively or additionally to any of the embodiments above, wherein at least one of the first magnetic component and the second magnetic component includes an electromagnet.

Alternatively or additionally to any of the embodiments above, wherein the electromagnet includes a core of magnetic material surrounded by a coil through which an electric current is passed to magnetize the core, wherein the core and coil are positionally fixed relative to one another.

Alternatively or additionally to any of the embodiments above, wherein the first magnetic component includes a first permanent magnet and the second magnetic component includes a second permanent magnet.

Alternatively or additionally to any of the embodiments above, wherein the first magnetic component includes a permanent magnet and the second magnetic component includes a magnetic material.

Alternatively or additionally to any of the embodiments above, wherein the first magnetic component includes a magnetic material and the second magnetic component includes a permanent magnet.

Alternatively or additionally to any of the embodiments above, wherein the first magnetic component includes an electromagnet and the second magnetic component includes a permanent magnet.

Alternatively or additionally to any of the embodiments above, wherein the first magnetic component includes an electromagnet and the second magnetic component includes a magnetic material.

Alternatively or additionally to any of the embodiments above, wherein the first magnetic component includes a permanent magnet and the second magnetic component includes an electro-magnet.

Alternatively or additionally to any of the embodiments above, wherein the first magnetic component includes a magnetic material and the second magnetic component includes an electromagnet.

Alternatively or additionally to any of the embodiments above, wherein the electromagnet includes a core of magnetic material surrounded by a coil through which an electric current is passed to magnetize the core, wherein the core and coil are positionally fixed relative to one another.

Alternatively or additionally to any of the embodiments above, wherein when the shroud is in the first position, the distal tip of the electrosurgical electrode is disposed within the shroud.

Alternatively or additionally to any of the embodiments above, wherein when the shroud is in the second position, the distal tip of the electrosurgical electrode is exposed distally of the shroud.

Alternatively or additionally to any of the embodiments above, wherein when the shroud is in the first position, the distal tip of the electrosurgical electrode is exposed distally of the shroud.

Alternatively or additionally to any of the embodiments above, wherein when the shroud is in the second position, the distal tip of the electrosurgical electrode is disposed within the shroud.

Alternatively or additionally to any of the embodiments above, further including a third magnetic component operably connected to the body.

Alternatively or additionally to any of the embodiments above, wherein the second and third magnetic components magnetically interact to releasably maintain the shroud in the second position.

Alternatively or additionally to any of the embodiments above, wherein the second magnetic component is disposed between the first and the third magnetic components.

Alternatively or additionally to any of the embodiments above, wherein the third magnetic component is selected from one or more of a permanent magnet, a magnetic material, and an electromagnet.

Alternatively or additionally to any of the embodiments above, wherein the first magnetic component includes a first permanent magnet, the second magnetic component includes a second permanent magnet, and the third magnetic component includes a third permanent magnet.

Alternatively or additionally to any of the embodiments above, wherein the first magnetic component includes a first permanent magnet, the second magnetic component includes magnetic material, and the third magnetic component includes a second permanent magnet.

Alternatively or additionally to any of the embodiments above, wherein the first magnetic component includes a first permanent magnet, the second magnetic component includes a second permanent magnet, and the third magnetic component includes magnetic material.

Alternatively or additionally to any of the embodiments above, wherein the first magnetic component includes magnetic material, the second magnetic component includes a first permanent magnet, and the third magnetic component includes a second permanent magnet.

Alternatively or additionally to any of the embodiments above, wherein the first magnetic component includes magnetic material, the second magnetic component includes a permanent magnet, and the third magnetic component includes magnetic material.

Alternatively or additionally to any of the embodiments above, wherein the first magnetic component includes a first electromagnet, the second magnetic component includes a permanent magnet, and the third magnetic component includes a second electromagnet.

Alternatively or additionally to any of the embodiments above, wherein the first magnetic component includes a first electromagnet, the second magnetic component includes magnetic material, and the third magnetic component includes a second electromagnet.

Alternatively or additionally to any of the embodiments above, wherein the first magnetic component includes an electromagnet, the second magnetic component includes a first permanent magnet, and the third magnetic component includes a second permanent magnet.

Alternatively or additionally to any of the embodiments above, wherein the first magnetic component includes an electromagnet, the second magnetic component includes a permanent magnet, and the third magnetic component includes magnetic material.

Alternatively or additionally to any of the embodiments above, wherein the first magnetic component includes an electromagnet, the second magnetic component includes magnetic material, and the third magnetic component includes a permanent magnet.

Alternatively or additionally to any of the embodiments above, wherein the first magnetic component includes a first permanent magnet, the second magnetic component includes a second permanent magnet, and the third magnetic component includes an electromagnet.

Alternatively or additionally to any of the embodiments above, wherein the first magnetic component includes a permanent magnet, the second magnetic component includes magnetic material, and the third magnetic component includes an electromagnet.

Alternatively or additionally to any of the embodiments above, wherein the first magnetic component includes a first permanent magnet, the second magnetic component includes an electromagnet, and the third magnetic component includes a second permanent magnet.

Alternatively or additionally to any of the embodiments above, wherein the first magnetic component includes magnetic material, the second magnetic component includes an electromagnet, and the third magnetic component includes magnetic material.

Alternatively or additionally to any of the embodiments above, wherein the electromagnet includes a core of magnetic material surrounded by a coil through which an electric current is passed to magnetize the core, wherein the core and coil are positionally fixed relative to one another.

Alternatively or additionally to any of the embodiments above, wherein the first electromagnet includes a first core of magnetic material surrounded by a first coil through which an electric current is passed to magnetize the first core, wherein the first core and first coil are positionally fixed relative to one another.

Alternatively or additionally to any of the embodiments above, wherein the second electromagnet includes a second core of magnetic material surrounded by a second coil through which an electric current is passed to magnetize the second core, wherein the second core and second coil are positionally fixed relative to one another.

Alternatively or additionally to any of the embodiments above, wherein the first coil and the second coil are formed from a single continuous wire.

Alternatively or additionally to any of the embodiments above, wherein the first coil is wound in a first direction, and the second coil is wound in a second direction opposite the first direction, such when electrical current is passed through the wire in a first direction, the first core of the first electromagnet is magnetized with a first polarity configuration and the second core of the second electromagnet is magnetized with a second polarity configuration opposite from the first polarity configuration.

Alternatively or additionally to any of the embodiments above, wherein when electrical current is passed through the wire in a second direction opposite the first direction, the first core of the first electromagnet is magnetized with a first reversed polarity configuration that is opposite the first polarity configuration, and the second core of the second electromagnet is magnetized with a second reversed polarity configuration opposite from the second polarity configuration.

Alternatively or additionally to any of the embodiments above, wherein when electrical current is passed through the wire in the first direction the first electromagnet is configured to magnetically push the second magnetic component to move the shroud from the first position to the second position.

Alternatively or additionally to any of the embodiments above, wherein when electrical current is passed through the wire in the first direction the second electromagnet is configured to magnetically pull the second magnetic component to move the shroud from the first position to the second position.

Alternatively or additionally to any of the embodiments above, wherein when electrical current is passed through the wire in the second direction the first electromagnet is configured to magnetically pull the second magnetic component to to move the shroud from the second position to the first position.

Alternatively or additionally to any of the embodiments above, wherein when electrical current is passed through the wire in the second direction the second electromagnet is configured to magnetically push the permanent magnet to move the shroud from the second position to the first position.

Alternatively or additionally to any of the embodiments above, wherein the first coil and the second coil are formed from separate wires.

Alternatively or additionally to any of the embodiments above, wherein the electromagnet is a solenoid.

Alternatively or additionally to any of the embodiments above, wherein the first electromagnet, the second electromagnet, or both the first electromagnet and the second electromagnet are a solenoid.

Alternatively or additionally to any of the embodiments above, wherein the body incudes a distal end and a proximal end, and defines a fluid passageway extending from the distal end to the proximal end.

Alternatively or additionally to any of the embodiments above, further comprising an oxygen sensing assembly coupled to the body.

Alternatively or additionally to any of the embodiments above, wherein the body defines a fluid passageway extending within the body, the fluid passageway is in fluid communication with the oxygen sensing assembly.

Alternatively or additionally to any of the embodiments above, wherein a connecting tube extends between the body and the oxygen sensing assembly, the connecting tube being in fluid communication with the fluid passageway.

Alternatively or additionally to any of the embodiments above, wherein the oxygen sensing assembly is configured to deactivate or prevent activation of the electrosurgical electrode if the oxygen sensing assembly senses a concentration of oxygen that exceeds a predetermined level.

Alternatively or additionally to any of the embodiments above, wherein the oxygen sensing assembly is configured to deactivate translation of the shroud between the first position and the second position if the oxygen sensing assembly senses a concentration of oxygen that exceeds a predetermined level.

Alternatively or additionally to any of the embodiments above, wherein when the shroud is in the first position, the distal tip of the electrosurgical electrode is disposed within the shroud, and wherein the oxygen sensing assembly is configured to maintain the shroud in the first position if the oxygen sensing assembly senses a concentration of oxygen that exceeds a predetermined level.

Alternatively or additionally to any of the embodiments above, wherein power to the electrode is maintained even when the oxygen sensing assembly deactivates translation of the shroud between the first position and the second position or maintains the shroud in the first position when the oxygen sensing assembly senses a concentration of oxygen that exceeds a predetermined level.

Another electrosurgical device includes a body, an electrosurgical electrode secured to the body, the electrosurgical electrode including a distal tip. The electrosurgical device also includes a shroud translatable relative to the electrosurgical electrode between a first position and a second position and a body magnetic component including an electromagnet which is operably connected to the body, the electromagnet including a core of magnetic material surrounded by a coil through which an electric current is passed to magnetize the core; wherein the core and coil are positionally fixed relative to one another. The electrosurgical device also includes a shroud magnetic component which is operably connected to the shroud, wherein the electromagnet is configured such that when electrical current is passed through the coil to thereby magnetize the core, the electromagnet magnetically interacts with the shroud magnetic component to selectively translate the shroud from the first position to the second position.

Alternatively or additionally to any of the embodiments above, wherein the shroud magnetic component is a permanent magnet.

Alternatively or additionally to any of the embodiments above, wherein the shroud magnetic component is a magnetic material.

Alternatively or additionally to any of the embodiments above, wherein the shroud magnetic component and the body magnetic component magnetically interact to releasably maintain the shroud in the first position.

Alternatively or additionally to any of the embodiments above, wherein the shroud magnetic component and the body magnetic component magnetically interact to releasably maintain the shroud in the second position.

Alternatively or additionally to any of the embodiments above, further including a second body magnetic component which is operably connected to the body and spaced from the body magnetic component.

Alternatively or additionally to any of the embodiments above, wherein the shroud magnetic component and the second body magnetic component magnetically interact to releasably maintain the shroud in the first position.

Alternatively or additionally to any of the embodiments above, wherein the shroud magnetic component and the second body magnetic component magnetically interact to releasably maintain the shroud in the second position.

Alternatively or additionally to any of the embodiments above, wherein the second body magnetic component is a permanent magnet.

Alternatively or additionally to any of the embodiments above, wherein the second body magnetic component is a magnetic material.

Alternatively or additionally to any of the embodiments above, wherein the second body magnetic component is a second electromagnet.

Alternatively or additionally to any of the embodiments above, wherein the second electromagnet incudes a second core of magnetic material surrounded by a second coil of wire through which an electric current is passed to magnetize the second core, wherein the second core and second coil are positionally fixed relative to one another.

Alternatively or additionally to any of the embodiments above, wherein the second electromagnet magnetically interacts with the shroud magnetic component to selectively translate the shroud from the second position to the first position.

Alternatively or additionally to any of the embodiments above, wherein the coil of the electromagnet and the second coil of the second electromagnet are formed from a single wire.

Alternatively or additionally to any of the embodiments above, wherein the coil of the electromagnet is wound in a first direction, and the second coil of the second electromagnet is wound in a second direction opposite the first direction.

Alternatively or additionally to any of the embodiments above, wherein when electrical current is passed through the wire in a first direction such that current is passed through the coil and the second coil, the core of the electromagnet is magnetized with a first polarity configuration and the second core of the second electromagnet is magnetized with a second polarity configuration opposite from the first polarity configuration.

Another electrosurgical device includes a body, an electrosurgical electrode secured to the body, the electrosurgical electrode including a distal tip. The electrosurgical device also includes a shroud translatable relative to the electrosurgical electrode between a first position and a second position. The electrosurgical device also includes a first electromagnet which is operably connected to the body, the first electromagnet including a first core of magnetic material surrounded by a first coil through which an electric current is passed to magnetize the core, wherein the first core and first coil are positionally fixed relative to one another. The electrosurgical device also includes a second electromagnet which is operably connected to the body and spaced from the first electromagnet, the second electromagnet including a second core of magnetic material surrounded by a second coil through which an electric current is passed to magnetize the second core, wherein the second core and second coil are positionally fixed relative to one another, wherein the first coil and the second coil are formed from a single continuous wire. The electrosurgical device also includes a permanent magnet which is operably connected to the shroud, and disposed between the first electromagnet and the second electromagnet.

Alternatively or additionally to any of the embodiments above, wherein the first coil of the first electromagnet is wound in a first direction, and the second coil of the second electromagnet is wound in a second direction opposite the first direction.

Alternatively or additionally to any of the embodiments above, wherein when electrical current is passed through the wire in a first direction such that current is passed through the first coil and the second coil, the first core of the first electromagnet is magnetized with a first polarity configuration and the second core of the second electromagnet is magnetized with a second polarity configuration opposite from the first polarity configuration.

Alternatively or additionally to any of the embodiments above, wherein when electrical current is passed through the wire in a second direction opposite the first direction, the first polarity configuration of the first core is reversed and the second polarity of the second core is reversed.

Alternatively or additionally to any of the embodiments above, wherein when electrical current is passed through the wire in a second direction opposite the first direction such that current is passed through the first coil and the second coil, the first core of the first electromagnet is magnetized with a third polarity configuration that is opposite the first polarity configuration, and the second core of the second electromagnet is magnetized with a fourth polarity configuration opposite from the second polarity configuration.

Alternatively or additionally to any of the embodiments above, wherein when electrical current is passed through the wire in a first direction the first electromagnet is configured to magnetically push the permanent magnet to move the shroud from the first position to the second position.

Alternatively or additionally to any of the embodiments above, wherein when electrical current is passed through the wire in a first direction the second electromagnet is configured to magnetically pull the permanent magnet to move the shroud from the first position to the second position.

Alternatively or additionally to any of the embodiments above, wherein when electrical current is passed through the wire in a second direction the first electromagnet is configured to magnetically pull the permanent magnet to move the shroud from the second position to the first position.

Alternatively or additionally to any of the embodiments above, wherein when electrical current is passed through the wire in the second direction the second electromagnet is configured to magnetically push the permanent magnet to move the shroud from the second position to the first position.

Alternatively or additionally to any of the embodiments above, wherein when the shroud is in the first position, the distal tip of the electrosurgical electrode is disposed within the shroud.

Alternatively or additionally to any of the embodiments above, wherein when the shroud is in the second position, the distal tip of the electrosurgical electrode is exposed distally of the shroud.

Another electrosurgical device includes a body, an electrosurgical electrode secured to the body, the electrosurgical electrode including a distal tip. The electrosurgical device also includes a shroud translatable relative to the electrosurgical electrode between a first position and a second position, a body magnetic component which is operably connected to the body, and an electromagnet which is operably connected to the shroud, the electromagnet including a core of magnetic material surrounded by a coil of wire through which an electric current is passed to magnetize the core, wherein the core and coil are positionally fixed relative to one another. Further, the electromagnet is configured such that when electrical current is passed through the coil to thereby magnetize the core, the electromagnet magnetically interacts with the body magnetic component to selectively translate the shroud from the first position to the second position.

Alternatively or additionally to any of the embodiments above, wherein the body magnetic component is selected from one or more of a permanent magnet, a magnetic material, and a second electromagnet.

Alternatively or additionally to any of the embodiments above, further including a second body magnetic component which is operably connected to the body and spaced from the body magnetic component, wherein the electromagnet is disposed between the body magnetic component and the second body magnetic component.

Alternatively or additionally to any of the embodiments above, wherein the second body magnetic component is selected from one or more of a permanent magnet, a magnetic material, and a third electromagnet.

Alternatively or additionally to any of the embodiments above, wherein the electromagnet is configured such that when electrical current is passed through the coil to thereby magnetize the core, the electromagnet magnetically interacts with the second body magnetic component to selectively translate the shroud from the second position to the first position.

Alternatively or additionally to any of the embodiments above, wherein the body magnetic component and the second body magnetic component are permanent magnets.

Alternatively or additionally to any of the embodiments above, wherein when the shroud is in the first position, the distal tip of the electrosurgical electrode is disposed within the shroud.

Alternatively or additionally to any of the embodiments above, wherein when the shroud is in the second position, the distal tip of the electrosurgical electrode is exposed distally of the shroud.

Another electrosurgical device includes a body, an electrosurgical electrode secured to the body, the electrosurgical electrode including a distal tip. The electrosurgical device also includes a shroud translatable relative to the electrosurgical electrode between a first position and a second position and an electromagnet operably connected to one of the body and the shroud, the electromagnet including a core of magnetic material surrounded by a coil of wire through which an electric current is passed to magnetize the core. The electrosurgical device also includes a magnetic component operably connected to the other one of the body and the shroud, wherein the electromagnet is configured such that when electrical current is passed through the coil to thereby magnetize the core, the electromagnet magnetically interacts with the magnetic component to selectively translate the shroud from the first position to the second position.

Alternatively or additionally to any of the embodiments above, wherein the magnetic component is selected from one or more of a permanent magnet, a magnetic material, and a second electromagnet.

Another electrosurgical device includes a body, an electrosurgical electrode secured to the body, the electrosurgical electrode including a distal tip. The electrosurgical device also includes a shroud translatable relative to the electrosurgical electrode between a first position and a second position, wherein when the shroud is in the first position, the distal tip of the electrosurgical electrode is disposed within the shroud, and wherein when the shroud is in the second position, the distal tip of the electrosurgical electrode is exposed distally of the shroud. The electrosurgical device also includes a first electromagnet which is operably connected to the body, a second electromagnet which is operably connected to the body, and a permanent magnet operably connected to the shroud, wherein the permanent magnet is disposed between the first electromagnet and the second electromagnet.

Alternatively or additionally to any of the embodiments above, wherein the first electromagnet is configured to magnetically interact with the permanent magnet to move the shroud from the first position to the second position.

Alternatively or additionally to any of the embodiments above, wherein the first electromagnet is configured to magnetically push the permanent magnet to move the shroud from the first position to the second position.

Alternatively or additionally to any of the embodiments above, wherein the first electromagnet is configured to magnetically pull the permanent magnet to move the shroud from the first position to the second position.

Alternatively or additionally to any of the embodiments above, wherein the second electromagnet is configured to magnetically interact with the permanent magnet to move the shroud from the second position to the first position.

Alternatively or additionally to any of the embodiments above, wherein the second electromagnet is configured to magnetically push the permanent magnet to move the shroud from the second position to the first position.

Alternatively or additionally to any of the embodiments above, wherein the second electromagnet is configured to magnetically pull the permanent magnet to move the shroud from the second position to the first position.

Another electrosurgical device includes a body and an electrosurgical electrode secured to the body, the electrosurgical electrode including a distal tip. The electrosurgical device also includes a shroud translatable relative to the electrosurgical electrode between a first position and a second position, wherein when the shroud is in the first position, the distal tip of the electrosurgical electrode is disposed within the shroud, and wherein when the shroud is in the second position, the distal tip of the electrosurgical electrode is exposed distally of the shroud. The electrosurgical device also includes a first permanent magnet which is operably connected to the body, a second permanent magnet operably connected to the shroud, and a third permanent magnet which is operably connected to the body and spaced from the first permanent magnet, wherein the second permanent magnet is disposed between the first permanent magnet and the second permanent magnet.

Alternatively or additionally to any of the embodiments above, wherein the first and second permanent magnets magnetically interact to releasably maintain the shroud in the first position.

Alternatively or additionally to any of the embodiments above, wherein the second and third permanent magnets magnetically interact to releasably maintain the shroud in the second position.

Alternatively or additionally to any of the embodiments above, further including a slidable actuator operably coupled to the shroud and disposed exterior to the housing, the slidable actuator configured for engagement by a user to translate the shroud relative to the electrosurgical electrode between the first position and second positions.

Another electrosurgical device includes a body and an electrosurgical electrode secured to the body, the electrosurgical electrode including a distal tip. The electrosurgical device also includes a shroud translatable relative to the electrosurgical electrode between a first position and a second position, wherein when the shroud is in the first position, the distal tip of the electrosurgical electrode is disposed within the shroud, and wherein when the shroud is in the second position, the distal tip of the electrosurgical electrode is exposed distally of the shroud. The electrosurgical device also includes an activation member coupled to the body, the activation member being configured to activate the electrosurgical electrode and a guard coupled to the body and movable relative to the activation member. Further, the guard is configured to shift between an active position where the guard allows activation of the electrosurgical electrode by the activation member and an inactive position where the guard prevents activation of the electrosurgical electrode by the activation member, wherein the guard is disposed underneath the activation member when the guard is in the inactive position.

Alternatively or additionally to any of the embodiments above, wherein the guard is disposed between the activation member and the body when the guard is in the inactive position.

Alternatively or additionally to any of the embodiments above, wherein the guard is operably coupled to the shroud and is configured for engagement by a user to translate the shroud relative to the electrosurgical electrode between the first and second positions. Alternatively or additionally to any of the embodiments above, wherein the activation member includes a button.

Alternatively or additionally to any of the embodiments above, wherein the activation member includes a toggle.

Alternatively or additionally to any of the embodiments above, further comprising a first magnetic component which is operably connected to the body and a second magnetic component which is operably connected to the shroud.

Alternatively or additionally to any of the embodiments above, wherein the first and second magnetic components magnetically interact to releasably maintain the shroud in the first position.

Alternatively or additionally to any of the embodiments above, wherein the first and second magnetic components are each selected from one of an electromagnet, a permanent magnet, and a magnetic material.

An example electrosurgical system includes a body having a fluid passageway defined therein, an electrosurgical electrode secured to the body, a shroud translatable relative to the electrosurgical electrode between a first position and a second position, a connecting tube coupled to the body and in fluid communication with the fluid passageway, an oxygen sensing assembly coupled to and in fluid communication with the connecting tube, a first magnetic component which is operably connected to the body, and a second magnetic component which is operably connected to the shroud, wherein the first and second magnetic components magnetically interact to releasably maintain the shroud in the first position.

Alternatively or additionally to any of the embodiments above, wherein the oxygen sensing assembly is configured to prevent translation of the shroud between the first position and the second position if the oxygen sensing assembly senses a concentration of oxygen that exceeds a predetermined level.

Alternatively or additionally to any of the embodiments above, wherein power to the electrode is maintained even when the oxygen sensing assembly prevents translation of the shroud between the first position and the second position.

Alternatively or additionally to any of the embodiments above, wherein the oxygen sensing assembly is configured to maintain the shroud in the first position if the oxygen sensing assembly senses a concentration of oxygen that exceeds a predetermined level.

Alternatively or additionally to any of the embodiments above, wherein power to the electrode is maintained even when the oxygen sensing assembly maintains the shroud in the first position.

Alternatively or additionally to any of the embodiments above, wherein the oxygen sensing assembly is configured to deactivate the electrosurgical electrode if the oxygen sensing assembly senses a concentration of oxygen that exceeds a predetermined level.

Alternatively or additionally to any of the embodiments above, wherein the oxygen sensing assembly is configured to prevent actuation of the electrosurgical electrode if the oxygen sensing assembly senses a concentration of oxygen that exceeds a predetermined level.

Alternatively or additionally to any of the embodiments above, wherein the body forms at least a portion of and electrosurgical handpiece, and power to the handpiece is maintained even when the oxygen sensing assembly senses a concentration of oxygen that exceeds a predetermined level.

Alternatively or additionally to any of the embodiments above, wherein when the shroud is in the first position, the distal tip of the electrosurgical electrode is disposed within the shroud.

Alternatively or additionally to any of the embodiments above, wherein the first magnetic component is selected from one or more of a permanent magnet, a magnetic material, and an electromagnet.

Alternatively or additionally to any of the embodiments above, wherein the second magnetic component is selected from one or more of a permanent magnet, a magnetic material, and an electromagnet.

Alternatively or additionally to any of the embodiments above, wherein the oxygen sensing assembly is a separate component spaced from the body, and in fluid communication with the fluid passageway of the body through the connecting tube.

Alternatively or additionally to any of the embodiments above, wherein the oxygen sensing assembly comprises: a housing; a fluid pathway extending within the housing; and an oxygen sensor in fluid communication with the fluid pathway.

Alternatively or additionally to any of the embodiments above, wherein the oxygen sensing assembly includes a negative pressure source or is configured to be connected to a negative pressure source.

Alternatively or additionally to any of the embodiments above, wherein the system is configured such that a negative pressure is applied to draw fluid through the fluid passage of the body, through the connecting tube coupled to the body, and into the oxygen sensing assembly.

Alternatively or additionally to any of the embodiments above, wherein the negative pressure source is a smoke evacuator.

Another electrosurgical system includes an electrosurgical handpiece. The electrosurgical handpiece includes a body having a fluid passageway defined therein, an electrosurgical electrode secured to the body, the electrode including a distal tip, and a shroud translatable relative to the electrosurgical electrode between a first position where the distal tip of the electrosurgical electrode is disposed within the shroud, and a second position where the distal tip of the electrosurgical electrode is exposed distally of the shroud, a connecting tube coupled to the handpiece and in fluid communication with the fluid passageway, an oxygen sensing assembly spaced from the handpiece and in fluid communication with the fluid passageway of the handpiece through the connecting tube. Further, the oxygen sensing assembly is configured to render one or more component of the handpiece inoperable if the oxygen sensing assembly senses a concentration of oxygen that exceeds a predetermined level.

Alternatively or additionally to any of the embodiments above, wherein the oxygen sensing assembly renders one or more components of the handpiece inoperable through one or more of the following: preventing translation of the shroud between the first position and the second position, actuating the shroud into the first position, maintaining the shroud in the first position, deactivating the electrosurgical electrode and preventing activating of the electrosurgical electrode.

Alternatively or additionally to any of the embodiments above, wherein power to the handpiece is maintained even when the oxygen sensing assembly senses a concentration of oxygen that exceeds a predetermined level.

Alternatively or additionally to any of the embodiments above, wherein the oxygen sensing assembly includes a housing, a fluid pathway extending within the housing, and an oxygen sensor in fluid communication with the fluid pathway.

Alternatively or additionally to any of the embodiments above, wherein the oxygen sensing assembly includes a negative pressure source or is configured to be connected to a negative pressure source.

Alternatively or additionally to any of the embodiments above, wherein the system is configured such that a negative pressure is applied to draw fluid through the fluid passage of the body, through the connecting tube coupled to the body, and into the oxygen sensing assembly.

Alternatively or additionally to any of the embodiments above, wherein the negative pressure source is a smoke evacuator.

Alternatively or additionally to any of the embodiments above, wherein the handpiece includes a first magnetic component which is operably connected to the body; and a second magnetic component which is operably connected to the shroud, wherein the first and second magnetic components magnetically interact to releasably maintain the shroud in the first position.

Another example electrosurgical device includes a body and an electrosurgical electrode secured to the body, the electrosurgical electrode including a distal tip. The electrosurgical device further includes a shroud translatable relative to the electrosurgical electrode between a first position and a second position, an electromagnet configured to translate the shroud between a first position and a second position and an actuator assembly. The actuator assembly includes an electrosurgical actuator assembly including a first part configured to actuate the electrosurgical electrode into a cutting mode, and including a second part to actuate the electrosurgical electrode into a coagulation mode, and a central actuator disposed between the first and second parts of the electrosurgical actuator assembly and configured to actuate the electromagnet.

Alternatively or additionally to any of the embodiments above, wherein the central actuator has an outer perimeter, and wherein the first and second parts are shaped such that in combination they substantially surround the outer perimeter of the central actuator.

Alternatively or additionally to any of the embodiments above, wherein the first part is a first button, the second part is a second button, and the central actuator is a third button disposed between the first and second buttons.

Alternatively or additionally to any of the embodiments above, wherein the actuator assembly is configured such that the central actuator may be actuated at the same time as at least one of the first part and the second part.

Alternatively or additionally to any of the embodiments above, wherein the actuator assembly is configured such that the central actuator may be actuated at the same time as at least one of the first part and the second part by a user using a single digit.

Alternatively or additionally to any of the embodiments above, wherein when the shroud is in the first position, the distal tip of the electrosurgical electrode is disposed within the shroud, and wherein when the shroud is in the second position, the distal tip of the electrosurgical electrode is exposed distally of the shroud.

Alternatively or additionally to any of the embodiments above, wherein the electromagnet is operably connected to the body, and further including a second magnetic component which is operably connected to the shroud.

Alternatively or additionally to any of the embodiments above, wherein the second magnetic component is selected from one of an electromagnet, a permanent magnet, and a magnetic material.

Another electrosurgical device includes a body and an electrosurgical electrode secured to the body, the electrosurgical electrode including a distal tip. The electrosurgical device also includes a shroud translatable relative to the electrosurgical electrode between a first position and a second position, a slider coupled to the body and translatable relative to the body, the slider being operably coupled to the shroud and being configured for engagement by a user to translate the shroud relative to the electrosurgical electrode between the first and second positions, an activation button coupled to the slider, a switch disposed under the slider, and configured to activate the electrosurgical electrode. Further, when the slider is translated such that the shroud is in the first position, the activation button is misaligned with the switch such that the actuation button cannot engage the switch, and when the slider is translated such that the shroud is in the second position, the activation button is aligned with the switch such that the actuation button can engage the switch to activate the electrode.

Alternatively or additionally to any of the embodiments above, wherein when the shroud is in the first position, the distal tip of the electrosurgical electrode is disposed within the shroud, and wherein when the shroud is in the second position, the distal tip of the electrosurgical electrode is exposed distally of the shroud.

Alternatively or additionally to any of the embodiments above, further comprising a first magnetic component which is operably connected to the body and a second magnetic component which is operably connected to the shroud.

Alternatively or additionally to any of the embodiments above, wherein the first and second magnetic components magnetically interact to releasably maintain the shroud in the first position.

Alternatively or additionally to any of the embodiments above, wherein the first and second magnetic components are each selected from one of an electromagnet, a permanent magnet, and a magnetic material.

Another electrosurgical device includes a body, a first component extending from the body, a second component translatable relative to the first component between a first position and a second position, a first magnetic component which is operably connected to the body, and a second magnetic component which is operably connected to the second component. Further, the first and second magnetic components magnetically interact to releasably maintain the second component in the first position.

Alternatively or additionally to any of the embodiments above, wherein the first magnetic component is selected from one or more of a permanent magnet, a magnetic material, and an electromagnet.

Alternatively or additionally to any of the embodiments above, wherein the second magnetic component is selected from one or more of a permanent magnet, a magnetic material, and an electromagnet.

Alternatively or additionally to any of the embodiments above, further including a third magnetic component operably connected to the body.

Alternatively or additionally to any of the embodiments above, wherein the second and third magnetic components magnetically interact to releasably maintain the second component in the second position.

Alternatively or additionally to any of the embodiments above, wherein the second magnetic component is disposed between the first and the third magnetic components.

Alternatively or additionally to any of the embodiments above, wherein the third magnetic component is selected from one or more of a permanent magnet, a magnetic material, and an electromagnet Alternatively or additionally to any of the embodiments above, wherein the first component is a shroud extending from the body, and the second component is an electrosurgical electrode translatable relative to the shroud.

Alternatively or additionally to any of the embodiments above, wherein the shroud is a separate component attached to the body.

Alternatively or additionally to any of the embodiments above, wherein the shroud is of unitary construction with the body.

Alternatively or additionally to any of the embodiments above, wherein the position of the shroud is fixed relative to the body.

Alternatively or additionally to any of the embodiments above, wherein the first component is an electrode extending from the body, and the second component is a shroud translatable relative to the electrode.

Another electrosurgical device includes a body, a shroud extending from the body, an electrode translatable relative to the shroud between a first position and a second position, a first magnetic component which is operably connected to the body, and a second magnetic component which is operably connected to the electrode. Further, the first and second magnetic components magnetically interact to releasably maintain the electrode in the first position.

Alternatively or additionally to any of the embodiments above, wherein the first magnetic component is selected from one or more of a permanent magnet, a magnetic material, and an electromagnet.

Alternatively or additionally to any of the embodiments above, wherein the second magnetic component is selected from one or more of a permanent magnet, a magnetic material, and an electromagnet.

Alternatively or additionally to any of the embodiments above, further including a third magnetic component operably connected to the body.

Alternatively or additionally to any of the embodiments above, wherein the second and third magnetic components magnetically interact to releasably maintain the electrode in the second position.

Alternatively or additionally to any of the embodiments above, wherein the second magnetic component is disposed between the first and the third magnetic components.

Alternatively or additionally to any of the embodiments above, wherein the third magnetic component is selected from one or more of a permanent magnet, a magnetic material, and an electromagnet.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
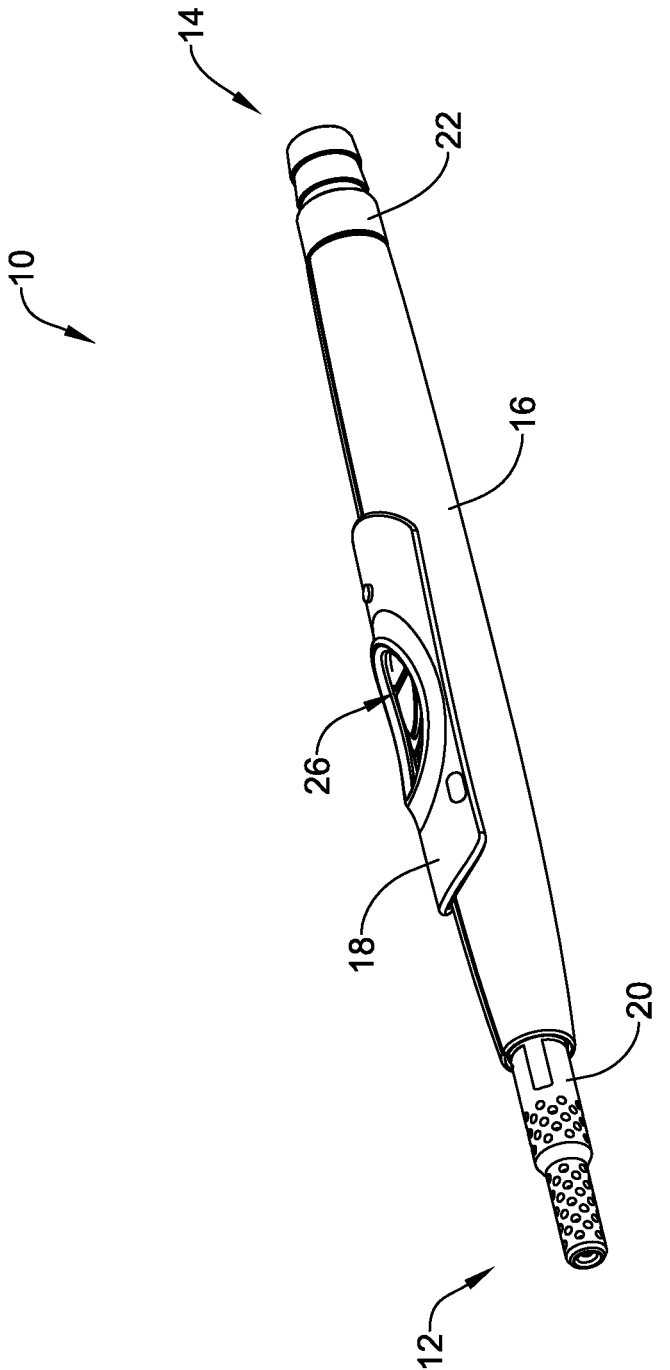
FIG. 1 illustrates an example electrosurgical device in a first position.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit to the scope of the disclosure.

Radiofrequency electrosurgery may be performed using a radio frequency electrosurgical system which may include various components such as an interface console, a smoke evacuation device and/or an electrosurgical generator. Further, one or more of the components of the electrosurgical system may be attached to an electrosurgical device (e.g., an electrosurgical instrument, an electrosurgical pen, an electrosurgical pencil, etc.). In some instances, the electrosurgical device may include a single electrode (e.g., a monopolar instrument) or two electrodes (e.g., a bipolar instrument).

A monopolar electrosurgical device may include an "active electrode" when energized, yet may also require the application of a "dispersive electrode" elsewhere on the patient's body. The dispersive electrode may function to disperse the RF current, thereby preventing thermal injury to the underlying tissue. This dispersive electrode may be mistakenly called a "grounding pad" or "neutral electrode." However, virtually all currently available radiofrequency electrosurgical systems are designed to function with isolated circuits whereby the dispersive electrode is directly attached to the electrosurgical unit, and not to "ground." The same electrical current is transmitted across both the dispersive electrode and the active electrode, and therefore, is not "neutral."

Bipolar electrosurgical devices, however, are generally designed with two "active" electrodes. However, a bipolar electrosurgical device can be designed such that one electrode is dispersive. The main advantage of bipolar electrosurgical devices is that the only part of the patient included in the circuit is that part which is located between the two electrodes, a circumstance that eliminates the risk of current diversion and related adverse events.

FIG. 1 illustrates an example electrosurgical device 10, which may be referred to as an electrosurgical pen, an electrosurgical pencil, an electrocautery device, etc. The electrosurgical device 10 may include a distal end region 12 and a proximal end region 14. The distal end reign 12 of the electrosurgical device 10 may include a shroud 20 (e.g., holster, internal holster, holster mechanism) which is coupled to a body portion 16. In some instances, the shroud 20 may be designed to be permanently secured to the body portion 16 (e.g., the shroud 20 may not be easily removed from the body and replaced with a different shroud). However, in other instances, the shroud 20 may be releasably secured to the body 16 to permit replacement of the shroud 20 (e.g., the shroud 20 may be replaced with other shrouds of different sizes, shapes, apertures, etc.). The shroud 20 and its engagement with the body 16 will be described in greater detail below.

FIG. 1 further illustrates that the electrosurgical device 10 may further include a proximal connector 22 positioned along the proximal end region 14 of the electrosurgical device 10. As will be described in greater detail below, the proximal connector 22 may be utilized to attach the electrosurgical device 10 to an electrosurgical system 500 (e.g., shown in FIG. 30).

As discussed above, the electrosurgical device 10 may include an electrosurgical electrode 24 (not visible in FIG. 1, but shown in FIG. 2) which may be used to apply electrical current as an energy source used in electrosurgery and/or electrocautery procedures to cut, coagulate, desiccate, ablate and/or fulgurate tissue. Some examples of electrosurgical procedures may include the use and/or creation of radio frequency, plasma, ionized gas (e.g. ionized argon), or the like. Other examples include the application of a high-frequency (radio frequency) alternating polarity, electrical current to biological tissue as a means to cut, coagulate, desiccate, or fulgurate tissue. In some instances, the electrode 24 may include a heated probe and/or electrode tip that may be used via heat conduction for the treatment of tissue.

Further, the electrode 24 may generate intense heat during use, and therefore, it can be appreciated that electrosurgical device 10 may be designed to shield the electrode 24 when not in use. Specifically, the electrosurgical device 10 may include an actuatable, protective shroud 20 which covers the electrode 24 when not in use, but also actuates (e.g., translates between a first position to a second position) to expose the electrode 24 to cut or coagulate tissue as desired. In some examples, the shroud 20 may be constructed from one or more materials which may be non-flammable, heat-resistant, heat-retardant, etc.

Figure 2:
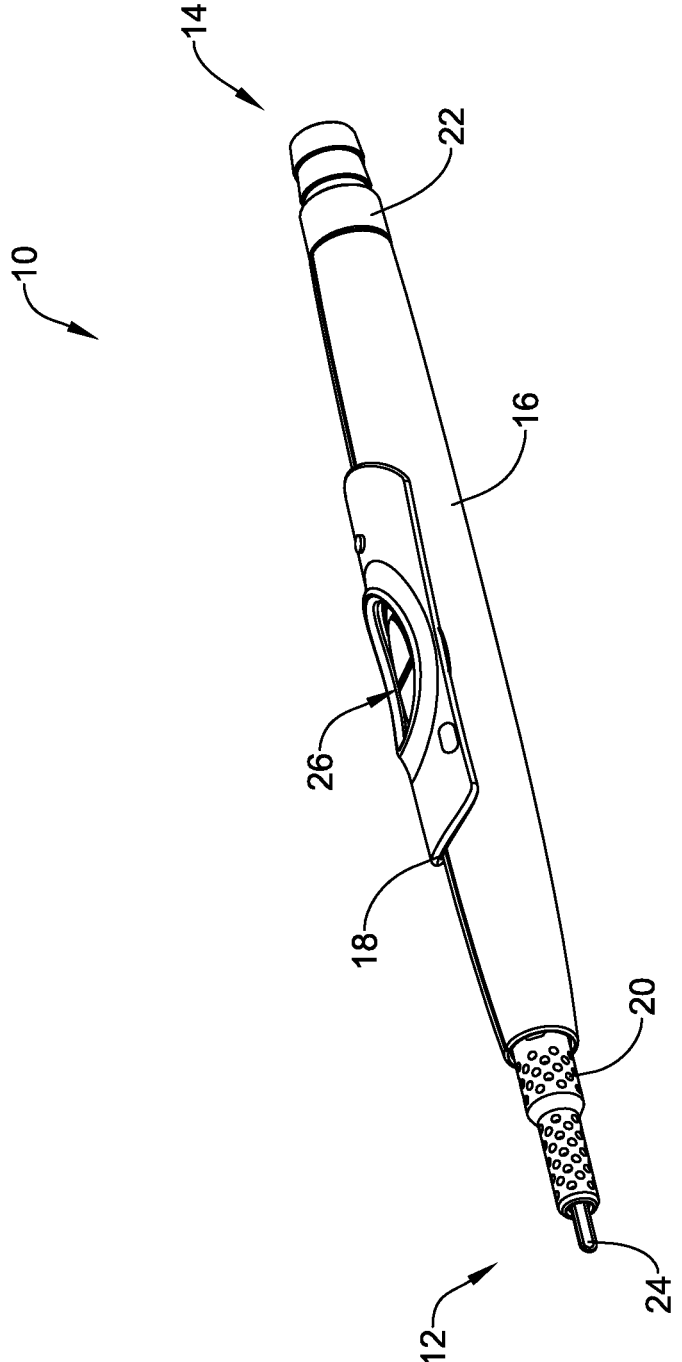
FIG. 2 illustrates the example electrosurgical device shown in FIG. 1 in a second position.

A variety of electrosurgical devices are disclosed herein which include a variety of mechanisms designed to actuate the shroud 20 to expose or cover the electrode 24. For example, FIG. 1 illustrates that the electrosurgical device 10 may include a sliding cover (e.g., guard, sliding guard, etc.) 18 which may be actuated by a user to translate (e.g., actuate, shift, move, etc.) the shroud 20 from a first position in which an electrode 24 (not visible in FIG. 1) is covered to second position in which the electrode 24 is exposed. For example, FIG. 2 illustrates the electrosurgical device 10 of FIG. 1 whereby the sliding cover 18 has been manipulated by a user to translate (e.g., retract, etc.) the shroud 20 in a distal-to-proximal direction (e.g., the shroud 20 translates relative to the body 16 from the distal end region 12 toward the proximal end region 14 of the electrosurgical device 10) to expose the tip of the electrode 24. It can be appreciated that the electrode 24 may remain stationary relative to the body 16, while the shroud 20 actuates relative to both the stationary electrode 24 and the body 16.

Additionally, FIG. 1 illustrates that, when the sliding cover 18 is in a distalmost position (whereby the shroud 20 is covering the electrode 24), the sliding cover 18 may partially cover a switch 26 designed to permit a user to power the electrode 24. It can be appreciated that when the shroud 20 is in a first position (e.g., covering the electrode 24), it may be desirable to position the sliding cover 18 over at least a portion of the switch 26 (e.g., covering a portion of the switch 26), thereby preventing a user from inadvertently actuating the switch 26 to power the electrode 24. As will be described in greater detail below, when a user actuates (e.g., slides, shifts, moves, pulls, etc.) the sliding cover 18 in a distal-to-proximal direction (which simultaneously actuates the shroud 20 to expose the electrode 24), the entire switch 26 may become accessible to the user, thereby allowing the user to access the switch 26 and power the exposed electrode 24 to cut and/or coagulate tissue.

While the above discussion describes the shroud 20 as being in a "first position" when the shroud 20 is covering the electrode 24 and being in a "second position" when the shroud 20 is retracted to expose the electrode 24, it is also contemplated that the terms "first position" and "second position" may be used interchangeably (e.g., reversed) when describing the relative position of the shroud 20 relative to the electrode 24. For example, the term "second position" may describe a configuration in which the shroud 20 is covering the electrode 24 and the term "second position" may describe a configuration in which the shroud 20 is retracted to expose the electrode 24.

Figure 3:
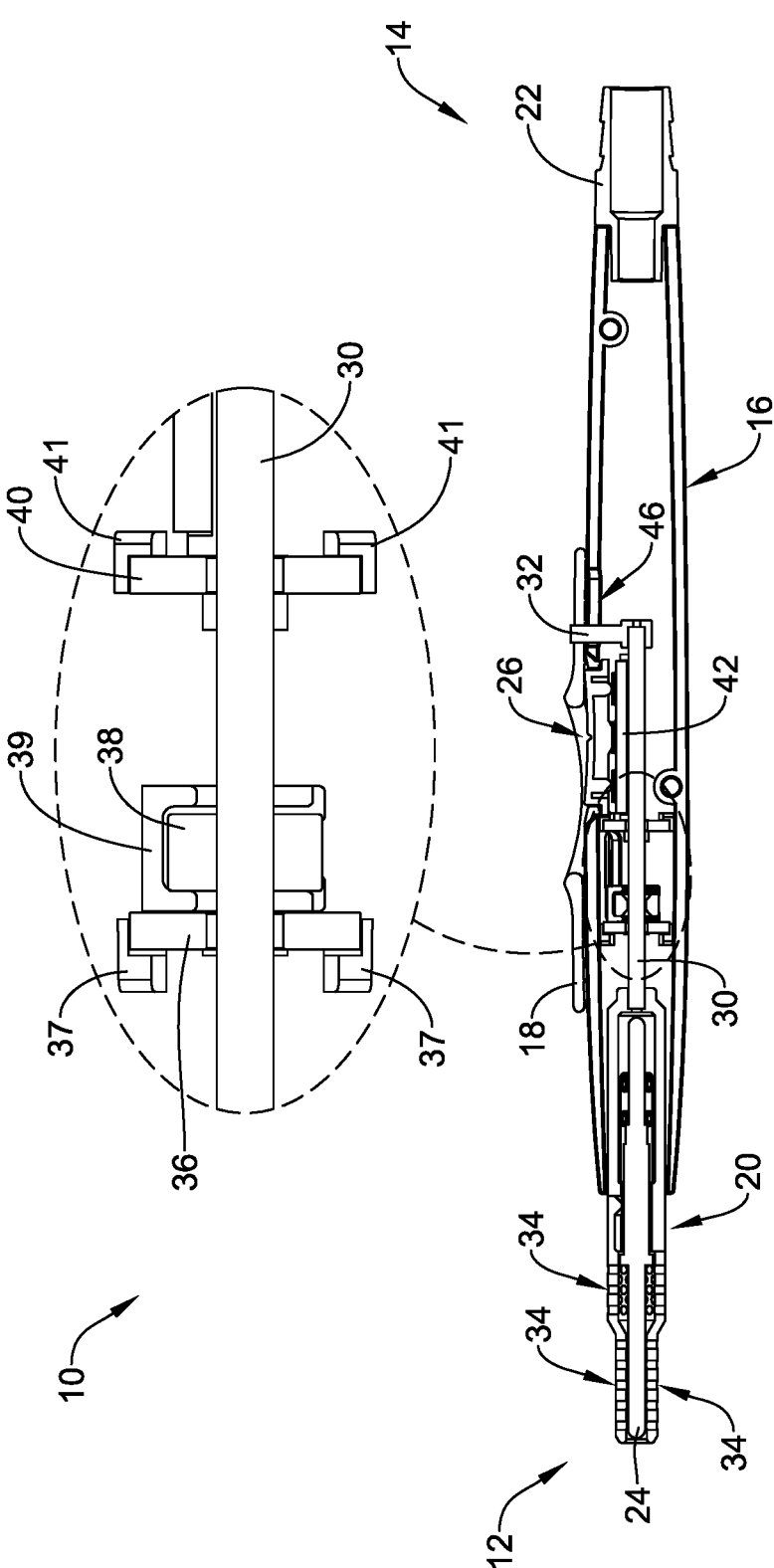
FIG. 3 illustrates a cross-sectional side view of the example electrosurgical device shown in FIG. 1.

FIG. 3 illustrates a cross-sectional side view of the electrosurgical device 10 shown in FIG. 1. For example, FIG. 3 illustrates the shroud 20 in a first position (e.g., positioned in a distal-most position relative to the body 16) in which it is covering the electrode 24. Further, FIG. 3 illustrates that the sliding cover 18 is covering at least a portion of the switch 26, thereby preventing actuation of the switch 26 to energize the electrode 24. The position of the sliding cover 18 shown in FIG. 3 illustrates a configuration in which the sliding cover 18 has been shifted to a distal-most position relative to the body 16.

As discussed above, the electrosurgical device 10 may be designed such that actuation (e.g., sliding, etc.) of the sliding cover 18 may simultaneously actuate the shroud 20. For example, actuation of the sliding cover 18 in a distal-to-proximal direction will simultaneously actuate the shroud 20 in a distal-to-proximal direction. Similarly, actuation of the sliding cover 18 in a proximal-to-distal direction will actuate the shroud 20 in a proximal-to-distal direction. The simultaneous actuation of the sliding cover 18 and the shroud 20 occurs because the sliding cover 18 and the shroud 20 are attached to one another via a linkage assembly. Specifically, FIG. 3 illustrates that the proximal end of the shroud 20 may be connected to a distal end of a shaft 30, which generally extends along the longitudinal axis of the body 16. Further, FIG. 3 illustrates that the proximal end of the shaft 30 may be connected to a portion of a linkage 32. As shown in FIG. 3, the linkage 32 may generally extend vertically, thereby connecting the proximal end of the shaft 30 to a proximal end region of the sliding cover 18.

Further, FIG. 3 illustrates that the linkage 32 may pass from an interior cavity of the body 16 through an aperture 46 and attach to the proximal end region of the sliding cover 18. It can be appreciated from FIG. 3 that the aperture 46 may extend longitudinally along the body 16 (see FIG. 5 for an alternative view of the aperture 46) which permits the linkage 32 to shift longitudinally (relative to the body 16) within the aperture 46. Accordingly, to expose the electrode 24 as described above, a user may slide the sliding cover 18 in a distal-to-proximal direction, which also shifts the linkage 32 in a distal-to-proximal direction, which, in turn, pulls the shaft 30 and the shroud 20 in a distal-to-proximal direction, thereby exposing the electrode 24 (which is held stationary relative to the body 16).

Further, as described above, actuating the sliding cover 18 in a distal-to-proximal direction may also uncover the switch 26, thereby permitting the user to power the electrode 24 to cut and/or coagulate tissue. To energize the electrode 24, energy must be supplied to the electrode 24 from an energy source (e.g., an electrosurgical generator located away from the electrosurgical device 10). FIG. 3 illustrates that both the body 16 and the proximal connector 22 may generally include hollow cavities which may permit one or more wires to extend from the energy source, through the hollow cavities of the proximal connector 22 and/or the body 16, whereby the wires may be attached to a circuit board 42 aligned with the underside of the switch 26. From the circuit board 42, the wires may further extend and attach to the electrode 24. One skilled in the art can appreciate that the electrosurgical device 10 may include known wiring configurations common to electrosurgical devices (e.g., electrosurgical pens).

As discussed above, the wires may transfer an electrical current from the electrosurgical generator to supply energy to the electrode 24 to cut, coagulate, desiccate, ablate, fulgurate, etc. tissue during an electrosurgery. Engagement of the switch 26 with the circuit board 42 will be described in greater detail below with respect to FIG. 4.

Figure 5:
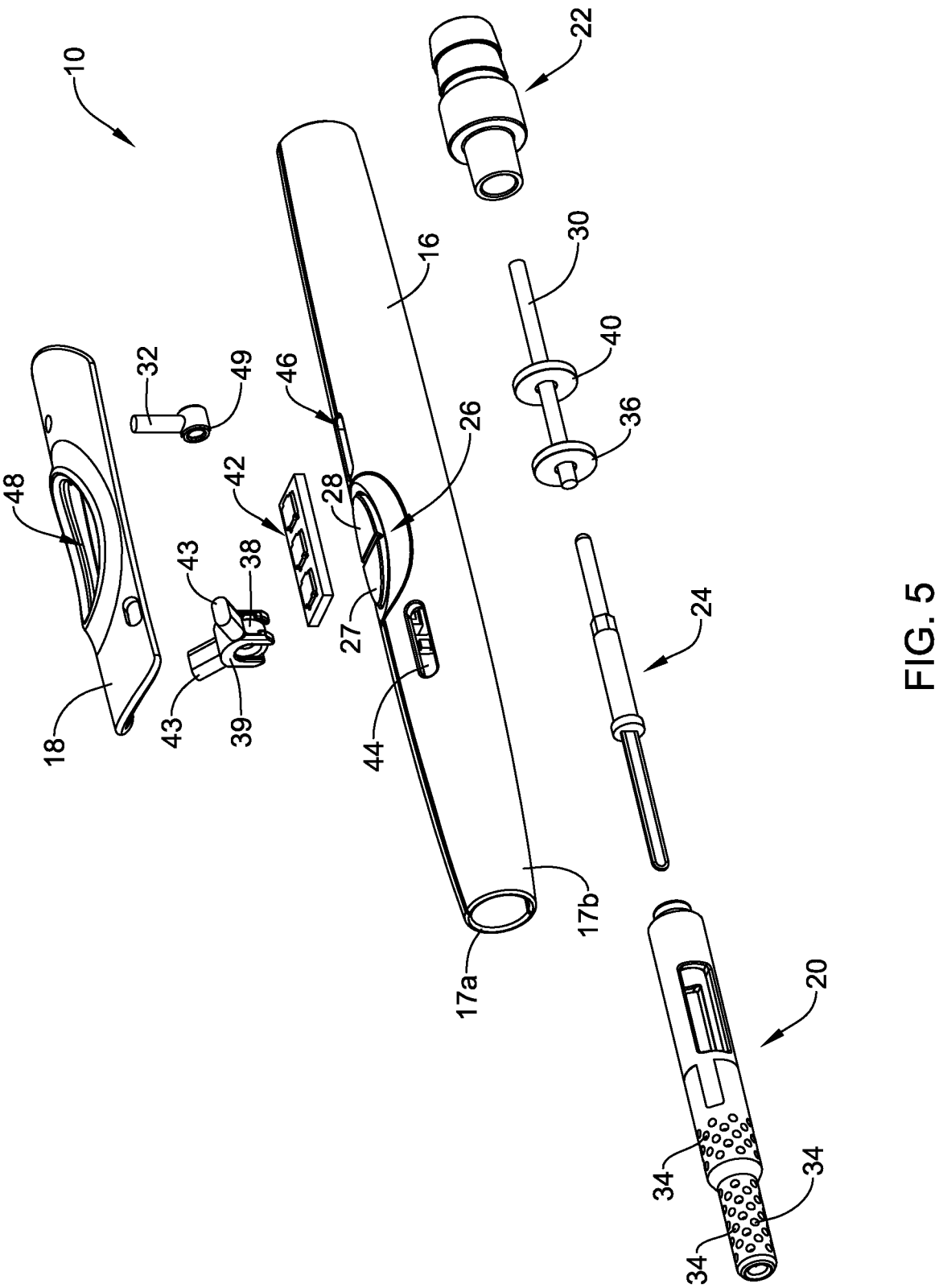
FIG. 5 illustrates an exploded view of the electrosurgical device shown in FIG. 1.

It can be further appreciated from FIG. 3 that the body 16 may be constructed from one or more individual components that attach with one another to form the body 16 shown in FIGS. 1-2. For example, the body 16 may be formed from two separate components which combine in a clamshell configuration to form the body 16. It can be appreciated that the illustration shown in FIG. 3 shows one "half" of the clamshell defining the body 16 (as the mating half of the body 16 has been removed to show the cross-sectional view). However, it is noted that FIG. 5 illustrates the body 16 as having a first body component 17a attached to a second body component 17b to form the entire body 16.

FIG. 3 further illustrates that the shroud 20 may include one or more apertures 34 (e.g., holes, openings, fluid pathways, channels, etc.) extending from an outer surface of the shroud 20, through the wall of the shroud 20 to the interior lumen of the shroud 20. The apertures 34 may be designed to permit fluid, air, smoke, etc. to flow from a position outside the shroud 20 through the interior lumen of the shroud 20 (which may be occupied by the electrode 24). Further, the interior lumen of the shroud 20 may be in fluid communication with the hollow cavity (e.g., lumen) of the body 16. Further yet, as described above, the hollow cavity of the body 16 may be in fluid communication with the lumen of the proximal connector 22. The proximal connector 22 may be coupled to a connecting tube which may be further coupled to an electrosurgical system 500 (e.g., shown in FIG. 30).

It can be appreciated that, in some examples, the electrode 24 may need to be cooled during or after operation, and therefore, it may be desirable to pass fluid through the apertures 34 and into the lumen of the shroud 20, along the electrode 24 (where it acts to cool the electrode 24) and out of the electrosurgical device 10 via a continuous fluid pathway extending through the hollow cavity (e.g., inner lumen) of the body 16 and the lumen of the proximal connector 22. Similarly, in some instances, smoke created during the cut/coagulation process may be evacuated from the surgical site through the same fluid pathway.

Additionally, it is contemplated that in any of the examples described herein, a continuous flow pathway that passes fluid (or smoke) extends within the body 16 and/or the lumen of the proximal connector may be isolated from one or more components of the electrosurgical device via one or more partitions, channels, chambers, or the like. For example, one or more partitions, channels, chambers, etc. may be utilized to separate (e.g. isolate, divide, etc.) the continuous flow pathway from one or more electronic components (e.g., wires, circuit boards, etc.) of the electrosurgical device 10. It can be appreciated that isolating the continuous flow pathway from the electronic components, for example, may protect the electronic components from contact with fluid (or smoke) flowing along the continuous flow pathway.

FIG. 3 further illustrates that the electrosurgical device 10 may include one or more features which are designed to maintain the shroud 20 in either the first (e.g., covered) or second (e.g., retracted) position until the user opts to manually actuate the shroud 20 between the first/second position to the second/first position, respectively. Specifically, FIG. 3 includes a magnetic assembly which may maintain the shroud 20 in given position (e.g., covering or exposing the electrode 24) until the user opts to move the shroud 20 to an alternative position (e.g., covering or exposing the electrode 24).

The magnetic assembly described above is shown in the detailed view of FIG. 3. The magnetic assembly may include a first magnetic component 36 held in a stationary position by one or more engagement features 37 located on the interior surface of the body 16. The detailed view of FIG. 3 further illustrates that the magnetic assembly may include a second magnetic component 38 which may be attached to the shaft 30 via a housing 39 (e.g., bracket, attachment structure, support structure, etc.). In other words, the second magnetic component 38 may be supported by the housing 39, whereby the housing 39 may be fixedly attached to the shaft 30 such that actuation of the shaft 30 translate both the housing 39 and the second magnetic component 38 supported by the housing 39.

FIG. 3 further illustrates that each of the first magnetic component 36, the second magnetic component 38 and the housing 39 may include an aperture which is designed to permit the shaft 30 to extend therethrough. As described above, the housing 39 may be fixedly attached to the shaft 30, and therefore, may translate relative to the body 16 and the first magnetic component 36 when the shaft 30 translates (during actuation of the sliding cover 18 and the shroud 20, for example). However, FIG. 3 illustrates that the shaft 30 may pass through an opening in the first magnetic component 36 when translating relative thereto. In other words, the first magnetic component 36 may remain stationary when the shaft 30 and the second magnet component 38 are translated relative to the body 16.

Additionally, when in the position shown in FIG. 3 (e.g., the first position in which the shroud 20 is covering the electrode 24), the first magnetic component 36 may interact with the second magnetic component 38 to maintain the magnetic interaction between the first magnetic component 36 and the second magnetic component 38. It can be appreciated that the magnetic interaction between the first magnetic component 36 and the second magnetic component 38 may maintain the shroud 20 in the first position. In some examples described herein, the term "maintain" as it relates to magnetic interactions (e.g., connections, engagement) described herein, may include instances in which a pair of magnetic components interact with one another for an indefinite length of time (e.g., long term engagement), in addition to instances in which a pair of magnetic components interact with one another for a limited period of time. Further, in some instances a pair of magnetic components may interact with one another until a user moves them into a different position.

FIG. 3 further illustrates that the electrosurgical device 10 may include a third magnetic component 40 held in a stationary position by one or more engagement features 41 located on the interior surface of the body 16. Like that described above with respect to the first magnetic component 36 and the second magnetic component 38, the second magnetic component 38 may interact with the third magnetic component 40 to maintain a magnetic connection between the second magnetic component 38 and the third magnetic component 40 to maintain the shroud 20 in the second position. For example, actuating the sliding cover 18 in a distal-to-proximal direction will shift the shaft 30 distal-to-proximal direction which may disengage the second magnetic component 38 from the first magnet component 36 (because the second magnetic component 38 is fixedly attached to the shaft 30) and may also reposition the second magnetic component 38 such that it interacts with the third magnetic component 40 (this position may correspond to the position in which the shroud 20 is retracted, thereby exposing the electrode 24 as described above). Further details of the engagement of the second magnetic component 38 with the third magnetic component 40 are described below.

A described above, the first magnetic component 36 may be arranged in a distal-most position compared to the second magnetic component 38 and the third magnetic component 40. Further, the second magnetic component 38 may be arranged in an intermediate position between the first magnetic component 36 and the third magnetic component 40. Additionally, the third magnetic component may be arranged in a proximal position to both the first magnetic component 36 and the second magnetic component 38. However, this is not intended to be limiting. Rather, it is contemplated that any of the first magnetic component 36, the second magnetic component 38 and/or the third magnetic component 40 may be positioned in the distal-most, intermediate or proximal positions.

Additionally, it can be appreciated that, in some examples, the electrosurgical device 10 may only include first magnetic component 36 interacting with the second magnetic component 38 to maintain the shroud 20 in the first position, while in other examples, the electrosurgical device 10 may only include the second magnetic component 38 interacting with the third magnetic component 40 to maintain the shroud 20 in the second position. However, in yet other examples, the electrosurgical device 10 may include the first magnetic component 36, the second magnetic component 38 and the third magnetic component 40 which interact to maintain the shroud 20 in the first position or the second position.

It can be appreciated that the first magnetic component 36, the second magnetic component 38 and/or the third magnetic component 40 (or any magnetic component described herein) may be constructed from a variety of magnets and/or magnetic materials. For example, any of the magnetic components described herein (including the first magnetic component 36, the second magnetic component 38 and/or the third magnetic component 40) may be formed from a permanent magnet, a magnetic material and/or an electromagnet.

As used herein, a "permanent magnet" may include objects made from a material that is magnetized and creates its own persistent magnetic field due to its internal structure. Permanent magnets may not stop producing a magnetic field regardless of external influences. For example, the magnetic components described herein may be formed from everyday metals such as iron, nickel, cobalt, steel, stainless steel, etc.

As used herein, a "magnetic material" may include materials that can be magnetized or materials that are strongly attracted to a magnet. Examples are ferromagnetic or ferrimagnetic materials. Some examples may include materials including the elements iron, nickel and cobalt and their alloys, some alloys of rare-earth metals, and some naturally occurring minerals such as lodestone, and the like.

As used herein, an "electromagnet" may include a type of magnet in which the magnetic field is produced by an electric current. Electromagnets commonly include a wire wound into a coil, whereby the coil defines a hole (e.g., aperture) positioned generally in the central region of the coil. A current passing through the wire creates a magnetic field which is concentrated in the hole. Accordingly, the magnetic field disappears when the current is turned off. In some instances, the wire is often wound around a magnetic core made from a ferromagnetic or ferrimagnetic material, whereby the magnetic core concentrates the magnetic flux and makes a more powerful magnet. In some cases, the coil and the magnetic core are positionally fixed relative to one another. In other arrangements, such as in an electromechanical solenoid, the coil and the magnetic core are not positionally fixed—but rather the magnetic core may move within the coil.

Figure 4:
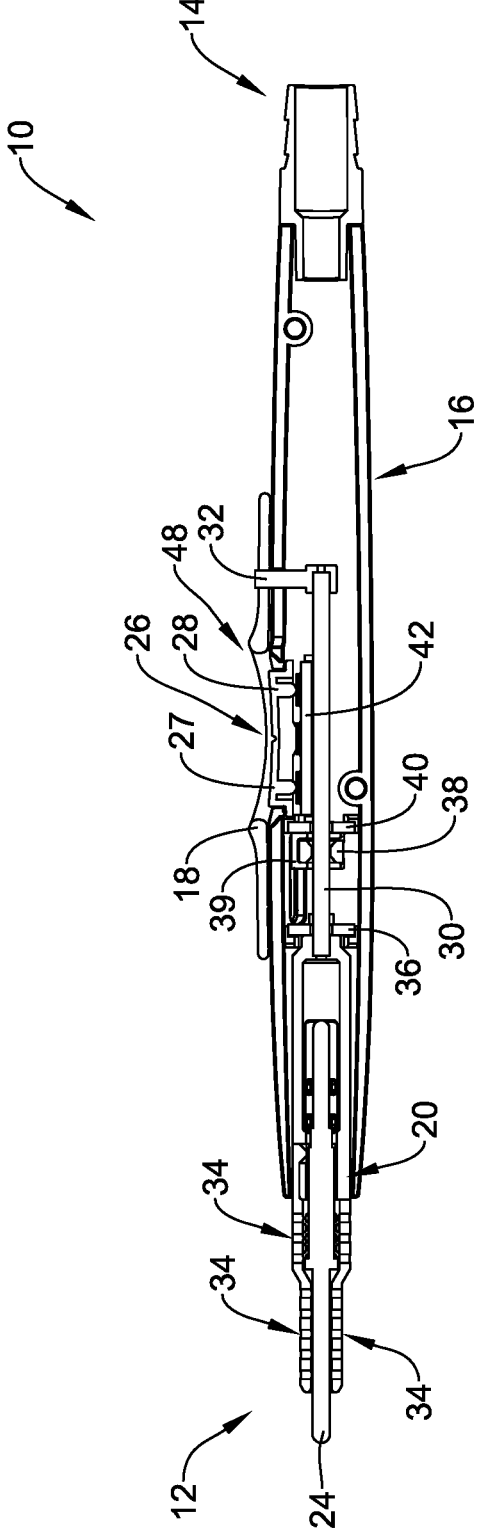
FIG. 4 illustrates a cross-sectional side view of the example electrosurgical device shown in FIG. 2.

FIG. 4 illustrates a cross-sectional side view of the electrosurgical device 10 shown in FIG. 2. Specifically, FIG. 4 illustrates the electrosurgical device 10 whereby the sliding cover 18 has been actuated in a distal-to-proximal direction relative to the body 16. As described above, this configuration may be referred to a second position in which the shroud 20 has been retracted coincident with the distal-to-proximal sliding of the sliding cover 18. Additionally, as discussed above, in order to slide the sliding cover 18 in a distal-to-proximal direction, a user must overcome the magnetic force generated by the interaction of the first magnetic component 36 with the second magnetic component 38 (the first magnetic component 36 interacts with the second magnetic component 38 when the shroud 20 is covering the electrode 24 in the first position).

When the magnetic force between the first magnetic component 36 and the second magnetic component 38 is overcome, a user may slide the sliding cover 18 distally to a second position in which the second magnetic component 38 interacts with the third magnetic component 40. In this position, the shroud 20 is maintained in a retracted position (exposing the electrode 24) until the user opts to shift the sliding cover 18 (and, consequently, the shroud 20) in a proximal-to-distal direction to cover the electrode 24. It can be appreciated that to shift the sliding cover 18 in a proximal-to-distal direction, a user must overcome the attractive force of the second magnetic component 38 with the third magnetic component 40.

FIG. 4 further illustrates that when the sliding cover 18 is actuated in a distal-to-proximal direction, the sliding cover 18 may be positioned such that the switch 26 aligns with an aperture 48 (see FIG. 5 for a clear depiction of the aperture 48) located in the sliding cover 18. This alignment permits a first power button 27 and a second power button 28 of the switch to be fully accessed and actuated by the user.

As described above, the electrosurgical device 10 may function to both cut and coagulate tissue. The process of cutting tissue, however, may require different energy be delivered to the electrode 24 as compared to the energy required to coagulate tissue. Accordingly, the first power button 27 and the second power button 28 of the switch 26 may engage a circuit board 42, which may actuate and/or send a signal to the electrosurgical system corresponding to the appropriate profile of energy to be supplied to the electrode 24 depending whether a cutting process or coagulation process is desired.

For example, the electrosurgical device 10 may be designed such that actuation of the first power button 27 may be configured to provide a different energy profile to the electrode 24 compared to the energy provided by actuation of the second power button 28. Accordingly, the user may utilize the first power button 27 to "cut" tissue. Alternatively, a user may depress the second power button 28 to "cauterize" tissue, whereby a different energy profile (as compared with depressing the first power button 27) may be supplied to the electrode 24. In some instances, the different profiles of energy delivered to the electrode may include applying different waveforms to the electrode. Further, applying different waveforms may include applying different peak voltages to the electrode, whereby the different peak voltages may correspond to a "cut" mode versus a "coagulation" mode, respectively. Additionally, an electrosurgical generator coupled to the medical device 10 may include one or more controls which permit a user to adjust the "cut" waveform and/or the "coagulation" waveform.

While the above discussion describes the first power button 27 as suppling one profile of energy relative to the second power button 28, a reverse configuration is also contemplated (e.g., the first power button 27 is used to coagulate tissue while the second power button 28 is used to cut tissue).

FIG. 5 illustrates an exploded view of the electrosurgical device shown in FIG. 1. FIG. 5 illustrates the body 16 may be formed from a first body component 17a and a second body component 17b attached together in a clamshell configuration (in some examples, the first body component 17a may be snapped together with the second body component 17b to form the body 16). Additionally, FIG. 5 illustrates the shroud 20, including the plurality of apertures 34 disposed around its distal end region. In some examples, the plurality of apertures 34 may extend around the entire circumference of the shroud 20. In other examples, the plurality of apertures 34 may be selectively positioned along the shroud 20 in any pattern or arrangement.

FIG. 5 further illustrates the electrode 24 and the proximal connector 22, both of which engage and remain in a fixed position relative to the body 16, as described above. Additionally, FIG. 5 illustrates the sliding cover 18 including the aperture 48 (through which a user may access the first power button 27 and the second power button 28 of the switch 26).

The first power button 27 and the second power button 28 may engage the circuit board 42 to control the profile of energy provided to the electrode 24 to cut or coagulate tissue.

As described above, the sliding over 18 may attach to the shroud 20 via the linkage 32 and the shaft 30. Further, FIG. 5 illustrates the aperture 46 located in the body 16 through which the linkage 32 extends. The aperture 46 extends longitudinally along the body 16 which allows the linkage 32 to translate along the body 16 as the sliding cover 18 is translated along the body 16. FIG. 5 further illustrates that, in some examples, the linkage 32 may include an aperture 49 designed to accept the proximal end of the shaft 30.

FIG. 5 further illustrates the shaft 30 extending through an aperture in the first magnetic component 36 and an aperture in the third magnetic component 40. As discussed above, the first magnetic component 36 and the third magnetic component 40 may be held in a fixed position relative to the body 16. Further, the second magnetic component 38 may be supported by the housing 39, whereby the housing 39 may be fixedly attached to the shaft 30. Therefore, actuation of the slider cover 18 may not only actuate the shroud 20 between a first position (in which it covers the electrode 24) and a second position (in which it exposes the electrode 24), but may also engage the second magnetic component 38 with the first magnetic component 36 (when the shroud 20 is in the first position) and the also engage the second magnetic component 38 with the third magnetic component 40 (when the shroud 20 is in the second position).

Additionally, FIG. 5 illustrates that the housing 39 may include one or more projections 43 which extend through corresponding apertures 44 in the body 16 (it is noted that only a single aperture 44 is visible in FIG. 5, the other aperture 44 is located on the other side of the body 16 in FIG. 5). Like the aperture 46, each of the apertures 44 may extend longitudinally along the body 16, thereby permitting the housing 39 to translate along the body 16 as the slider cover 18 is translated along the body.

Additionally, it is contemplated that the first magnetic component 36, the second magnetic component 38 and the third magnetic component 40 described above may all include permanent magnets (a schematic illustration of this configuration will be described below with respect to FIGS. 7A and 7B). Additionally, it is contemplated that, in some instances, the second magnetic component 38 may include a magnetic material, while the first magnetic component 36 and the third magnetic component 40 may include a permanent magnet (a schematic illustration of this configuration will be described below with respect to FIG. 8). Additionally, it is contemplated that, in some instances, the second magnetic component 38 may include a permanent magnet, while the first magnetic component 36 and the third magnetic component 40 may include a magnetic material. Additionally, it is contemplated that the first magnetic component 36, the second magnetic component 38 and/or the third magnetic component 40 may include a magnetic material and/or a permanent magnet in any combination or arrangement.

Figure 6:
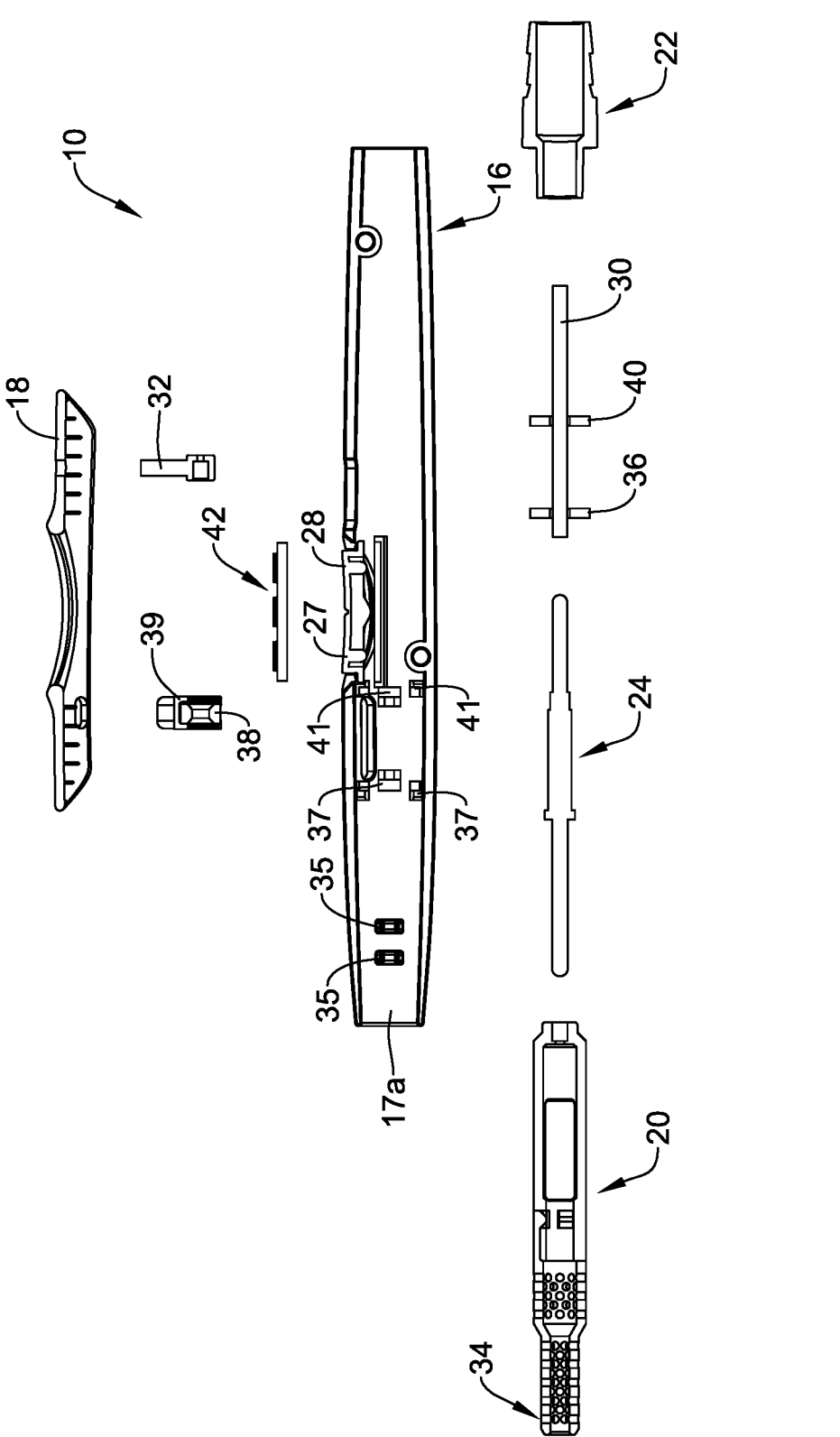
FIG. 6 illustrates a cross-sectional side view of the electrosurgical device shown in FIG. 1.

FIG. 6 illustrates a cross-sectional side view of the electrosurgical device 10 shown in FIG. 1. However, it can be appreciated that the second body component 17b has been removed from the body 16 to reveal the interior surface of the first body component 17a. Accordingly, FIG. 6 illustrates that the first body component 17a and/or the second body component 17b may include one or more structures which are designed to receive, engage and/or hold one or more of the components of the electrosurgical device

10. For example, the interior surface of the first body component 17a (e.g., the interior surface of any component defining the body 16) may include one or more structures 35/37/41 (e.g., molded features) which hold the electrode 24, the first magnet component 36 and/or the third magnet component 40 stationary to the body 16. The features may also hold the circuit board 42 in place relative to the body 16. The features may also provide tracks, rails, alignment features etc. which align the shroud 20 with the shaft 30, thereby assuring that the shroud 20 and the shaft 30 remain aligned when the shaft 30 is translated to expose the electrode 24.

Figure 7A:
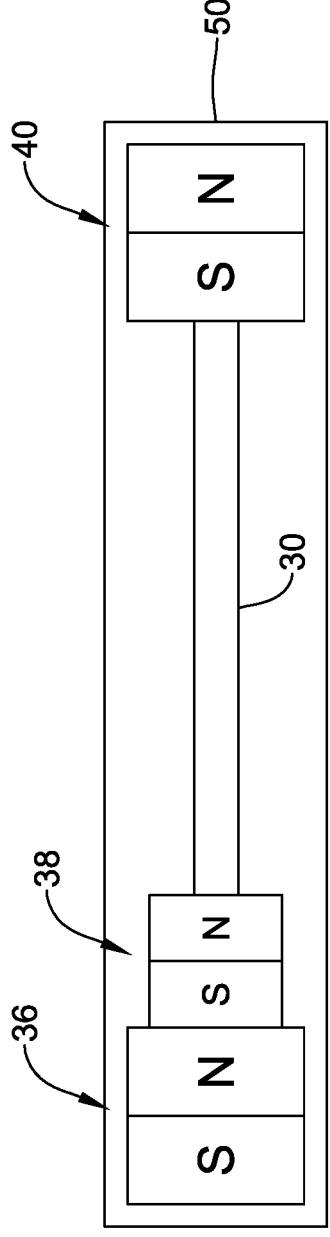
FIG. 7A is a schematic illustration showing an example embodiment shown in first position.

FIG. 7A is a schematic illustration representing one example configuration of the magnetic assembly (including the first magnetic component 36, the second magnetic component 38 and the third magnetic component 40) described above with respect to FIGS. 1-6. As shown in the first illustration 50 of FIG. 7A, each of the first magnetic component 36, the second magnetic component 38 and the third magnetic component 40 may include permanent magnets, whereby each permanent magnet includes a "north" and "south" polarity (the polarity of each of the first magnetic component 36, the second magnetic component 38 and the third magnetic component 40 is defined within the illustration 50 in FIG. 7A). It can be appreciated that the example magnetic polarities defined in FIG. 7A, FIG. 7B and FIG. 8 are not intended to be limiting. For example, it can be appreciated that if each of the "north" and "south" magnetic polarities illustrated in FIG. 7A were reversed, the electrosurgical device 10 may operate identically to that described with respect to FIG. 7A.

Additionally, the schematic illustration 50 of FIG. 7A shows the second magnetic component 38 attached to the shaft 30, as described above (for simplicity, the housing 39, shroud 20 and electrode 24 are not depicted in FIG. 7A). Further, the illustration 50 shows the south pole of the second magnetic component 38 attracted to the north pole of the first magnetic component 36. The attractive force between the first magnetic component 36 and the second magnetic component 38 may maintain the shroud 20 in this position (e.g., covering the electrode 24) until the attractive force is overcome via a user translating the slider cover 18 in a distal-to-proximal direction.

Figure 7B:
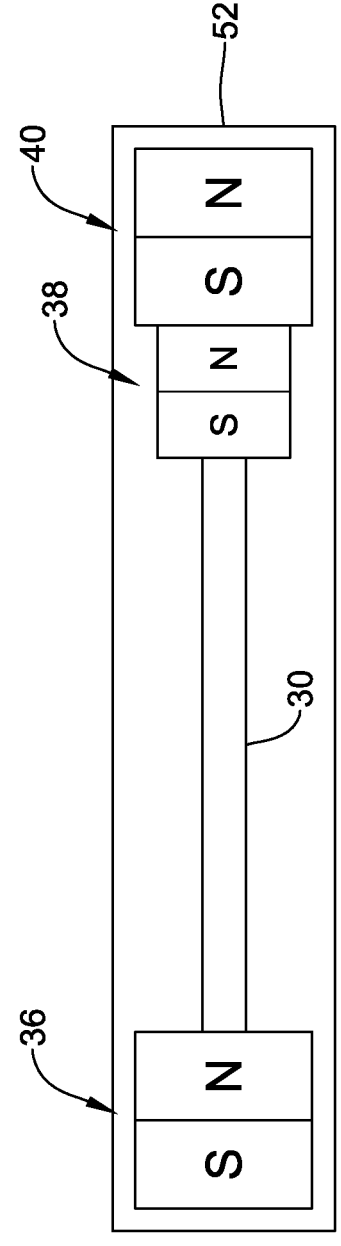
FIG. 7B is a schematic illustration showing an example embodiment shown in second position.
Figure 8:
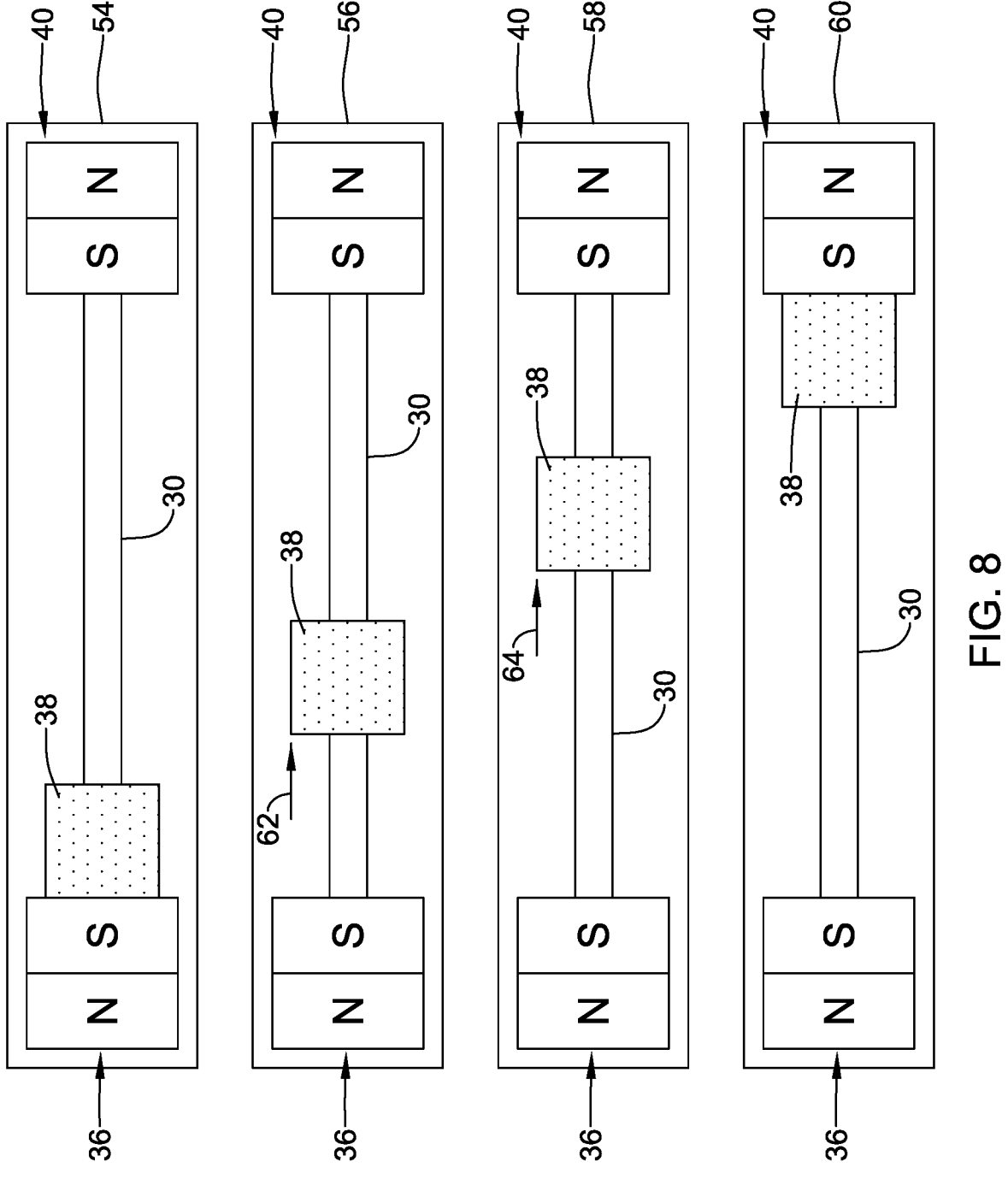
FIG. 8 is a series of schematic illustrations showing an electrosurgical device shifting between a first position and a second position.

For example, the second schematic illustration 52 of FIG. 7B shows the second magnetic component 38 after having been pulled away from the first magnetic component 36 and translated toward the third magnetic component 40. FIG. 7B illustrates that as the second magnetic component 38 moves farther away from the first magnetic component 36, the attractive force between the first magnetic component 36 and the second magnetic component 38 decreases, while the attractive force between the north pole of the second magnetic component 38 and the south pole of the third magnetic component 40 increases to draw the second magnetic component 38 into engagement with the third magnetic component 40. The attractive force between the second magnetic component 38 and the third magnetic component 40 may maintain the shroud 20 in the second position (e.g., exposing the electrode 24) until the attractive force is overcome via a user translating the slider cover 18 in a proximal-to-distal direction.

FIG. 8 is a schematic illustration representing another example magnetic assembly (including the first magnetic component 36, the second magnetic component 38 and the third magnetic component 40) described above with respect to FIGS. 1-7. As shown in the first illustration 54 of FIG. 8, in some examples, each of the first magnetic component 36 and the third magnetic component 40 may include permanent magnets, whereby each permanent magnet includes a "north" and "south" polarity (the polarity of each of the first magnetic component 36 and the third magnetic component 40 is defined within each illustration 52/54/56/58 in FIG. 8). However, in contrast to the example described above with respect to FIGS. 7A-7B, the second magnetic component 38 may include a magnetic material.

The first schematic illustration 54 of FIG. 8 shows the second magnetic component 38 attached to the shaft 30, as described above (for simplicity, the housing 39, the shroud 20 and the electrode 24 are not depicted in FIG. 8). Further, the illustration 54 shows the second magnetic component 38 attracted to the south pole of the first magnetic component 36. The attractive force between the first magnetic component 36 and the second magnetic component 38 may maintain the shroud 20 in the first position (e.g., covering the electrode 24) until the attractive force between the first magnetic component 36 and the second magnetic component 38 is overcome via a user translating the slider cover 18 in a distal-to-proximal direction.

For example, the second schematic illustration 56 of FIG. 8 shows the second magnetic component 38 after having been pulled away from the first magnetic component 36 and shifted toward the third magnetic component 40. The distal-to-proximal translation of the second magnetic component 38 is depicted by the arrow 62 in the second schematic illustration 56. It can be appreciated that as the second magnetic component 38 moves away from the first magnetic component 36, the attractive force between the first magnetic component 36 and the second magnetic component 38 decreases until the attractive force placed upon the second magnetic component 38 from the first magnetic component 36 and the third magnetic component 40 are approximately equal.

However, the third schematic illustration 58 of FIG. 8 shows the second magnetic component 38 after having been pulled in a distal-to-proximal direction such that the second magnetic component 38 is closer to the third magnetic component 40. The distal-to-proximal movement of the second magnetic component 38 is depicted by the arrow 64 in the third schematic illustration 58 of FIG. 8. It can be appreciated that as the second magnetic component 38 moves away from the first magnetic component 36, the attractive force between the first magnetic component 36 and the second magnetic component 38 decreases. If can be further appreciated that that as the second magnetic component 38 moves closer toward the third magnetic component 40, the attractive force between the second magnetic component 38 and the third magnetic component 40 increases.

The fourth schematic illustration of FIG. 8 shows the second magnetic component 38 shifted in a distal-to-proximal direction to a position in which the second magnetic component 38 has engaged the south pole of the third magnetic component 40. The attractive force between the second magnetic component 38 and the third magnetic component 40 may maintain the shroud 20 in the second position (e.g., exposing the electrode 24) until the attractive force is overcome via a user translating the slider cover 18 in a proximal-to-distal direction.

Figure 9:
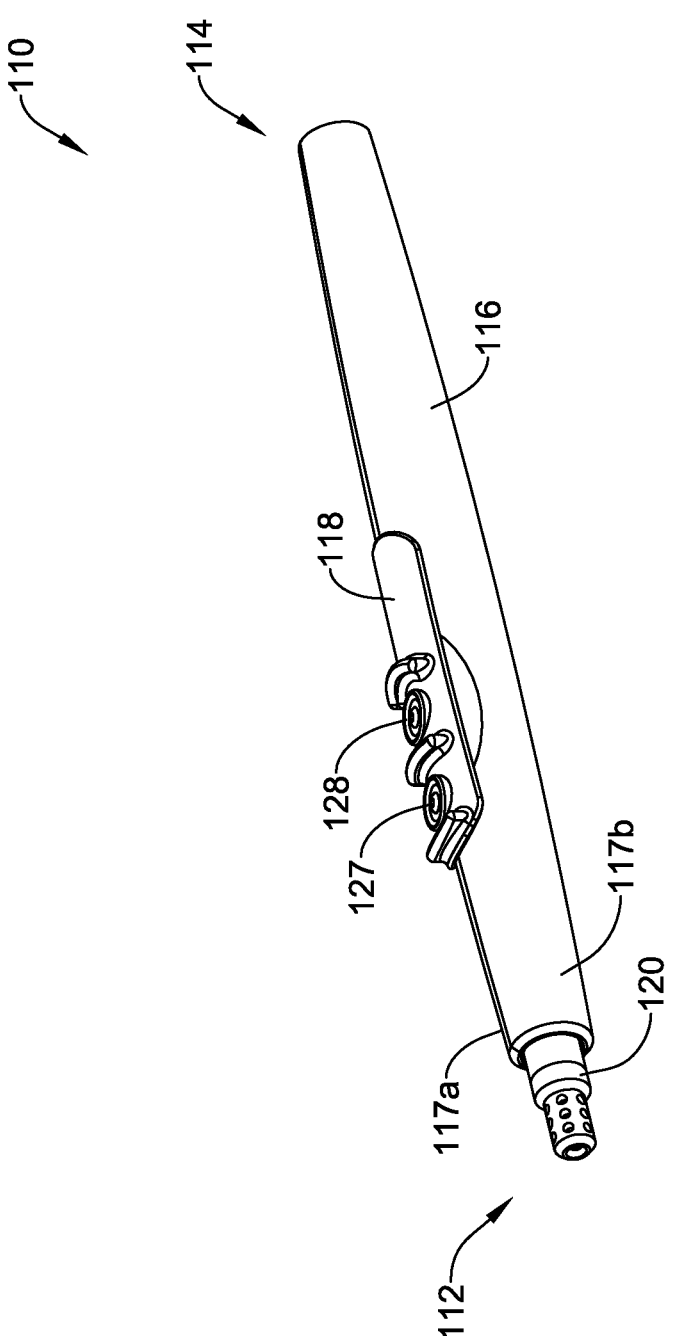
FIG. 9 illustrates another example electrosurgical device in a first position.
Figure 10:
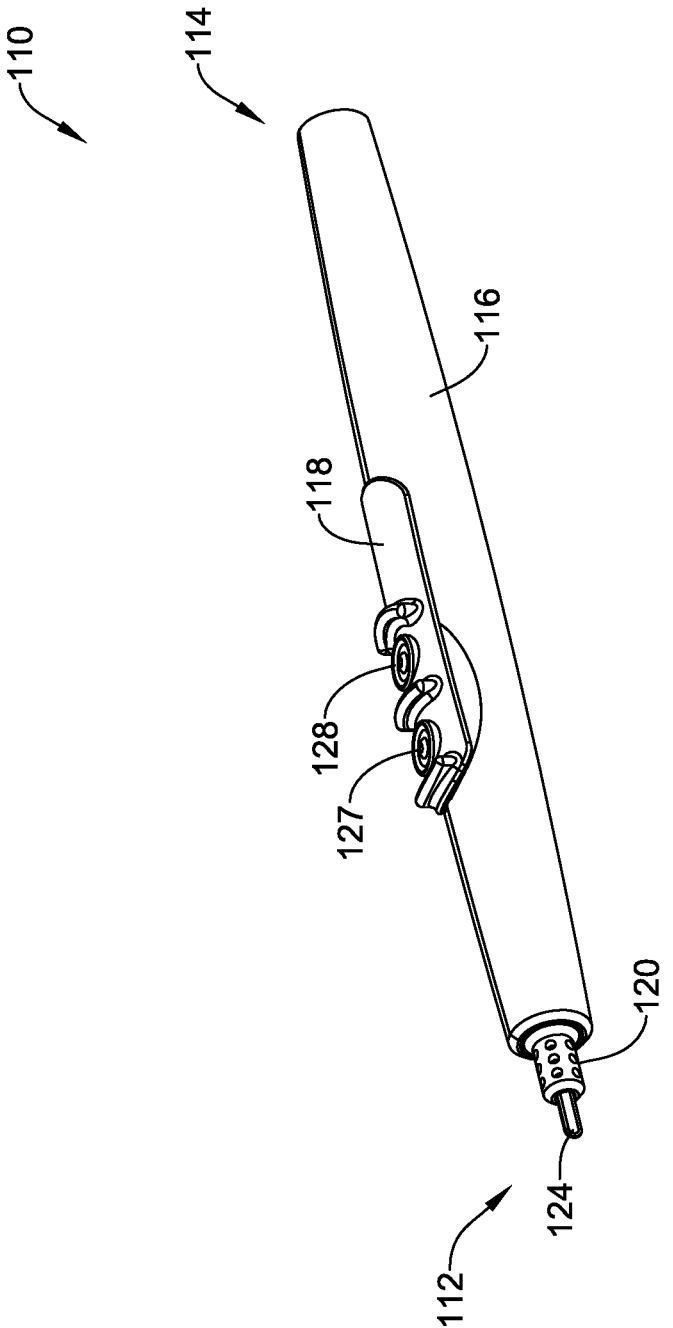
FIG. 10 illustrates the example electrosurgical device shown in FIG. 9 in a second position.

FIG. 9 illustrates another example electrosurgical device 110. The electrosurgical device 110 may be similar in form and function to the electrosurgical device 10 described above. For example, FIG. 10 illustrates that the electrosurgical device 110 may include an actuating shroud 120 positioned along a distal end region 112 of a body 116. FIG.

9 illustrates the body 116 may be formed from a first body component 117a and a second body component 117b attached together in a clamshell configuration (in some examples, the first body component 117a may be snapped together with the second body component 117b to form the body 116).

Additionally, FIG. 9 illustrates that the electrosurgical device 110 may include a sliding cover 118 designed to slide along the body 116. Like that described above with respect to the sliding cover 18, actuation of the sliding cover 118 along the body 116 in a distal-to-proximal direction actuate the shroud 120 to a position in which an electrode 124 (e.g., shown in FIG. 10) is exposed. For example, FIG. 10 illustrates the electrosurgical device of FIG. 9 whereby the sliding cover 118 has been manipulated by a user to actuate (e.g., retract, shift, translate, move, etc.) the shroud 120 in a distal-to-proximal direction (e.g., the shroud 120 retracts along the body 116 from the distal end region 112 toward the proximal end region 114 of the electrosurgical device 110) to expose the electrode 124. It can be appreciated that the electrode 124 may remain in a fixed position relative to the body 116, while the shroud 120 actuates relative to both the electrode 124 and the body 116.

FIG. 9 further illustrates that the electrosurgical device 110 may be designed to include a first power button 127 and a second power button 128 integrated into the sliding cover 118. In some examples, the first power button 127 and/or the second power button 128 may be referred to as an activation button. Additionally, the sliding cover 118 may be molded to include the first power button 127 and the second power button 128, whereby each of the first power button 127 and the second power button 128 may be depressed and engage one or more additional components of the electrosurgical device 110. It can be appreciated that the first power button 127 and the second power button 128 may translate relative to the body 116 as the sliding cover 118 translates along the body 116.

Figure 11:
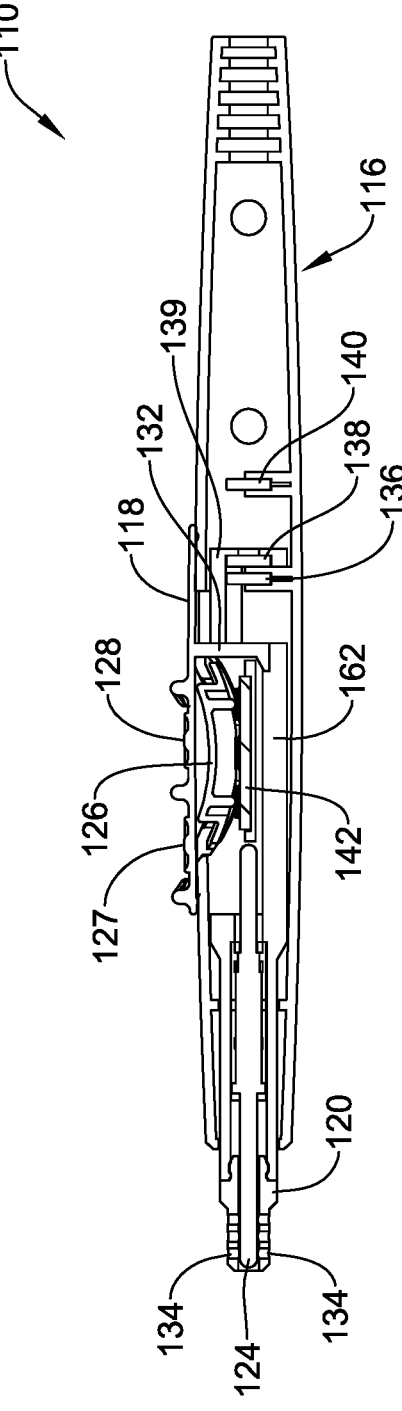
FIG. 11 illustrates a cross-sectional side view of the example electrosurgical device shown in FIG. 9.

FIG. 11 illustrates a cross-sectional side view of the electrosurgical device 110 shown in FIG. 9. For example, FIG. 11 illustrates the shroud 120 in a first position (e.g., in a distal-most position relative to the body 116) in which it is covering the electrode 124. Additionally, it can be appreciated that the body 116 may include one or more structures which are designed to receive, engage and/or hold one or more of the components of the electrosurgical device 110. For example, the interior surface of the body 116 (e.g., the interior surface of any component defining the body 116) may include one or more structures (e.g., molded features) which hold the electrode 124 in a fixed position relative to the body 116. The features may also hold a switch 126, a circuit board 142, a first magnetic component 136 and/or a third magnetic component 140 in a fixed position relative to each other and the body 116.

Figure 12:
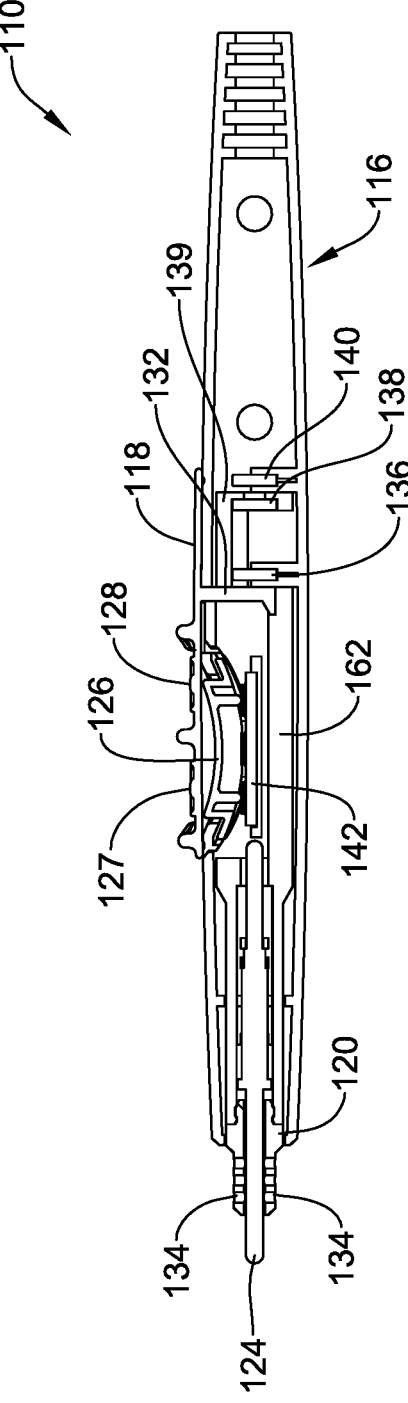
FIG. 12 illustrates a cross-sectional side view of the example electrosurgical device shown in FIG. 10.

Like the electrosurgical device 10 described above, the electrosurgical device 110 may be designed such that actuation (e.g., sliding, etc.) of the sliding cover 118 may simultaneously actuate the shroud 120. For example, actuation of the sliding cover 118 in a distal-to-proximal direction may actuate the shroud 120 in a distal-to-proximal direction, while actuation of the sliding cover 118 in a proximal-to-distal direction may actuate the shroud 120 in a proximal-to-distal direction. The simultaneous actuation of the sliding cover 118 and the shroud 120 occurs because the sliding cover 118 and the shroud 120 are attached to one another via a linkage 162. Specifically, FIG. 12 illustrates that the proximal end of the shroud 120 may be connected to a portion of the linkage 162 (e.g., a distal end portion of the linkage), which extends through an inner cavity of the body 116. It is also contemplated that, in some examples, the proximal end of the shroud 120 may take the place of the linkage 162. In other words, in some examples, the linkage 162 would not be a separate component, but would be replaced by an extended proximal end region of the shroud 120. Further, FIG. 12 illustrates that the sliding cover 118 may include a stem 132 which extends into the inner cavity of the body 116 and attaches to a distal end of the linkage 162. Accordingly, it can be appreciated that translating the sliding cover 118 along the body 116 may cause the shroud 120 to simultaneously translate relative to the body 116 and the electrode 124

Additionally, FIG. 11 illustrates that the sliding cover 118 may be molded to include the first power button 127 and the second power button 128, whereby each of the first power button 127 and the second power button 128 may be depressed and engage one or more additional components of the electrosurgical device 110. It can be appreciated that the first power button 127 and the second power button 128 may translate relative to the body 116 as the sliding cover 118 translates along the body 116.

FIG. 11 further illustrates that, in some examples, the linkage 162 (or the proximal end region of the shroud 120) may not necessarily be aligned along a central longitudinal axis of the body 116 (in contrast to the shaft 30 described above with respect to the electrosurgical device 10, which is generally aligned with the central longitudinal axis of the body 16). In other words, the linkage 162 may be vertically offset from the central longitudinal axis of the body 116. FIG. 11 illustrates that the linkage 162 may be attached to the shroud 120 along a generally bottom portion of the shroud 120 and may pass underneath the circuit board 142.

Further, the circuit board 142 shown in FIG. 11 may be attached to one or more wires which may also be attached to the electrode 124. As discussed above, the wires may be attached to an energy supply (e.g., an electrosurgical generator of an electrosurgical system) and transfer electrical energy from the electrosurgical generator to energize the electrode 124.

Additionally, FIG. 11 illustrates that that the electrosurgical device 110 may include a switch 126 positioned above the circuit board 142 and underneath the sliding cover 118. The upper portion of the switch 126 may be spaced away from the sliding cover 118 such that the sliding cover 118 may pass (e.g., slide) along the switch 126. FIG. 12 further illustrates that when the shroud 120 is positioned in a distalmost position relative to the body 116 (thereby covering the electrode 124), the first power button 127 and the second power button 128 may be misaligned (e.g., longitudinally offset) from the switch 126. It can be appreciated that when the first power button 127 and the second power button 128 are misaligned with the switch 126, neither the first power button 127 nor the second power button 128 may engage the switch 126 and/or the circuit board 142. In other words, when the first power button 127 and the second power button 128 are misaligned from the switch 126, depressing the first power button 127 or the second power button 128 will not trigger the circuit board 142 to permit energy to flow from the electrosurgical generator to the electrode 124.

FIG. 11 further illustrates that the electrosurgical device 110 may include a magnetic assembly which may maintain the shroud 120 in given position (e.g., covering or exposing the electrode 124) until the user opts to translate the shroud 120 to an alternative position (e.g., covering or exposing the electrode 124).

Like the magnetic assembly described above with respect to the electrosurgical device 10, the magnetic assembly shown in FIG. 11 may include a first magnetic component 136 held in a stationary position via one or more engagement features located on the interior surface of the body 116. Additionally, the magnetic assembly may include a second magnetic component 138 which may be attached to and supported by a housing 139. Additionally, the housing 139 may be attached to the projection 132 extending radially inward from the sliding cover 118. Accordingly, it can be appreciated that translation of the sliding cover 118 may simultaneously translate the second magnetic component 138 via translation of the housing 139. FIG. 11 further illustrates that the electrosurgical device 110 may include a third magnetic component 140 which may be held in a stationary position by one or more engagement features located on the interior surface of the body 116.

It can be appreciated that, when in the position shown in FIG. 11 (e.g., the first position in which the shroud 120 is covering the electrode 124), the first magnetic component 136 may magnetically interact with the second magnetic component 138 to maintain the shroud 120 in the first position until a user slides the sliding cover 118 in a distal-to-proximal direction, thereby pulling the second magnetic component 138 away from the first magnetic component 136.

FIG. 12 illustrates a cross-sectional side view of the electrosurgical device 110 shown in FIG. 11, whereby the electrosurgical device 110 is in a second position whereby the sliding cover 118 and the shroud 120 have been retracted proximally to expose the electrode 124. Additionally, FIG. 12 further illustrates that when the sliding cover 118 is slid in a distal-to-proximal direction, the second magnetic component 138 is simultaneously pulled away from the first magnetic component 136 and interacts with the third magnetic component 140 to maintain a magnetic connection between the second magnetic component 138 and the third magnetic component 140. The magnetic interaction between the second magnetic component 138 and the third magnetic component 140 may maintain the shroud 120 in the second position. In other words, shifting the sliding cover 118 in a distal-to-proximal direction may shift the housing 139 in a distal-to-proximal direction which may disengage the second magnetic component 138 from the first magnetic component 136 (because the second magnetic component 138 is fixedly attached to the housing 139) and may also reposition the second magnetic component 138 such that it interacts with the third magnetic component 140 (this may correspond to the position in which the shroud 120 is retracted, thereby exposing the electrode 124, as described above). Unlike the design of the magnetic assembly of the electrosurgical device 10 described above, FIGS. 11-12 illustrate that the second magnetic component 138 may not need to be attached to a shaft (or any other structure) which is aligned coaxially with the center of the first magnetic component 136 and/or the third magnetic component 140. Rather, the engagement of the second magnetic component 138 with the first magnetic component 136 and/or the third magnetic component 140 may be accomplished using a variety of structural configurations as long as the second magnetic component 138 can translate between the first magnetic component 136 and the third magnetic component 140. For example, in the electrosurgical device 110, the housing 139 is offset from the central longitudinal axis of the second magnetic component 138, yet the second magnetic component 138 remains positioned between the first magnetic component 136 and the third magnetic component 140, thereby permitting the second magnetic component 138 to translate between the first magnetic component 136 and/or the third magnetic component 140, as described herein.

FIG. 12 further illustrates that when the first power button 127 and the second power button 128 are aligned with the switch 126 (and the circuit board 142), depressing either the first power button 127 or the second power button 128 may engage the switch 126. Further, a bottom portion of the switch 126 may include one or more projections which are designed to engage the circuit board 142 when either the first power button 127 or the second power button 128 is depressed. In other words, when either the first power button 127 or the second power button 128 is depressed, a portion of the switch 126 which is aligned with the first power button 127 or the second power button 128 engages a portion of the circuit board 142 which is aligned with either the first power button 127 or the second power button 128, respectively.

Further, the circuit board 142 controls how much power is delivered to the electrode 124 (as described above). As described above, the electrosurgical device 110 may be to designed such that the first power button 127 may be actuated to cut tissue, while the second power button 128 may be actuated to coagulate tissue. Therefore, the circuit board 142 may control the profile of energy delivered to the electrode 124 depending on whether the first power button 127 is depressed versus if the second power button 128 is depressed. In some instances, the first power button 127 may be designed to deliver more energy relative to the second power button 128, whereby the first button 127 is utilized to cut tissue and the second power button is utilized to coagulate tissue. However, it is also contemplated the first power button 127 may be designed to deliver a different profile of energy relative to the second power button 128, whereby the first button 127 is utilized to coagulate tissue and the second power button is utilized to cut tissue.

Figure 13:
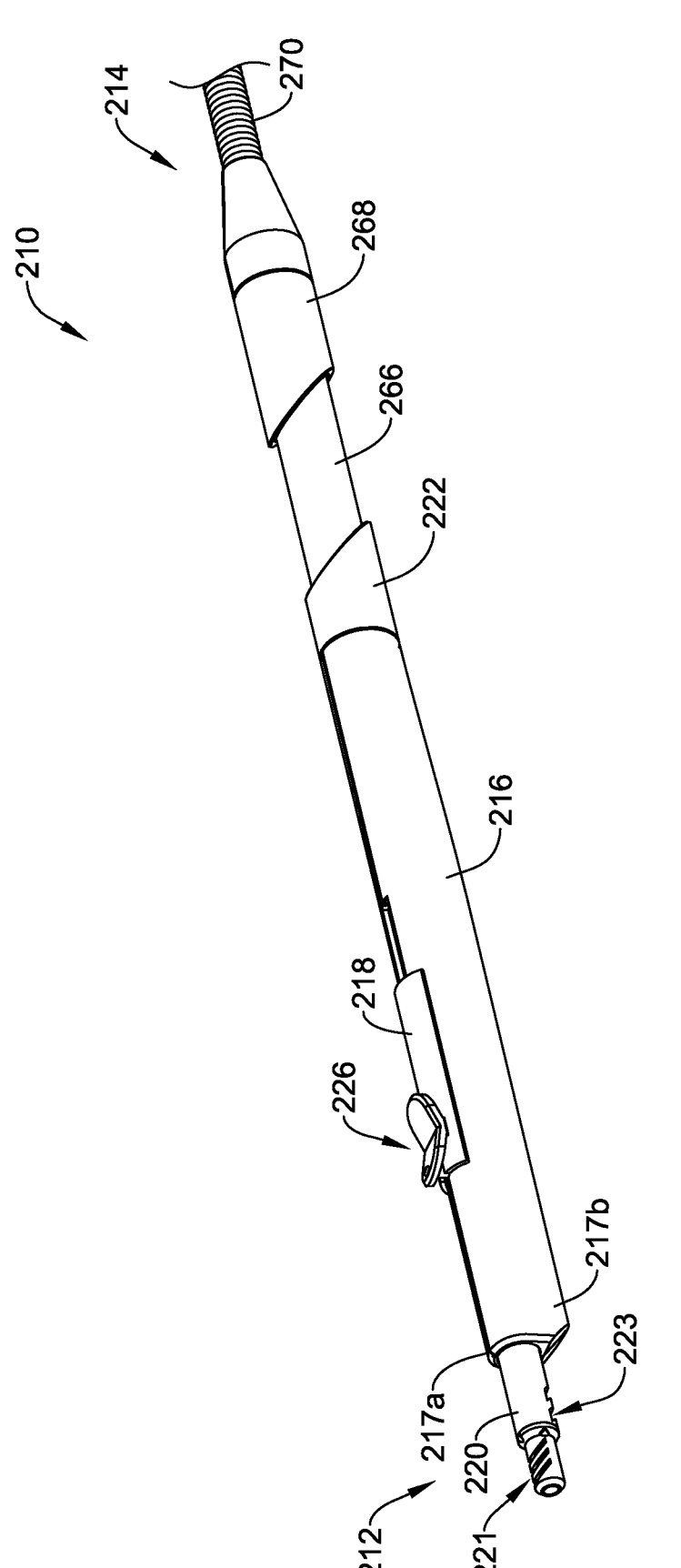
FIG. 13 illustrates another example electrosurgical device in a first position.

FIG. 13 illustrates another example electrosurgical device 210. The electrosurgical device 210 may be similar in form and function to other electrosurgical devices described above. For example, FIG. 13 illustrates that the electrosurgical device 210 may include an actuating shroud 220 positioned along a distal end region 212 of a body 216. FIG. 13 further illustrates the body 216 may be formed from a first body component 217a and a second body component 217b attached together in a clamshell configuration (in some examples, the first body component 217a may be snapped together with the second boy component 217b to form the body 216).

Figure 14:
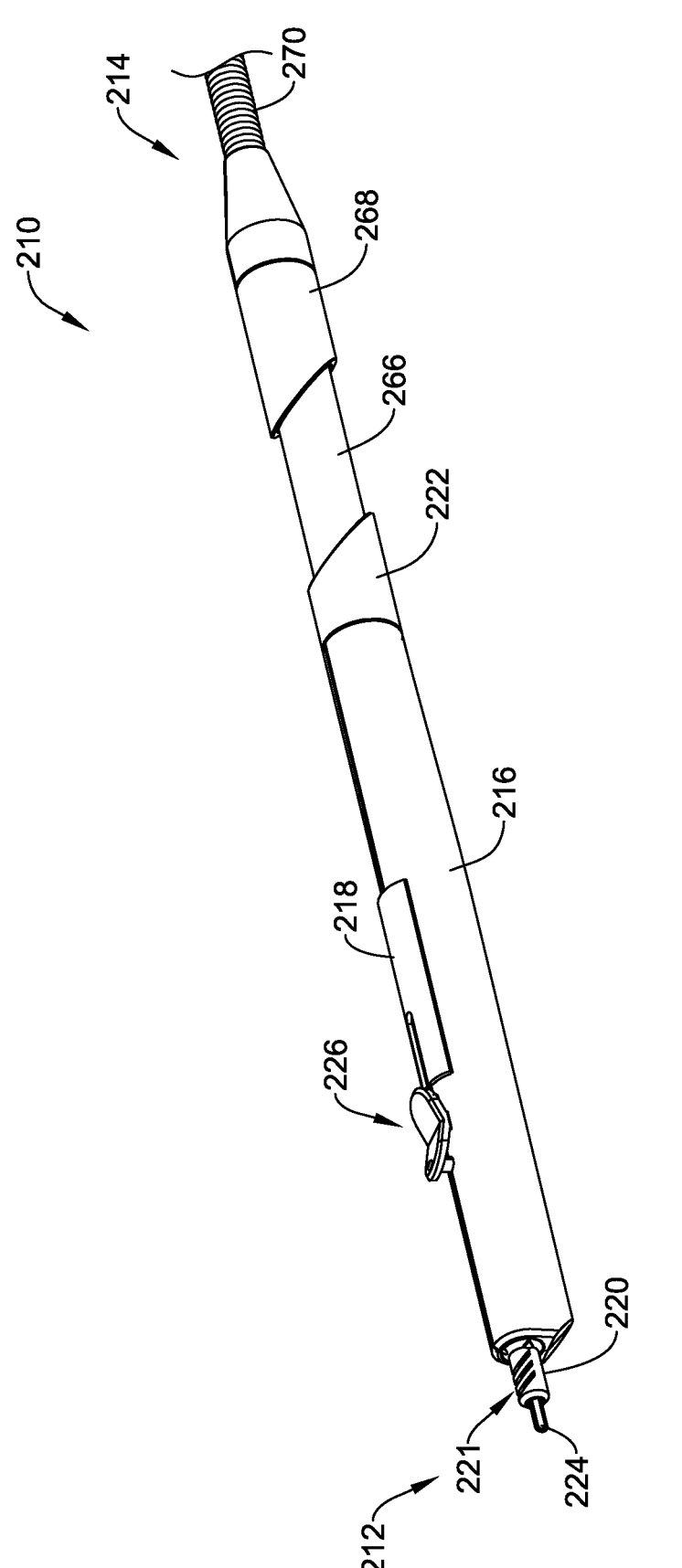
FIG. 14 illustrates the example electrosurgical device shown in FIG. 13 in a second position.

Additionally, FIG. 13 illustrates that the electrosurgical device 210 may include a lock-out cover 218 designed to slide along the body 216. Actuation of the lock-out cover 218 along the body 116 in a distal-to-proximal direction may actuate the shroud 220 to a position in which an electrode 224 (not visible in FIG. 13 but shown in FIG. 14) is exposed. For example, FIG. 14 illustrates the electrosurgical device of FIG. 13 whereby the lock-out cover 218 has been manipulated by a user to translate (e.g., retract, shift, actuate, move, etc.) the shroud 220 in a distal-to-proximal direction (e.g., the shroud 220 retracts along the body 216 from the distal end region 212 toward the proximal end region 214 of the electrosurgical device 210) to expose the electrode 224. It can be appreciated that the electrode 224 may remain in a fixed position relative to the body 216, while the shroud 220 moves relative to both the stationary electrode 224 and the body 216.

FIG. 13 further illustrates that the electrosurgical device 210 may include an activation switch (e.g. activation member, toggle switch, button, etc.) 226 capable of being pivoted (e.g., toggled, rocked, etc.) either forward or backward (or depressed) to energize the electrode 224. For example, similar to the other electrosurgical devices described above, pivoting the activation switch 226 forward (or depressing the button) may provide a profile of energy to the electrode 224 to cut tissue, while pivoting the activation switch 226 backward (or depressing another button) may provide a different profile of energy (as compared to pivoting the activation switch 226 forward) to coagulate tissue. However, it is contemplated that pivoting the activation switch 226 forward may provide a profile of energy to the electrode 224 to coagulate tissue, while pivoting the activation switch 226 backward may provide a profile of energy to electrode 224 to cut tissue.

Further, FIG. 14 illustrates that the lock-out cover 218 may be utilized to prevent the activation switch 226 from pivoting forward or backward, thereby preventing power from being delivered to the electrode 224. For example, when the lock-out cover 218 is slid forward in a distal-most position (such as the configuration shown in FIG. 14) the distal end region of the lock-out cover 218 may slide underneath the activation switch 226, thereby preventing the activation switch 226 from pivoting forward or backward to power the electrode 224. In other words, sliding the lock-out cover 218 distally may sandwich the lock-out cover 218 between the activation switch 226 and the body 216, thereby preventing the activation switch 226 from being pivoted to energize the electrode 224. FIG. 14 illustrates that when the lock-out cover 218 is slid proximally, the activation switch 226 is free to pivot forward or backward and energize the electrode 224.

Additionally, while FIG. 14 illustrates an example medical device in which the lock-out cover 218 is slid in a proximal-to-distal direction to prevent the activation switch 226 from pivoting forward or backward (or depressing a button) to energize the electrode 224, this is not intended to be limiting. Rather, it can be appreciated that, in some examples, the lock-out cover 218 of the medical device 210 may be designed to slide in a distal-to-proximal direction to prevent the activation switch 226 from pivoting forward or backward to energize the electrode 224. In other words, the lock-out cover 218 may be positioned distal to activation switch 226 (versus proximal to the activation switch, as illustrated in FIG. 14), whereby the distal-to-proximal sliding of the lock-out cover 218 may position the lock-out switch 218 underneath the activation switch 226, thereby preventing the activation switch 226 from pivoting forward or backward to energize the electrode 224.

FIG. 13 further illustrates that the electrosurgical device 210 may include one or more slots 221 positioned along the upper surface of the shroud 220 and one or more slots 223 positioned along the lower surface of the shroud 220. In some examples, the slots 221 may resemble a first set of angled louvers disposed along the upper surface of the shroud 20 and the slots 223 may resemble a second set of angled louvers disposed along the lower surface of the shroud 220. Additionally, while FIG. 13 illustrates that the slots 221 and the slots 223 are positioned at an angle with respect to the longitudinal axis of the shroud 220, other configurations are contemplated. For example, the slots 221 and/or the slots 223 may be oriented such that they are generally perpendicular to the longitudinal axis of the shroud 220.

Additionally, FIG. 13 illustrates that when the shroud 220 is in a first position (whereby the electrode 224 is covered), both the slots 221 and the slots 223 are positioned outside of the body 216. However, FIG. 14 illustrates that when the shroud 220 is in a second position whereby the electrode 224 is exposed, the slots 221 are positioned outside of the body 216 while the slots 223 have been retracted into the distal end region of the shroud 220.

FIG. 13 further illustrates that the electrosurgical device 210 may include a first proximal connector 222 positioned along the proximal end region 214 of the electrosurgical device 210. Additionally, the first proximal connector 222 may be attached to a first flexible tube 266 which is also attached to a second proximal connector 268. The second proximal connector 268 may be further connected to a second flexible tube 270 which may extend away from the electrosurgical device 210 and attach to an electrosurgical system (e.g., shown in FIG. 30). A more detailed discussion of the first proximal connector 222, the first flexible tube 266, the second proximal connector 268 and the second flexible tube 270 is set forth below with respect to FIG. 16.

Figure 15:
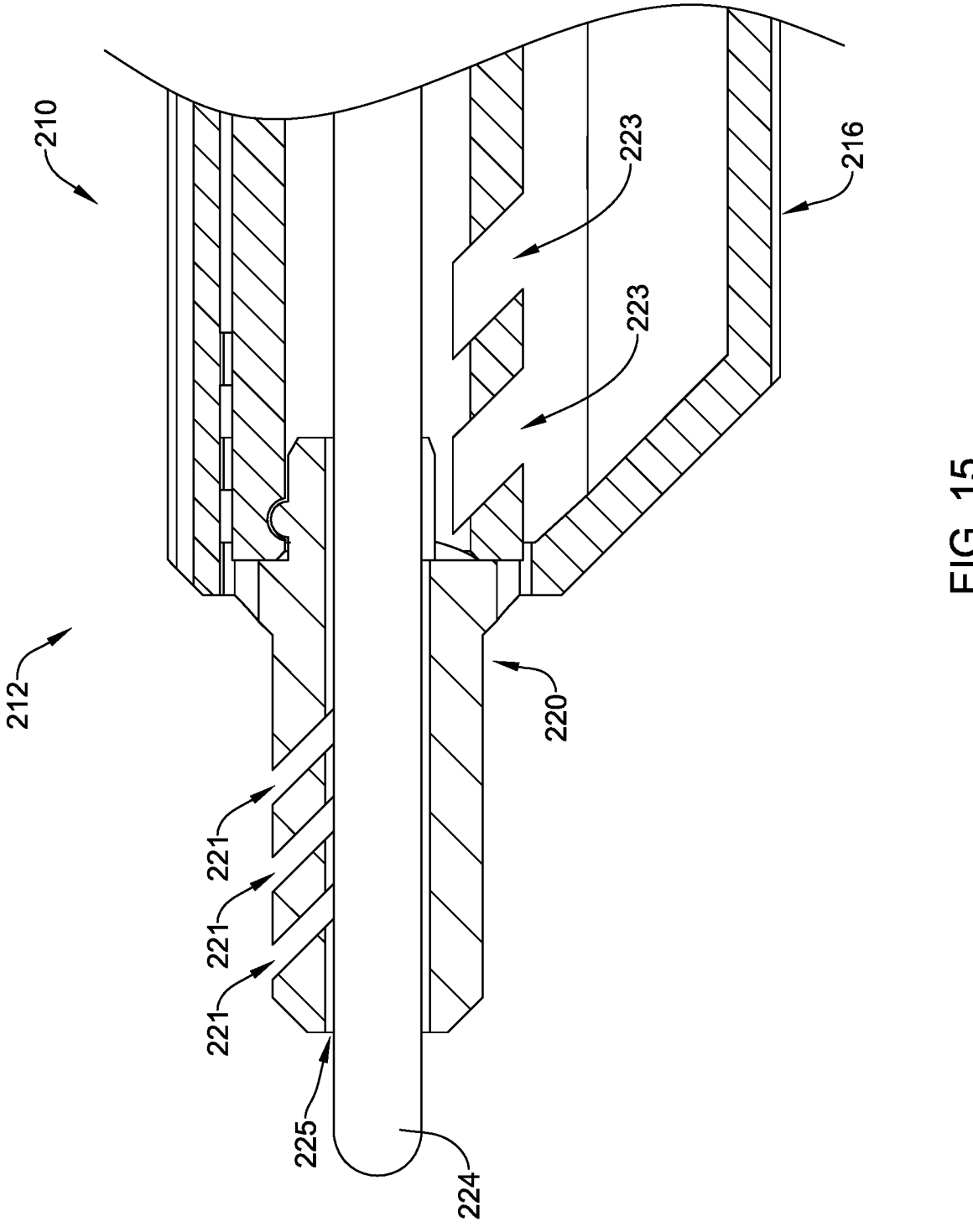
FIG. 15 illustrates a cross-sectional view of the distal end region of example electrosurgical device shown in FIG. 14.

FIG. 15 illustrates a cross-sectional view of the distal end of the electrosurgical device 210 shown in FIG. 13, whereby a portion of the shroud 220 has been retracted into the body 216 to expose the electrode 224. FIG. 15 illustrates that the electrode 224 may be positioned within an inner lumen 225 of the shroud 220. FIG. 15 further illustrates the angled slots 221 extending from an outer surface of the shroud 220, through the wall of the shroud 220 to the inner lumen of the shroud 220. Therefore, it can be appreciated that the angled slots 221 may provide a fluid pathway from outside the shroud 220 through the wall of the shroud 220 to the inner lumen 225 of the shroud 220. Additionally, FIG. 15 illustrates that this fluid pathway may continue through the inner lumen 225 to the slots 223 which may extend from the inner lumen 225 of the shroud 220 to an inner cavity (e.g. inner lumen) of the body 216. Therefore, it can be appreciated that fluid, smoke, etc. may enter the slots 221 from a location outside the shroud 220 (e.g., a surgical site), pass through the slots 221 into the inner lumen 225 of the shroud and continue to the slots 223, whereby the fluid may then pass through the slots 223 into the inner cavity of the body 216. Additionally, the fluid may then pass through the inner cavity of the body 216 to the inner lumen of the proximal connector 222 (described above), whereby the fluid may then be evacuated through one or more tubes and/or connectors to one or more components of an electrosurgical system.

Figure 16:
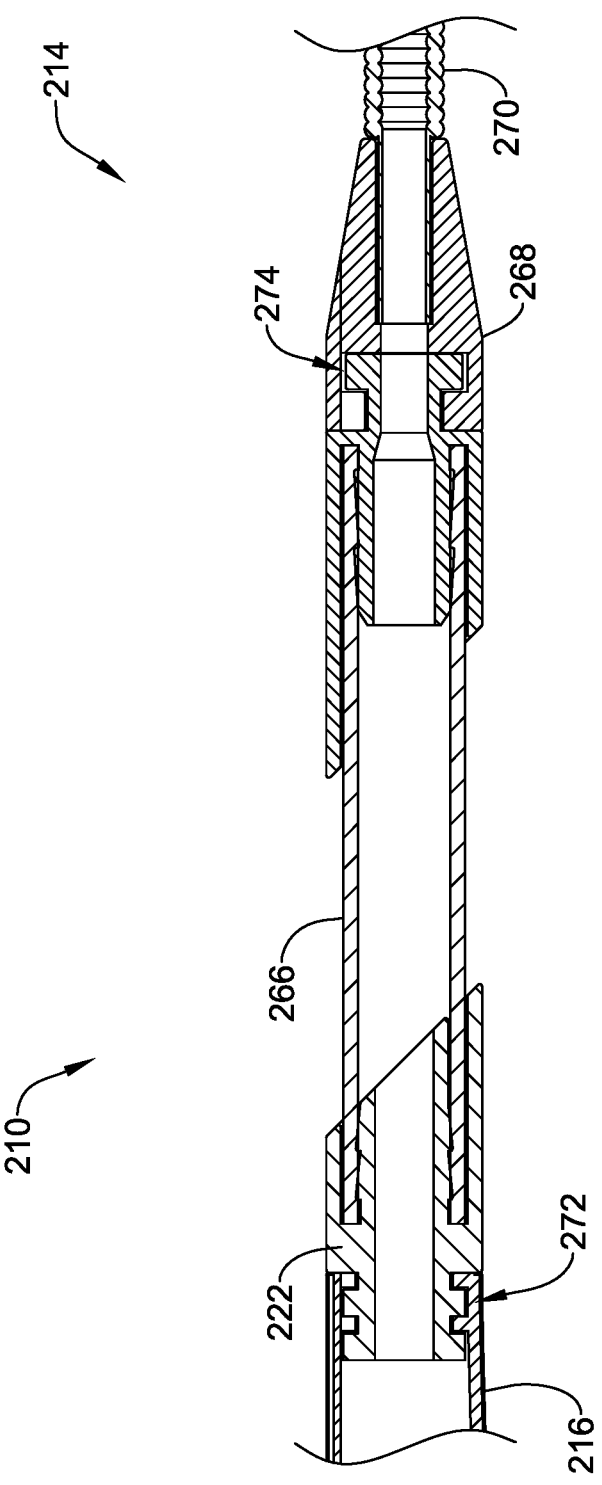
FIG. 16 illustrates a cross-sectional view of the proximal end region of example electrosurgical device shown in FIG. 14.

FIG. 16 illustrates a cross-sectional view of the proximal end region 214 of the electrosurgical device 210. As discussed above, FIG. 16 illustrates the first proximal connector 222 which is attached to a proximal end of the body 216. In some examples, the first proximal connector 222 may be coupled to the proximal end of the body 216 via a swivel connection 272. It can be appreciated that swivel connection 272 may permit the first proximal connector 222 (and any components attached proximally thereto) to rotate (e.g., spin, swivel, turn, etc.) relative to the body 216.

FIG. 16 further illustrates the first flexible tube 266 attached to the first proximal connector 222. In some instances, the first flexible tube 266 may be designed as a strain relief component for the first proximal connector 222. In other words, the first flexible tube 266 may be constructed from a material which is designed to absorb a flexural load imparted from the weight of the second proximal connector 268 and/or the second proximal tube 270. Additionally, it can be appreciated that, in some examples, one or more wires may pass from an electrosurgical system (e.g., the electrosurgical system 500 shown in FIG. 30) through the second proximal tube 270, the second proximal connector 268, the first flexible tube 266 and the first proximal connector 222 before entering the body 216 of the electrosurgical device 210.

FIG. 16 further illustrates the second proximal connector 268 attached to both the first flexible tube 266 and the second flexible tube 270. In some examples, the second to proximal connector 268 may be coupled to the first proximal tube 266 via a swivel connection 274. It can be appreciated that the swivel connection 274 may permit the second proximal connector 268 and the second proximal tube 270 (and any components attached proximally thereto) to rotate (e.g., spin, swivel, turn, etc.) relative to the first proximal tube 266.

Figure 17:
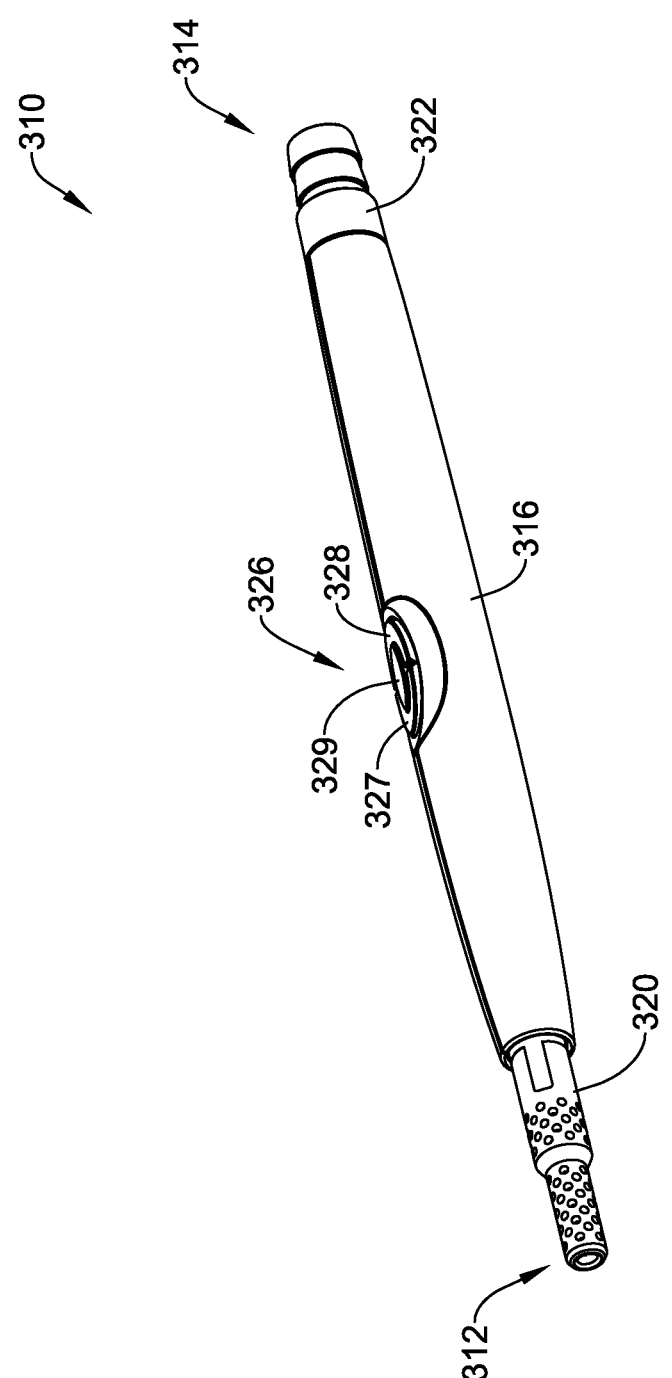
FIG. 17 illustrates another example electrosurgical device in a first position.

FIG. 17 illustrates another example electrosurgical device 310. The electrosurgical device 310 may be similar in form and function of other electrosurgical devices disclosed herein. For example, the electrosurgical device 310 may include a distal end region 312 and a proximal end region 314. The distal end region 312 of the electrosurgical device 310 may include a shroud 320 which is coupled to a body portion 316. In some instances, the shroud 320 may be designed to be permanently secured to the body portion 316 (e.g., the shroud 320 may not be easily removed from the body and replaced with a different shroud). However, in other instances, the shroud 320 may be releasably secured to the body 316 to permit replacement of the shroud 320 (e.g., the shroud 320 may be replaced with other shrouds of different sizes, shapes, apertures, etc.).

FIG. 17 further illustrates that the electrosurgical device 310 may further include a proximal connector 322 positioned along the proximal end region 314 of the electrosurgical device 310. As will be described in greater detail below, the proximal connector 322 may be utilized to attach the electrosurgical device 310 to an electrosurgical system (e.g., shown in FIG. 30).

As discussed above, the electrosurgical device 310 may include an electrode (e.g., shown in FIG. 18) which may be utilized to cut and/or coagulate tissue during a medical procedure. The electrode 324 may generate intense heat during use, and therefore, it can be appreciated that the electrosurgical device 310 may be designed to shield the electrode 324 when not in use. Specifically, the electrosurgical device 310 may include an actuatable, protective shroud 320 which covers the electrode 324 when not in use, but also actuates (e.g., translates from a first position to a second position) to expose the electrode 324 to cut or coagulate tissue when desired.

FIG. 17 further illustrates that the electrosurgical device 310 may include an electrosurgical actuator 326 positioned along a surface of the body 316. In some instances, the electrosurgical actuator 326 may include an actuation button 329 (e.g., a central actuator) which is generally positioned between a first power button 327 and a second power button 328. In some examples, the first power button 327 and the second power button may be shaped such that they substantially surround the actuation button 329. Depressing the actuation button 329 may be utilized to translate the shroud 320 between a first position in which the shroud 320 is covering the electrode 324 (e.g., shown in FIG. 17) and a second position in which the shroud 320 is retracted to expose the electrode 324 (e.g., shown in FIG. 18). A more detailed description of the operation of the electrosurgical actuator 326 (including the actuation button 329, the first power button 327 and the second power button 328) is set forth below.

Figure 18:
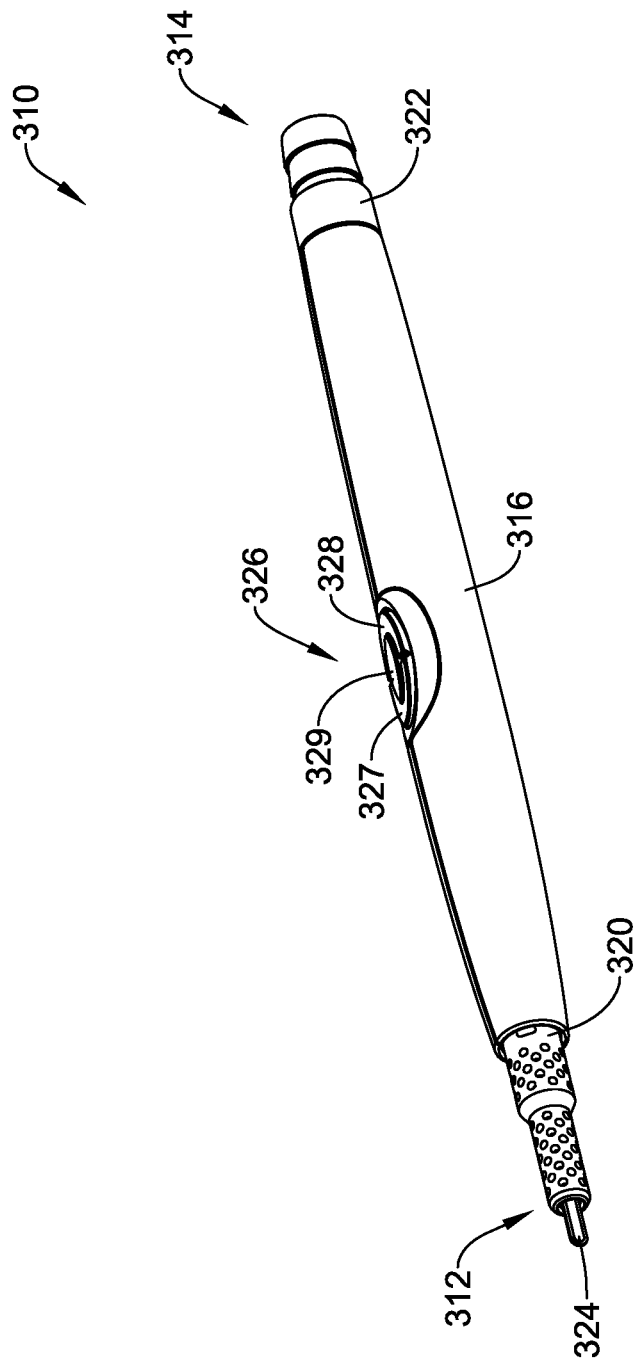
FIG. 18 illustrates the example electrosurgical device shown in FIG. 17 in a second position.
Figure 19:
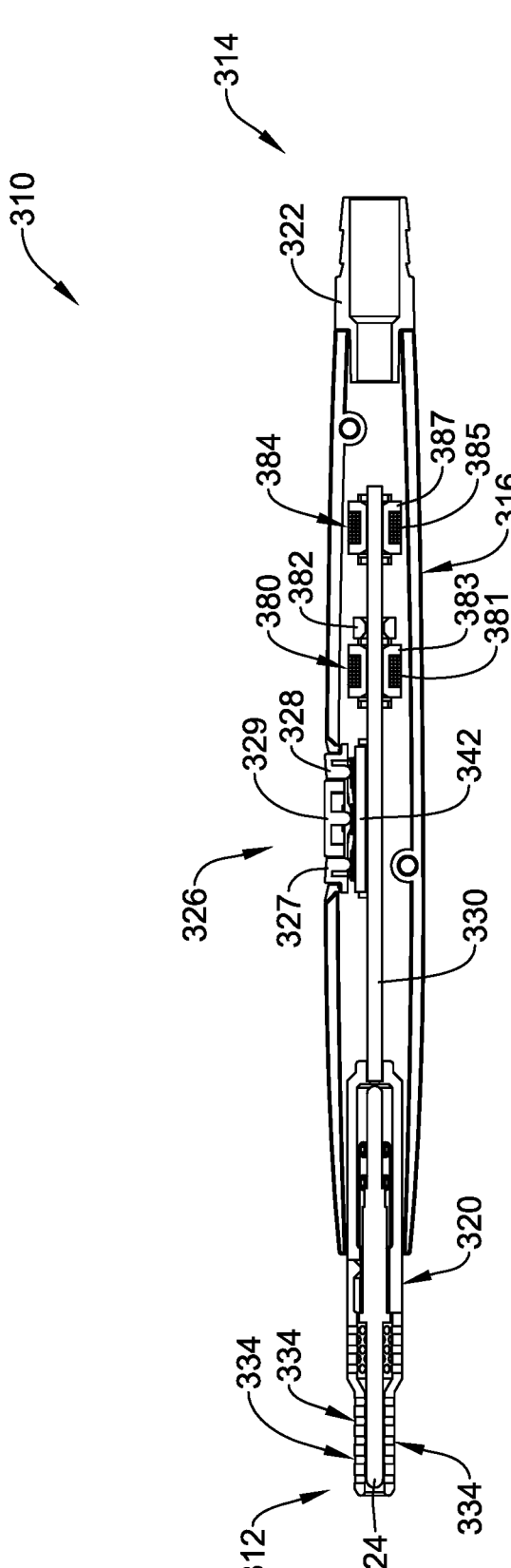
FIG. 19 illustrates a cross-sectional side view of the example electrosurgical device shown in FIG. 17.

FIG. 19 illustrates that the actuation button 329 may be coupled to one or more magnets of a magnetic assembly, whereby the magnetic assembly may be designed to translate the shroud 320. For example, FIG. 19 illustrates that the distal end of an actuation shaft 330 may be attached to the proximal end of the shroud 320, and therefore, actuation of the actuation shaft 330 (along the central longitudinal axis of the body 316, for example) may translate the shroud 320 between a first position (in which the shroud 320 is covering the electrode 324, as shown in FIG. 17) and a second position (in which a portion of the shroud 320 is retracted into the body 316 to expose the electrode 324, as shown in FIG. 18). Additionally, FIG. 20 illustrates that a proximal end of the actuation shaft 330 may be fixedly attached to a magnetic assembly which may include a first magnet component 380, a second magnet component 382 and a third magnet component 384.

In some instances, such as the example illustrated in FIGS. 17-20, the first magnetic component 380 and the third magnetic component 384 may each include an electromagnet. It can be appreciated that the electrosurgical device 310 may include known wiring configurations common to electrosurgical devices (e.g., electrosurgical pens). Further, as discussed herein, an "electromagnet" may include a type of magnet in which uses an electric current to produce a magnetic field. Accordingly, electromagnets (such as the first magnetic component 380 and the third magnetic component 384) may include a wire wound into a coil, whereby the coil defines a hole (e.g., aperture) positioned generally in the central region of the coil. A current passing through the wire may create a magnetic field which is concentrated in the hole. In some instances, the wire is wound around a magnetic core made from a ferromagnetic or ferrimagnetic material. Further, it can be appreciated that the magnetic core may strengthen the magnetic field generated by the electromagnet, while also providing structural strength to withstand repeated engagement of the electromagnet with actuating components.

Figure 20:
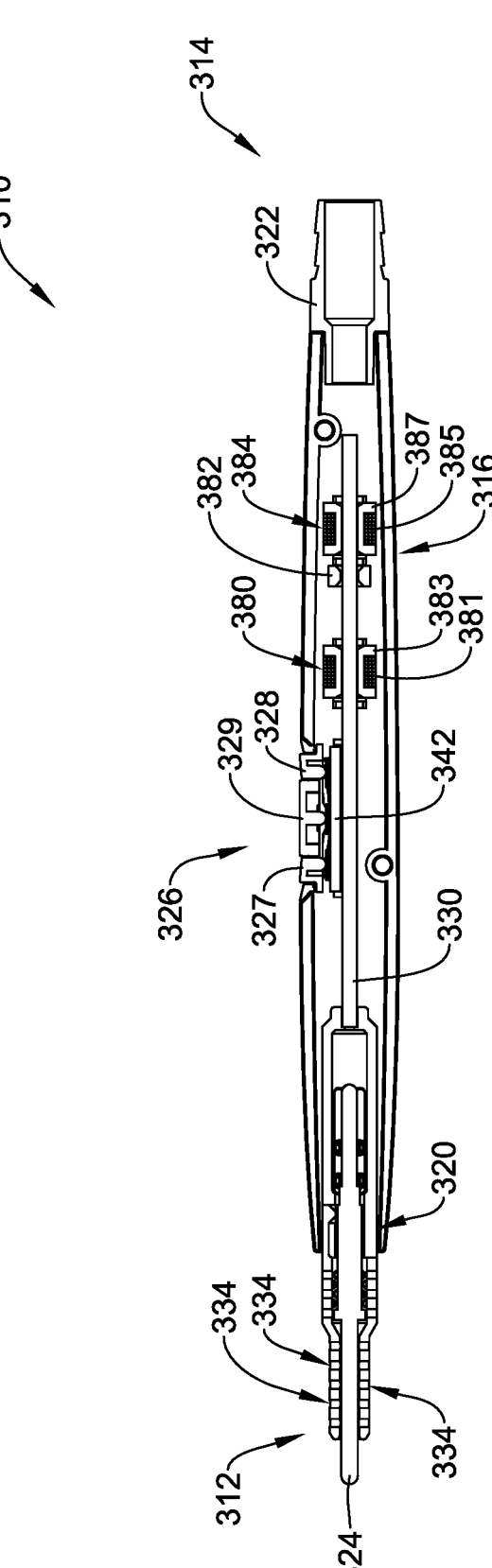
FIG. 20 illustrates a cross-sectional side view of the example electrosurgical device shown in FIG. 18.

Referring to the first magnetic component 380 and the third magnetic component 384 of FIG. 20, it can be appreciated that, in some instances, the first magnetic component 380 may include an electromagnet having a wire 381 wound around a magnetic core 383. Similarly, the third magnetic component 384 may also include an electromagnet having a wire 385 would around a magnetic core 387. In some examples, the magnetic core 383 and the magnetic core 387 may each be referred to as a "bobbin." As described above, the wire 381 may be positionally fixed to the magnetic core 383 while the wire 385 may be positionally fixed to the magnetic core 387. Additionally, in some examples, the direction that the wire 381 is wound around the magnet core 383 of the first magnetic component 380 may be opposite to the direction that the wire 385 is wound around the magnetic core 387 of the third magnetic component 384.

Additionally, it can be appreciated that the wire 381 and wire 385 may be two separate, distinct wires which define a first electrical pathway which is separate (e.g., distinct) from a second electrical pathway. It can be further appreciated that the first electrical pathway may be utilized to energize the first magnetic component 380 independently of the second electrical pathway, which may be utilized to energize the third magnetic component 384. However, in other examples, the wire 381 and the wire 385 may be formed from a single, continuous wire which is wound around the magnetic core 383 in a first direction and wound around the magnetic core 387 in a second direction, whereby the second direction is opposite to that of the first direction. It can be further appreciated that this single, continuous wire may create a single electrical pathway which is utilized to energize both the first magnetic component 380 and the third magnetic component 384. Therefore, some examples contemplated herein may include two individual electromagnets which are energized via two separate, distinct electrical pathways, while other examples contemplate two individual electromagnets which are energized via a single, continuous electrical pathway.

Further, the wire 381 of the first magnetic component 380 and the wire 385 of the third magnetic component 384 may be coupled a circuit board 342. Further yet, the circuit board 342 may be coupled to an electrical source (e.g., electrosurgical generator, interface console, power source, battery, etc.) of an electrosurgical system. Accordingly, it can be appreciated that the circuit board 342 may signal the flow of electrical current from an electrical source (e.g., electrosurgical generator, interface console, power source, battery, etc.) to either the wire 381 of the first magnetic component 380 or the wire 385 of the third magnetic component 384. As discussed above, an electrical current flowing through either the wire 381 of the first magnetic component 380 or the wire 385 of the third magnetic component 384 may generate a magnetic field within the magnetic core 383 of the first magnetic component 380 and the magnetic core 387 of the third magnetic component 384, respectively. Additionally, it can be appreciated that for embodiments in which the wire 381 is wound around the magnetic core 383 of the first magnetic component 380 in a direction opposite to the direction for which the wire 385 is wound around the magnetic core 387 of the third magnetic component 384, the polarity of the magnetic field generated in the magnetic core 383 of the first magnetic component 380 may be opposite to the polarity of the magnetic field generated in the magnetic core 387 of the third magnetic component 384.

FIG. 19 further illustrates that the electrosurgical device 310 may also include a second magnetic component 382 which is positioned between the first magnetic component 380 and the third magnetic component 384. Further, the second magnetic component 382 may be fixedly attached to the proximal end of the actuation shaft 330. Further yet, the actuation shaft 330 may extend through the core 383 of the first magnetic component 380, through an aperture in the second magnetic component 382 and continue extending through the core 387 of the third magnetic component 384. It can be appreciated that, in some instances, the actuation shaft 330 may be designed to translate relative to both the first magnetic component 380 and the third magnetic component 384. In other words, the first magnetic component 380 and the third magnetic component 384 may be held in a fixed position relative to the body 316, while the actuation shaft 330 may translate through an aperture located in the core 383 of the first magnetic component 380 and an aperture located in the core 387 of the third magnetic component 384.

In some instances, such as the embodiment illustrated in FIGS. 17-20, the second magnetic component 382 may include a permanent magnet. Therefore, it can be appreciated that a magnetic field generated in the core of either the first magnetic component 380 and/or the third magnetic component 384 may attract or repel the second magnetic component 382 (depending on the specific polarity of the magnetic components 380/384 and the second magnet component 382). For example, FIG. 19 illustrates that an electrical current flowing through the wire 381 of the first magnetic component 380 may generate a magnetic field in the core 383 of the first magnetic component 380 having a polarity that attracts the second magnet component 382 (it is noted that, in this example, the second magnetic component

382 includes a permanent magnet). Additionally, coincident with the generation of a magnet field in the first magnetic component 380 that attracts the second magnetic component 382, an electrical current may be passed through the wire 385 of the third magnetic component 384 which generates a magnetic field in the core 387 of the third magnetic component 384 having a polarity that repels the second magnetic component 382. Therefore, because the second magnetic component 382 is fixedly attached to the actuation shaft 330, and the shroud 320 is attached to the actuation shaft 330, applying electrical currents through both the wire 381 of the first magnetic component 380 and the wire 385 of the third magnetic component 384 may engage the second magnetic component 382 with the first magnetic component 380 thereby maintaining the shroud 320 in the a first position (in which the shroud 320 is covering the electrode 324, as shown in FIG. 19).

However, it can be appreciated that reversing the electrical current flowing through the wire 381 of the first magnetic component 380 and the electrical current flowing through the wire 385 of the third magnetic component 384 may reverse the polarities of the magnetic core 383 of the first magnetic component 380 and the core 387 of the third magnetic component 384. Further, it can be appreciated that reversing the polarity of the first magnetic component 380 may cause the second magnetic component 382 to be repelled away from the first magnetic component 380, while reversing the polarity of the third magnetic component 384 may cause the second magnetic component 382 to be attracted to the third magnetic component 384.

For example, FIG. 20 illustrates the second magnetic component 382 being repelled by the first magnetic component 380 while simultaneously being attracted to the third magnetic component 384. Further, it can be appreciated by comparing FIG. 19 and FIG. 20, the actuation shaft 330 may translate in a distal-to-proximal direction as the second magnetic component 382 is pushed away from the first magnetic component 380 and pulled toward the third magnetic component 384. It can further be appreciated that translating the actuation shaft 330 in a distal-to-proximal direction may actuate the shroud 320 from a first position (in which the shroud 320 is covering the electrode 324, as shown in FIG. 19) to a second position (in which the shroud 320 is retracted to expose the electrode 324, as shown in FIG. 20).

As discussed above, the circuit board 342 may be coupled to each of the first magnetic component 380 and the third magnetic component 384 via one or more electrical wires which are utilized to pass an electrical current (received from an electrosurgical generator of an electrosurgical system, for example) through the wire 381 of the first magnetic component 380 and/or the wire 385 of the third magnetic component 384, as described above. It can be further appreciated from FIGS. 19-20 that the actuation button 329 may be utilized to control the circuit board 342. In other words, depressing the actuation button 329 may engage the actuation button 329 with the circuit board 342, whereby the circuit board 342 may then permit an electrical current to flow from an electrosurgical generator to the first magnetic component 380 and/or the third magnetic component 384.

In some instances, the circuit board 342 may be designed to permit an electrical current to flow from the electrosurgical generator to the first magnetic component 380 and/or the third magnetic component 384 for a momentary (e.g., temporary) period of time, whereby after that period of time has expired, the circuit board 342 may stop the flow of electrical current to the first magnetic component 380 and/or the third magnetic component 384. In some examples, the circuit board 342 may be designed to stop the flow of electrical current to the first magnetic component 380 and/or the third magnetic component 384 independent of whether the actuation button 329 remains depressed and engaged with the circuit board 342. Further, the circuit board 342 may be designed to permit an electrical current to resume flow from an electrosurgical generator to the first magnetic component 380 and/or the third magnetic component 384 for a momentary (e.g., temporary) period of time when the actuation button 329 is released (e.g., disengaged from the circuit board 342).

As an example, assume that FIG. 19 illustrates a configuration whereby the second magnetic component 382 is being held to the magnetic core 383 of the first magnetic component 380 without an electrical current being passed through either the first magnetic component 380 or the third magnetic component 384 (e.g., the second magnetic component 382 is being held to the magnetic core 383 of the first magnetic component 380 by virtue of the second magnetic component's 382 interaction with the magnetic material used to construct the core 383). In this configuration, the shroud 320 is being maintained in a stationary position whereby it is covering the electrode 324. As described above, to uncover the electrode 324 and permit a user to cut and/or coagulate tissue, the actuation button 329 may be depressed to engage the circuit board 342. Engagement of the circuit board 342 may permit an electrical current to flow to the first magnetic component 380 and the third magnetic component 384 for a momentary period of time (e.g., the electrical current momentarily flows through the wire 381 of the first magnetic component 380 and the wire 385 of the third magnetic component 384). This flow of electrical current may reverse the polarity of each of the first magnetic component 380 and the third magnetic component 384, which, as described above, may repel the second magnetic component 382 away from the first magnetic component 380 and attract the second magnetic component 382 to the third magnetic component 384. Further, as the second magnetic component 382 translates between the first magnetic component 380 and the third magnetic component 384, it translates the actuation shaft 330, which, in turn, translates the shroud 320 to a second position whereby the electrode 324 is exposed.

After the second magnetic component 382 has engaged the magnetic core 387 of the third magnetic component 384, the circuit board 342 may stop the flow of electrical current to the first magnetic component 380 and the third magnetic component 384. Further, after the flow of electrical current is stopped, the second magnetic component 382 may remain engaged to the magnetic core 387 of the third magnet component 384 by virtue of the second magnetic component's 382 interaction with the magnetic material used to construct the core 387.

However, the shroud 320 may be maintained in the second position (e.g. a retracted position) until the actuation button 329 is released, whereby the circuit board 342 may permit electrical current to momentarily flow to the first magnetic component 380 and the third magnetic component 384, whereby the polarities of the first magnet component 380 and the third magnet component 384 are again reversed and the second magnet component is translated back to the first position thereby translating the shroud 320 to cover the electrode 324. It can be appreciated that designing the electrosurgical device 310 to translate the shroud 320 to a first position when the actuation button 329 is released is an important safety feature for electrosurgical devices. For example, it can be appreciated that when a user is cutting or coagulating tissue, the shroud 320 must be retracted to expose the electrode 324. However, as discussed above, an energized electrode 324 has the potential to generate intense heat and start fires if exposed to a hazardous condition. Therefore, requiring a user to depress the actuation button 329 to expose the electrode 329 also allows the electrosurgical device 310 to include a corresponding safety feature—namely, when the actuation button 329 is released, the shroud 320 immediately translates back to the first position and covers the electrode 324, thereby shielding the electrode 324 (e.g. from inadvertently starting a fire, etc.)

As described above, the electrosurgical device 310 may be utilized to both cut or coagulate tissue. Accordingly, it can be appreciated that different profile of energy may be provided to the electrode 324 depending on whether the user decides to cut or coagulate tissue. FIG. 19 illustrates that the electrosurgical actuator 326 may include a first power button 327 and a second power button 328, both of which may be positioned adjacent to the actuation button 329. For example, FIG. 20 illustrates that the first power button 327 may be positioned distal to the actuation button 329 while the second power button 328 may be positioned proximal to the actuation button 329.

In some instances, the first power button 327 may be utilized to cut tissue while the second power button 328 may be utilized to coagulate tissue. For example, when a user depresses the first power button 327, the first power button 327 may engage the circuit board 342, whereby the circuit board 342 sends a signal to an electrosurgical generator to provide the electrode 324 with a given profile of energy to cut tissue. Similarly, when a user depresses the second power button 328, the second power button 328 may engage the circuit board 342, whereby the circuit board 342 sends a signal to an electrosurgical generator to provide the electrode 324 with a different profile of energy to coagulate tissue. As described above, in some instances, the energy delivered to the electrode 324 to cut tissue may be different than the energy delivered to coagulate tissue. While the above discussion describes the first power button 327 as suppling a different profile of energy relative to the second power button 328, a reverse configuration is also contemplated, whereby the electrosurgical device 310 is configured such that the energy supplied by the first power button 327 is used to coagulate tissue while the energy supplied by the second power button 328 is used to cut tissue.

Additionally, FIG. 20 illustrates that the electrosurgical actuator 326 may be designed to require a user to depress the actuation button 329 at the same time as the first power button 327 or the second power button 328 to both retract the shroud 320 and energize the electrode 324. For example, a user may utilize a single finger to depress the actuation button 329 to uncover the shroud 320 (as described above), while simultaneously "rocking" their finger either forward or backward to depress either the first power button 327 or the second power button 328, respectively. This sequence of steps may initially retract the shroud 320 to uncover the electrode 324 (via depressing the actuation button 329), followed by energizing the electrode 324 to either cut or coagulate tissue (via depressing either the first power button 327 or the second power button 328). As discussed above, removing the finger from the actuation button 329 (e.g., releasing the actuation button 329) may immediately translate the shroud 320 from the second position (e.g., a retracted position) to the first position in which the shroud 320 covers the electrode 324.

Further, it is contemplated that the electrosurgical device 310 may include a "press and release" activation mechanism. For example, it is contemplated that a single press and release of the activation button 329 may retract (or advance) the shroud 320, a single press and release of the first power button 327 may energize (or deactivate) the electrode 324 to cut tissue and a single press and release of the second power button 328 may energize (or deactivate) the electrode 324 to coagulate tissue.

Additionally, it is further contemplated that while some electrosurgical devices (such as the device 310 described herein) may include three buttons (e.g., a first power button, second power button and an actuation button) which may retract the shroud, retract the shroud and cut tissue, and retract the shroud and coagulate tissue, it is also contemplated that some electrosurgical devices contemplated herein may include only two buttons. For example, electrosurgical devices are contemplated which may include a first button which retracts the shroud and energizes the electrode to cut tissue and a second button which retracts the shroud and energizes the electrode to coagulate tissue. It can be further appreciated that in a two-button design, releasing either of the buttons (while the electrode is energized) may activate the shroud to cover the electrode. Hence, for both the three-button and two-button design, energizing the electrode (and retraction of the shroud) requires the user to press and hold one or more buttons, whereby releasing the held button advances the shroud over the electrode. Additionally, it can be appreciated that, in some examples, a two-button design may include a "multi-stage press" design in which depressing a button halfway retracts the shroud and continuing to fully depress the button energizes the electrode. This multi-stage press design feature may be applied to either or both of the first (e.g., cut mode) button or the second (e.g., coagulate mode) button.

Like that described above with respect to other electrosurgical devices, FIG. 20 further illustrates that the shroud 320 may include one or more apertures 334 (e.g., holes, openings, fluid pathways, channels, etc.) extending from an outer surface of the shroud 320, through the wall of the shroud 320 to the inner lumen of the shroud 320. The apertures 334 may be designed to permit fluid, air, smoke, etc. to flow from a position outside the shroud 320 into the inner lumen of the shroud 320 (which may be occupied by the electrode 324). Further, the inner lumen of the shroud 320 may be in fluid communication with the cavity of the body 316. Further yet, as described above, the cavity of the body 316 may be in fluid communication with the lumen of the proximal connector 322. The proximal connector 322 may be attached to an evacuation tube coupled to an electrosurgical system 500 (e.g., shown in FIG. 30).

It can be appreciated that, in some examples, the electrode 324 may need to be cooled after operation, and therefore, it may be desirable to pass fluid through the apertures 334 and into the lumen of the shroud 320, along the electrode 324 (where it acts to cool the electrode 324) and out of the electrosurgical device 310 via a continuous fluid pathway extending through the lumen of the body 316 and the lumen of the proximal connector 322. Similarly, in some instances, smoke created during the cut/cauterization process may be evacuated from the tissue treatment site through the same fluid pathway described above.

Figure 21:
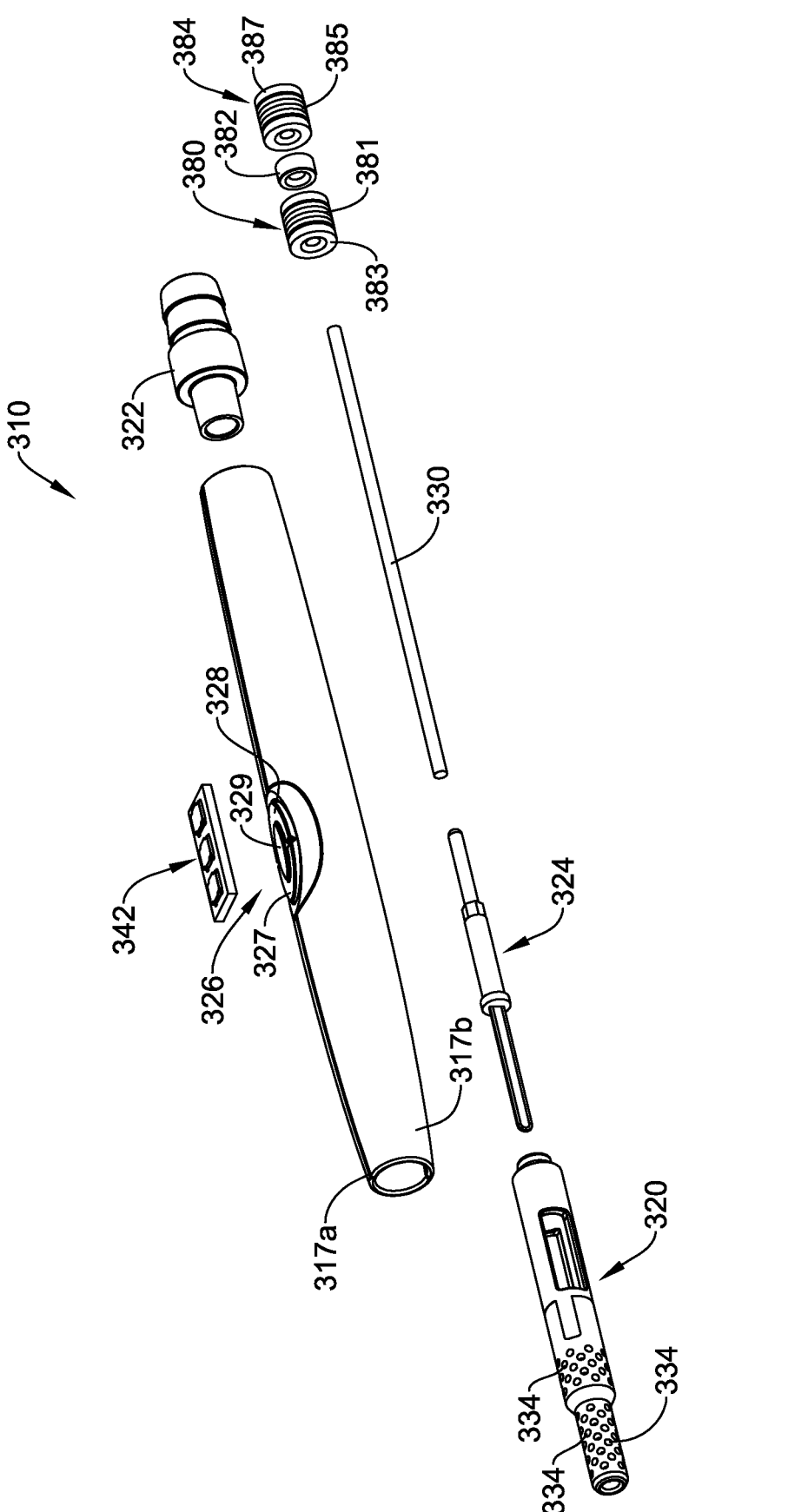
FIG. 21 illustrates an exploded view of the electrosurgical device shown in FIG. 18.

FIG. 21 illustrates an exploded view of the electrosurgical device 310 shown in FIG. 17. FIG. 21 illustrates the body 316 may be formed from a first body component 317a and a second body component 317b attached together in a clamshell configuration (in some examples, the first body component 317a may be snapped together with the second body component 317b to form the body 316). Additionally, FIG. 21 illustrates the shroud 320, including a plurality of apertures 334 disposed around its distal end region. In some examples, the plurality of apertures 334 may extend around the entire circumference of the shroud 320. In other examples, the plurality of apertures 334 may be selectively positioned along the shroud 320 in any pattern or arrangement.

FIG. 21 further illustrates the electrode 324 and the proximal connector 322, both of which engage and remain stationary relative to the body 316, as described above. Additionally, FIG. 21 illustrates the electrosurgical actuator 326, including the actuation button 329, the first power button 327 and the second power button 328. The actuation button 329, the first power button 327 and the second power button 328 may engage the circuit board 342 to control the profile of energy provided to the electrode 324 to cut or coagulate tissue.

FIG. 21 further illustrates the shaft 330 aligned with the first magnet component 380, the second magnet component 382 and the third magnetic component 384. As shown in FIG. 21 and described above, the first magnetic component 380 may include an electromagnet having a wire 381 coiled around a magnetic core 383, while the third magnet component 384 may include an electromagnet having a wire 385 coiled around a magnetic core 387. In some examples, the second magnet component 382 illustrated in FIG. 21 may include a permanent magnet.

Figure 22:
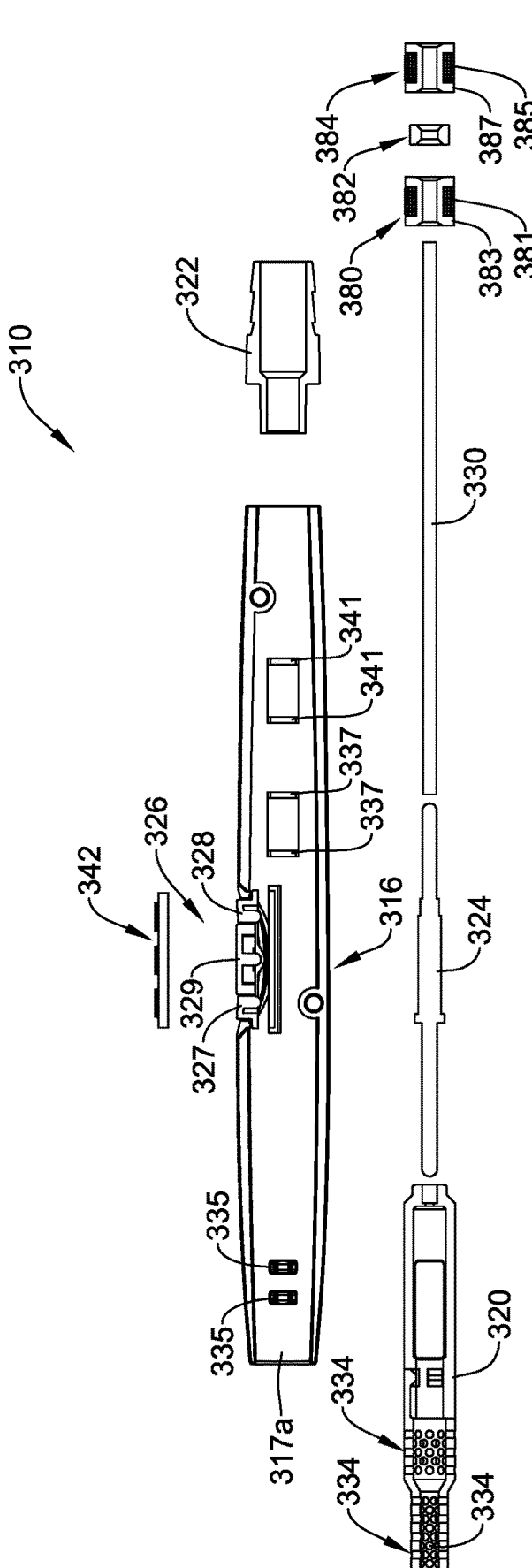
FIG. 22 illustrates another exploded side view of the electrosurgical device shown in FIG. 18.

FIG. 22 illustrates a cross-sectional side view of the electrosurgical device 310 shown in FIG. 21. However, it can be appreciated that the second body component 317b has been removed from the body 316 to reveal the interior surface of the first body component 317a. Accordingly, FIG. 22 illustrates that the first body component 317a and/or the second body component 317b may include one or more structures which are designed to receive, engage and/or hold one or more of the components of the electrosurgical device 310. For example, the interior surface of the first body component 317a (e.g., the interior surface of any component defining the body 316) may include one or more structures 335/337/341 (e.g., molded features) which hold the electrode 324, the first magnet component 380 and/or the third magnet component 384 stationary to the body 316. The features may also hold the circuit board 342 in place relative to the body 316. The features may also provide tracks, rails, alignment features etc. which align the shroud 320 with the shaft 330, thereby assuring that the shroud 320 and the shaft 330 remain aligned when the shaft 330 is translated to expose the electrode 324.

It can be appreciated that, in some examples, the circuit board 342 (or an electrical source) may be coupled to the first magnet component 380 and the third magnet component 384 by a first electrical wire and a second electrical wire, respectively. In other words, in some examples, two separate, individual wires may each be connected to the circuit board 342 (or an electrical source) and the first magnetic component 380 and the third magnet component 384, respectively. Each of the two electrical wires may be utilized to transmit an electrical current to the first magnetic component 380 and the third magnet component 384. For example, a first wire attached to the circuit board 342 (or an electrical source) may extend to the first magnet component 380 and wrap around the magnetic core 383 of the first magnet component 380 (e.g., first electromagnet). Similarly, a second wire attached to the circuit board 342 (or an electrical source) may extend to the third magnet component 384 and wrap around the magnetic core 387 of the third magnet component 384 (e.g., third electromagnet).

Figure 23:
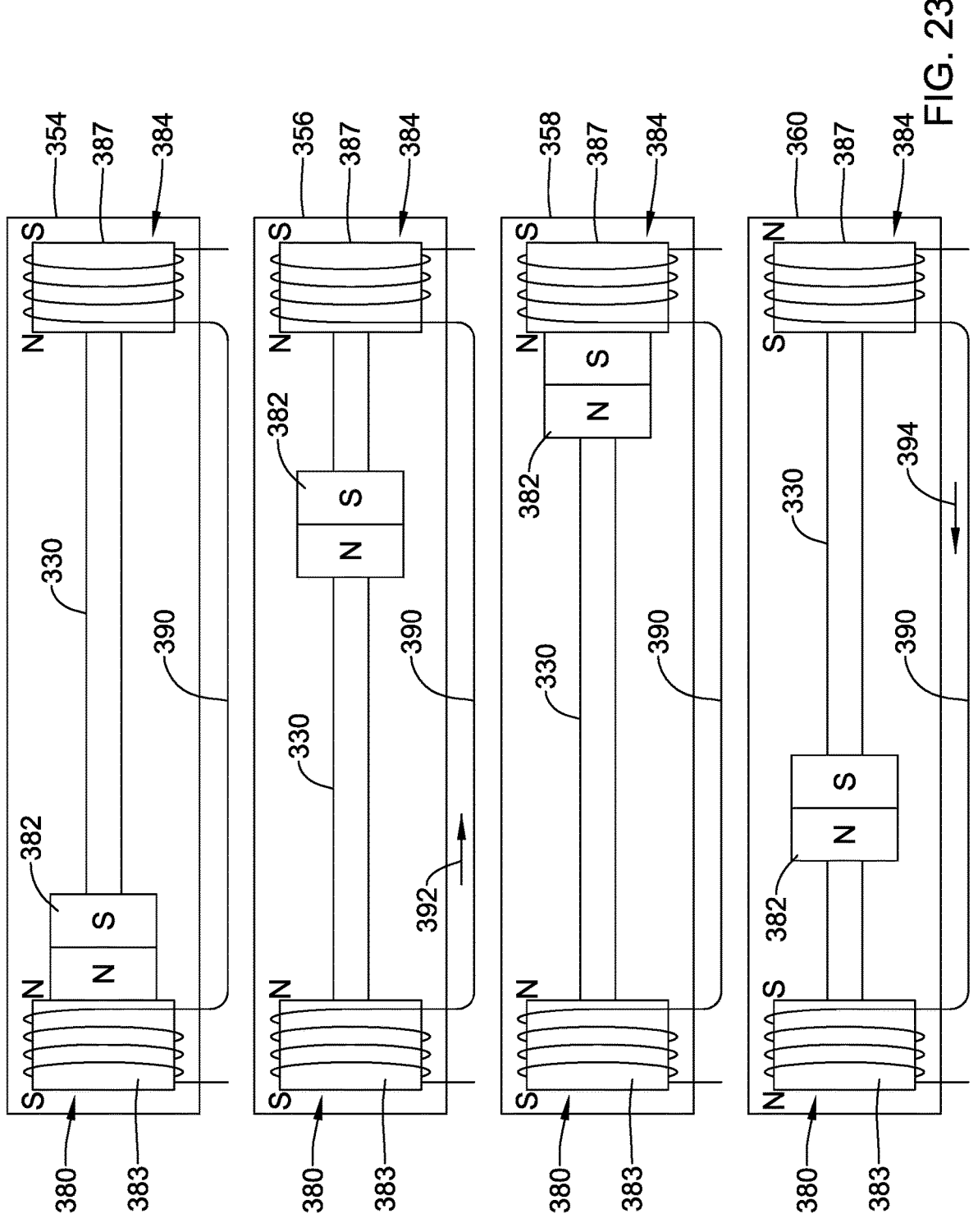
FIG. 23 is a series of schematic illustrations showing an electrosurgical device shifting between a first position and a second position.

However, FIG. 23 illustrates an example configuration in which the electrosurgical device 310 may utilize a single electrical wire 390 to energize both the first magnet component 380 and the third magnet component 384. For illustrative purposes, the first magnet component 380 and the third magnet component 384 shown in FIG. 23 may be defined as a first electromagnet 380 and a third electromagnet 384, respectively. Additionally, FIG. 23 shows the second magnet component 382 positioned between the first magnet component 380 and the third magnet component 384, whereby the second magnet component 382 is fixedly attached to the shaft 330. The second magnet component 382 may include a permanent magnet having a north ("N") and south ("S") polarity. As described above, the shaft 330 may actuate distally and/or proximally as the second magnet component 382 translates between the first magnet component 380 and the third magnet component 384.

As described above, the first schematic illustration 354 of FIG. 23 illustrates a single electrical wire 390 which is coiled around the magnetic core 383 of the first magnet component 380 in a first direction. Additionally, the wire 390 may extend from the first magnet component 380 to the third magnet component 384, whereby the wire 390 is coiled around the magnetic core 387 of the second magnet component 384 in a direction which is opposite to the direction the wire 390 is coiled around the magnetic core 383 of the first magnet component 380. Further, the first schematic illustration 354 of FIG. 23 shows that the second magnet component 382 being held to the first magnet component 380 by virtue of the second magnetic component's 382 interaction with the magnetized core 383 of the first magnet component 380 (e.g., no electrical current is passing through the wire 390 in the schematic illustration 354).

However, the second schematic illustration 356 of FIG. 23 shows movement of the second magnet component 382 away from the first magnet component 380 and toward the third magnet component 384 when an electrical current is passed through the wire 390 from the first magnet component 380 to the third magnet component 384. The direction of the electrical current is depicted by the arrow 392 in the schematic illustration 356. As discussed above, the electrical current 392 may generate a magnetic field in both the first magnet component 380 and the third magnet component 384. Further, the magnetic field generated in the first magnet component 380 may repel the second magnet component 382 (as the electrical current generates a N-N polarity between the first magnet component 380 and the second magnet component 382) while the magnetic field generated in the third magnet component 384 may attract the second magnet component 382 (as the electrical current generates a S-N polarity between the second magnetic component 382 and the third magnet component 384).

The third schematic illustration 358 of FIG. 23 shows the second magnet component 382 held to the third magnet component 384 by virtue of the second magnetic component's 382 interaction with the magnetized core 387 of the third magnet component 384 (e.g., no electrical current is passing through the wire 390 in the schematic illustration 358). It can be appreciated that this illustration may represent a configuration in which the shroud 320 is retracted to expose the electrode 324.

To translate the shroud 320 back to a position in which it covers the electrode 324, an electrical current may be passed through the wire 390 in a direction opposite to that represented the schematic illustration 356 of FIG. 23. For example, the fourth schematic illustration 360 of FIG. 23 shows movement of the second magnet component 382 away from the third magnet component 384 and back toward the first magnet component 380 when an electrical current is passed through the wire 390 from the third magnet component 384 to the first magnet component 380. The direction of the electrical current is depicted by the arrow 394 in the schematic illustration 360. As discussed above, the electrical current 394 may generate a magnetic field in both the first magnet component 380 and the third magnet component 384. Further, the magnetic field generated in the first magnet component 380 may attract the second magnet component 382 (as the electrical current generates a S-N polarity between the first magnet component 380 and the second magnet component 382) while the magnetic field generated in the third magnet component 384 may repel the second magnet component 382 (as the electrical current generates a S-S polarity between the second magnet component 382 and the third magnet component 384).

The above discussion describes that, in some examples, the first magnet component 380 and the third magnet component 384 may include electromagnets, whereby each electromagnet includes a magnetized core (e.g., a bobbin) around which a wire is wound. As described above, there may also be a shaft (e.g., the actuation shaft 330) that may extend through the center of each magnetic core. However, it is noted that this shaft is not the "magnetic core" of the electromagnet and does not need to be magnetizable for operation. The shaft is simply the mechanism that holds/interconnects the second magnet component (e.g., the second magnetic component 382) and the shroud (e.g., the shroud 320) and provides/allows for translation of the shroud 320 along with the second magnet component 382 (via the actuation shaft 330). In fact, the actuation shaft 330 does not necessarily need to go through the center of the magnetic cores 383/387. For example, as will be described in greater detail below, it is contemplated that the shaft structure may extend along the outside of the magnet components 380/384, but also holds the second magnet component 382 between the magnet components 380/384 with a housing, bracket, or the like. However, it can be appreciated that while the shaft structures described herein (e.g., the actuation shaft 330) may include magnetic material, it is also contemplated that the shaft structures described herein may be formed from non-magnetic material. For example, the shaft structures described herein may be formed from a polymeric material.

Additionally, it is contemplated that, in some embodiments, any of the magnet components described herein may also include an electromechanical solenoid. An electromechanical solenoid may include an electrical wire which is wound into a coil which includes a central aperture. Additionally, the electromechanical solenoid may include a magnetized shaft which may translate within the aperture of the coil. It can be further appreciated that passing an electrical current through the coil may translate the magnetized shaft relative to the coil.

While the above discussion describes the electrosurgical device 310 as including a configuration in which a permanent magnet (e.g., the second magnet component 382) is positioned between a first electromagnet (e.g., the first magnet component 380 includes an electromagnet) and a third electromagnet (e.g., the third magnet component 384 includes an electromagnet), other configurations are contemplated.

Figure 24A:
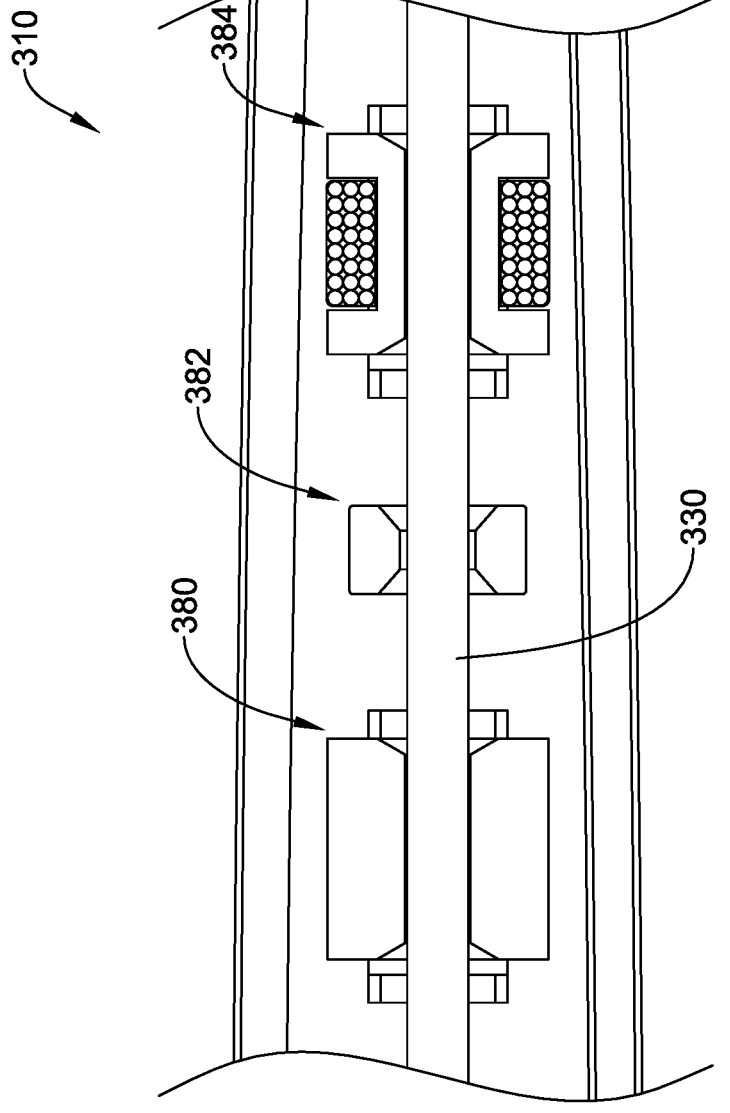
FIG. 24A illustrates an example magnetic assembly.

For example, FIG. 24A illustrates an example configuration in which the first magnetic component 380 includes a permanent magnet or a magnetic material, the second magnetic component 382 includes a permanent magnet or a magnetic material, and the third magnetic component 384 includes an electromagnet. It can be appreciated that in this configuration the shaft 330 may freely pass through the first magnetic component 380 and the third electromagnet 384 but may be fixedly attached to the second magnetic component 382.

Figure 24B:
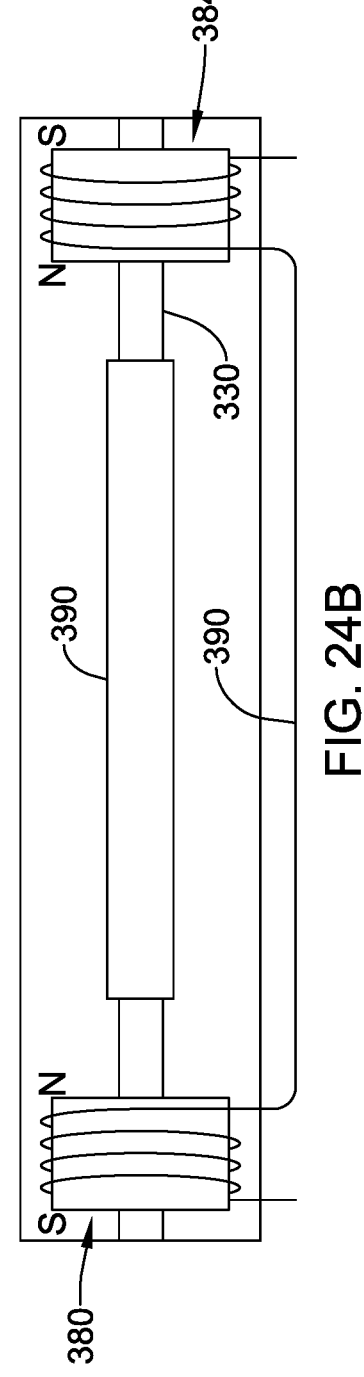
FIG. 24B illustrates another example magnetic assembly.

Additionally, FIG. 24B illustrates that, in some examples, the second magnetic component may be formed as a relatively longer magnet 390 (the second magnetic component 390 illustrated in FIG. 24B is intended to depict a relatively longer version of the second magnetic component 382 illustrated in FIG. 24A). It can be appreciated that designing the electrosurgical device 310 to include a longer second magnetic component 390 may reduce the distance through which the shaft 330 must travel (as compared to the second magnetic component 382 shown in FIG. 24A) to translate the second magnetic component 390 between the first magnetic component 380 and the third magnetic component 384.

Figure 24C:
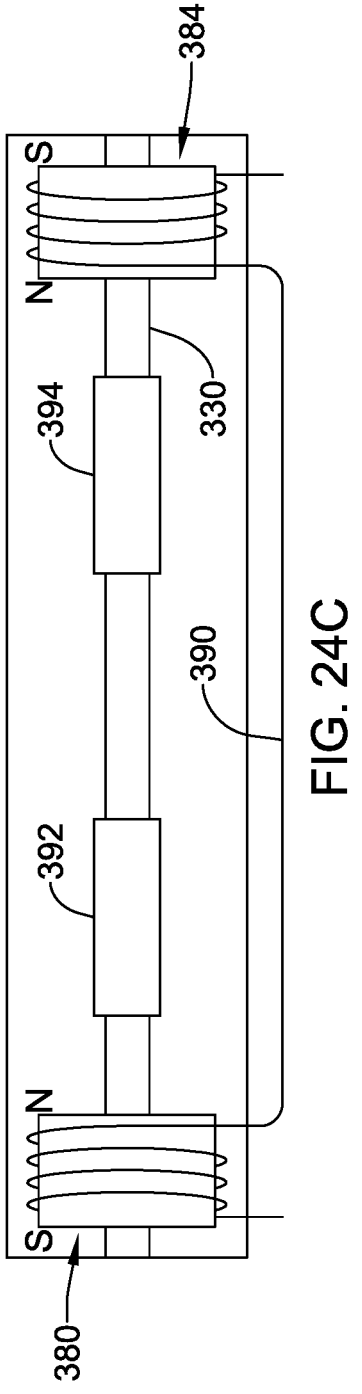
FIG. 24C illustrates another example magnetic assembly.

Similarly, FIG. 24C illustrates that, in some examples, the electrosurgical device 310 may include two second magnetic components 392/394 spaced away from each other along the shaft 330. It can be appreciated that designing the electrosurgical device 310 to include two separate second magnetic components 392/394 may reduce the distance through which the shaft 330 must travel (as compared to the second magnetic component 382 shown in FIG. 24A) to engage/disengage the magnetic component 392 with the first magnetic component 380 and to engage/disengage the magnetic component 394 with the third magnetic component 384.

Figure 25:
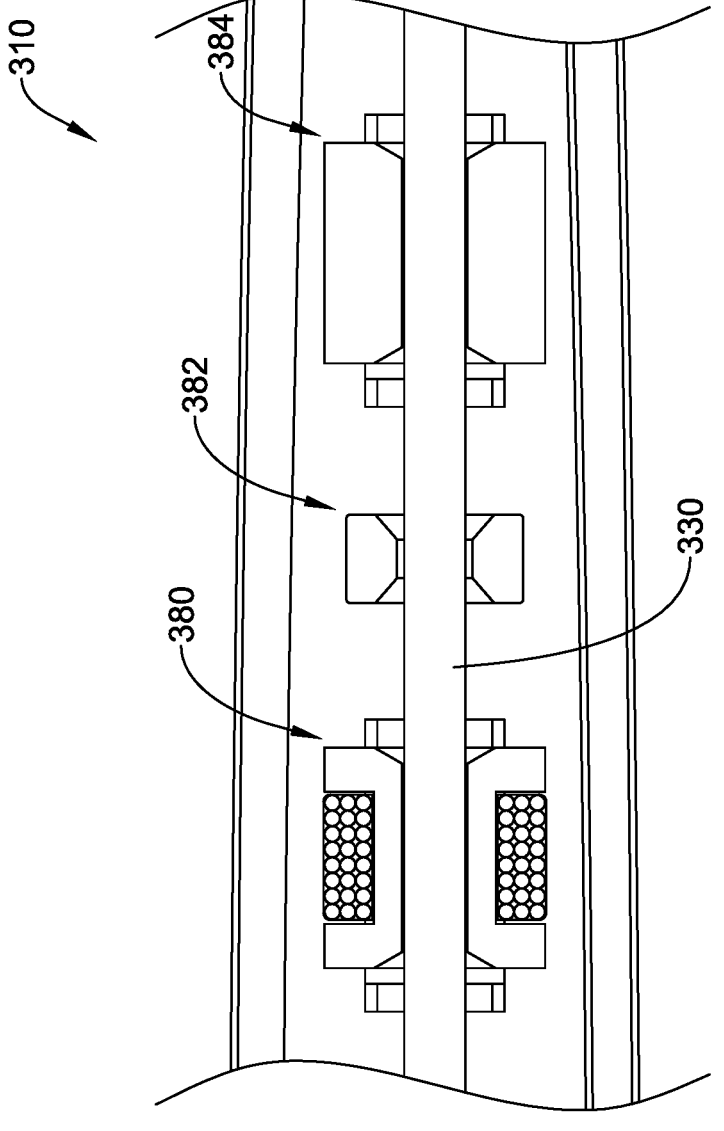
FIG. 25 illustrates another example magnetic assembly.

FIG. 25 illustrates another example configuration in which the first magnetic component 380 includes an electromagnet, the second magnetic component 382 includes a permanent magnet or a magnetic material, and the third magnetic component 384 includes a permanent magnet or a magnetic material. It can be appreciated that in this configuration the shaft 330 may freely pass through the first magnetic component 380 and the third magnetic component 384, but may be fixedly attached to the second magnetic component 382.

Figure 26:
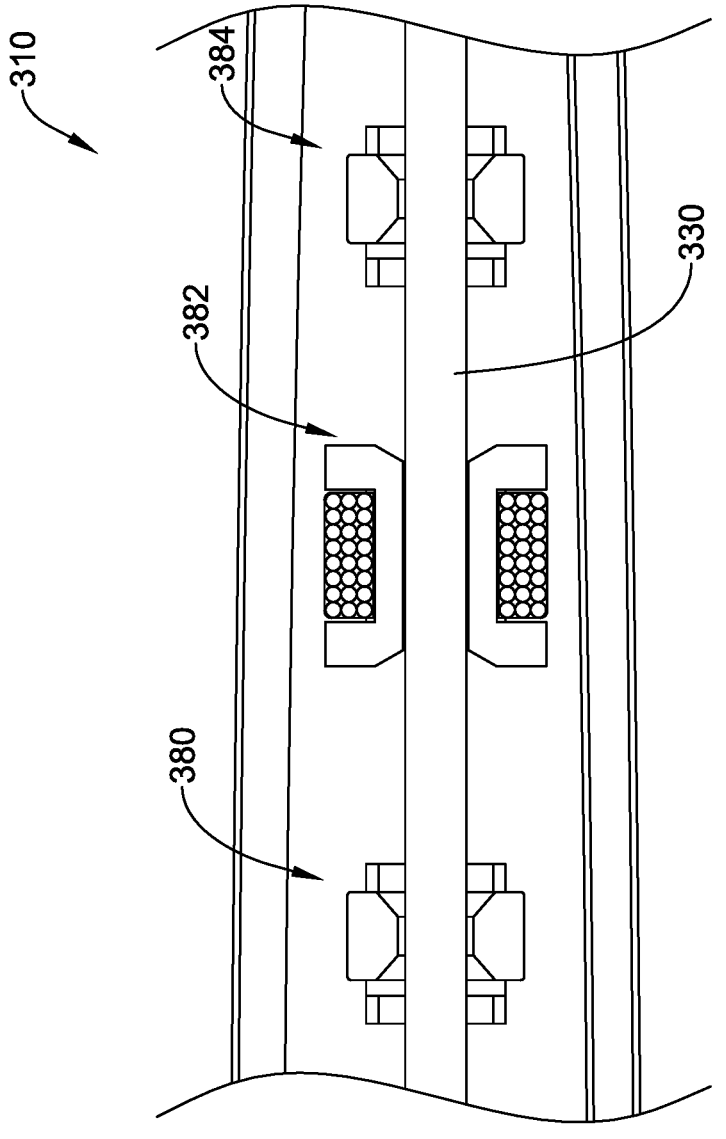
FIG. 26 illustrates another example magnetic assembly.

FIG. 26 illustrates another example configuration in which the first magnetic component 380 includes a permanent magnet or a magnetic material, the second magnetic component 382 includes an electromagnet, and the third magnetic component 384 includes a permanent magnet or a magnetic material. It can be appreciated that in this configuration the shaft 330 may freely pass through the first magnet component 380 and the third magnetic component 384 but may be fixedly attached to the second magnetic component 382.

Figure 27:
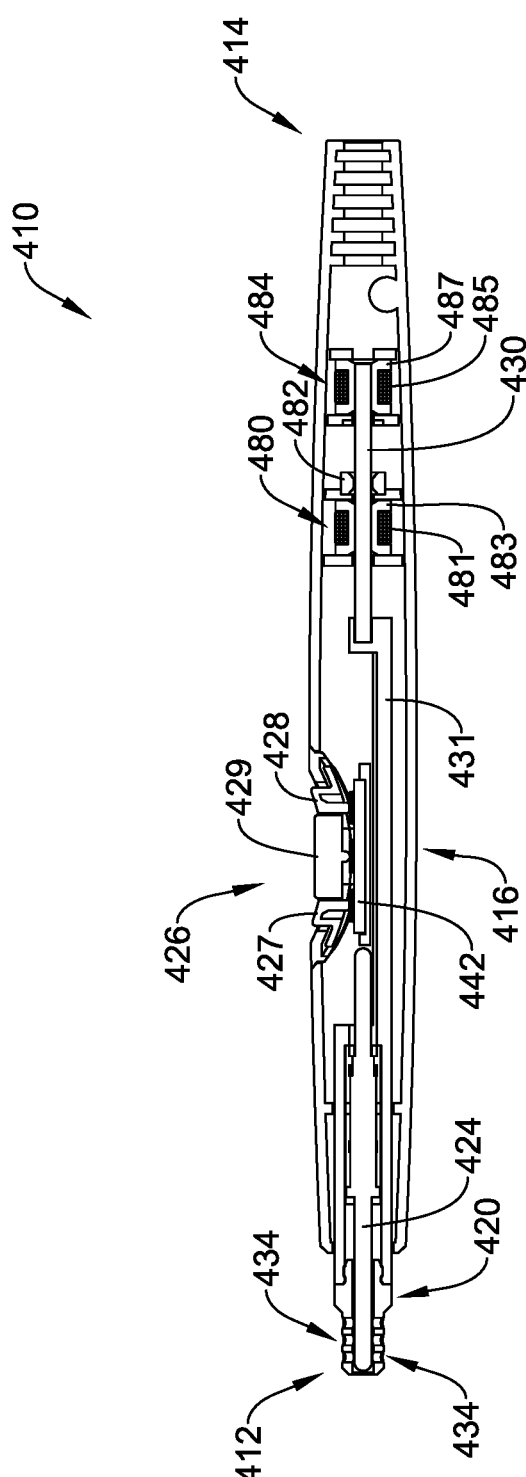
FIG. 27 illustrates a cross-sectional side view of another example electrosurgical device in a first position.

FIG. 27 illustrates another example electrosurgical device 410. The electrosurgical device 410 may be similar in form and function to the electrosurgical device 310 described above. For example, FIG. 27 illustrates that the electrosurgical device 410 may include an actuating shroud 420 positioned along a distal end region 412 of a body 416. Additionally, the electrosurgical device 410 may include an electrosurgical actuator 426 including an actuation button 429. The actuation button 429 may be depressed to translate the shroud 420 from a first position (in which the shroud 420 is covering an electrode 424 as shown in FIG. 27) to a second position (in which the shroud 420 is retracted to expose the electrode 424 as shown in FIG. 28).

Additionally, the electrosurgical actuator 426 may also include a first power button 427 positioned distal to the actuation button 429 and a second power button 428 positioned proximal to the actuation button 429. When depressed, each of the first power button 427 and the second power button 428 may engage a circuit board 442 which permits an electrical current to flow from an electrosurgical generator to the electrode 424. In some examples, the first power button 427 may be utilized to cut tissue, while the second power button 428 may be utilized to coagulate tissue. Further, in some examples, the energy delivered to the electrode 424 to cut tissue may be different than the energy delivered to the electrode 424 to coagulate tissue. Further, the operation of the actuation button 429 in conjunction with the first power button 427 and the second power button 428 may be similar to the operation of the first actuation button 329, the first power button 327 and the second power button 328 of the electrosurgical device 310 described above.

Additionally, like the electrosurgical device 310 described above, FIG. 27 illustrates that the electrosurgical device 410 may include a second magnetic component 482 attached to a shaft 430. The second magnetic component 482 may magnetically interact with a first magnetic component 480 (as shown in FIG. 27) or a third magnetic component 484 (as shown in FIG. 28). The first magnetic component 480 and the third magnetic component 484 may include electromagnets, while the second magnetic component 482 may include a permanent magnet. However, other configurations are contemplated. For example, as described above with respect to the electrosurgical device 310, any one of the first magnetic component 480, the second magnetic component 482 and the third magnetic component 484 may include a permanent magnet, a magnetic material or an electromagnet arranged in any order with respect to one another. Further, FIG. 27 illustrates that the first magnetic component 480 may include a wire 481 coiled around a magnetic core 483, while the third magnetic component 484 may include a wire 485 coiled around a magnetic core 487.

Figure 28:
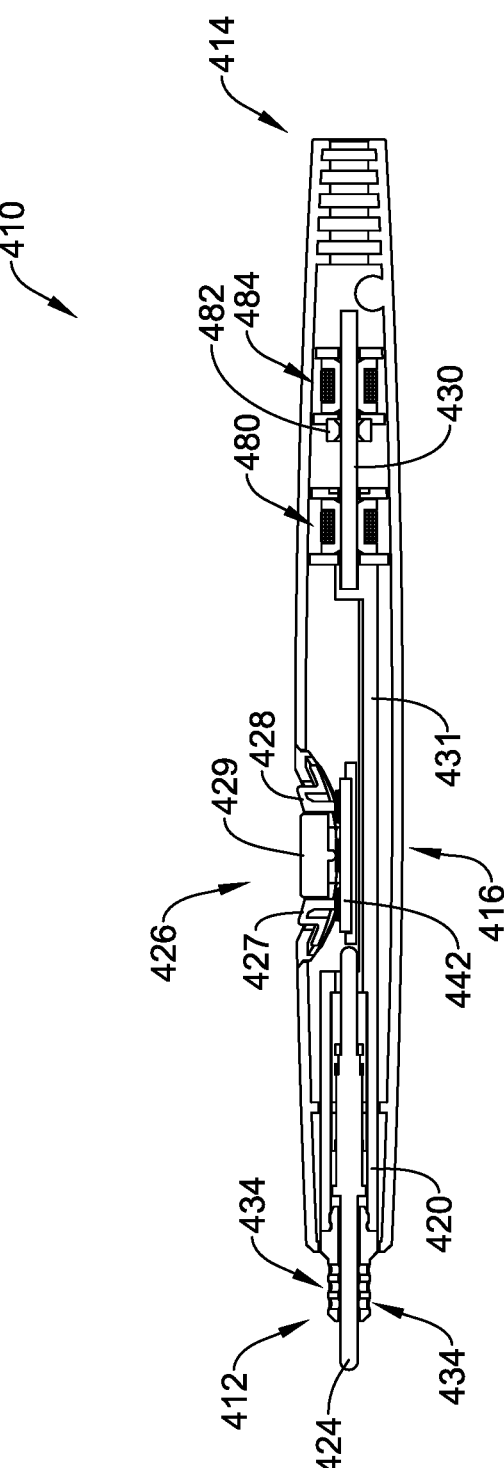
FIG. 28 illustrates a cross-sectional side view of the example electrosurgical device shown in FIG. 27 in a second position.

As described above with respect to the electrosurgical device 310, depressing the actuation button 429 may send momentary electrical currents to the first magnetic component 480 and the third magnetic component 484, thereby creating magnetic fields in both the first magnetic core 483 and the third magnetic core 487 which may either repel or attract the second magnetic component 482 to translate the shroud 420 from a first position (in which it covers the electrode 424 as shown in FIG. 27) to a second position (in which it is retracted to expose the electrode 424 as shown in FIG. 28). Release of the actuation button 429 may reverse the magnetic fields in the first magnetic component 480 and the third magnetic component 484, thereby translating the second magnetic component 482 and the shroud 420 from the second position back to the first position (thereby covering the shroud 420 when a user releases the actuation button 429).

Further, FIG. 27 illustrates that, in some examples, a proximal end region 431 of the shroud 420 may not be aligned along the central longitudinal axis of the body 416. In other words, the proximal end region 431 of the shroud 420 may be vertically offset from the central longitudinal axis of the body 416. Additionally, FIG. 27 illustrates that, in some examples, the proximal end region 431 of the shroud 420 may pass underneath the circuit board 442.

It can be appreciated that the circuit board 442 shown in FIG. 27 may be coupled to one or more wires which may also be coupled to the electrode 424. As discussed above, the wires may be attached to an electrosurgical generator and may transfer an electrical current from the electrosurgical generator to energize the electrode 424 to cut, coagulate, desiccate, ablate, fulgurate, etc. tissue during the electrosurgery.

Like that described above with respect to other electrosurgical devices, FIG. 27 further illustrates that the shroud 420 may include one or more apertures 434 (e.g., holes, openings, fluid pathways, channels, etc.) extending from an outer surface of the shroud 420, through the wall of the shroud 420 to an inner lumen of the shroud 420. The apertures 434 may be designed to permit fluid, air, smoke, etc. to flow from a position outside the shroud 420 into the inner lumen of the shroud 420 (which may be occupied by the electrode 424). Further, the inner lumen of the shroud 420 may be in fluid communication with the cavity of the body 416.

Figure 29:
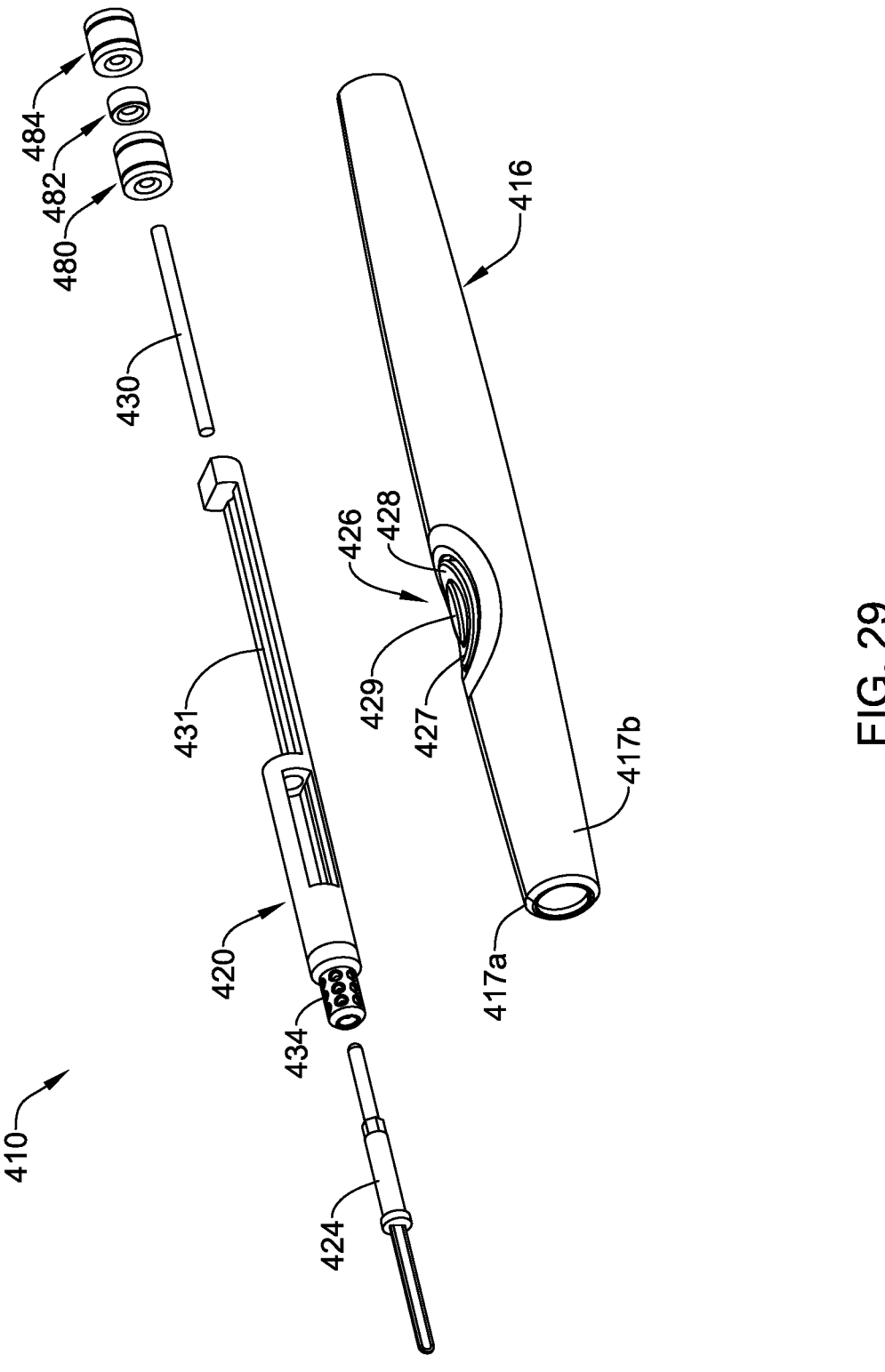
FIG. 29 illustrates an exploded view of the electrosurgical device shown in FIG. 27.

FIG. 29 illustrates an exploded view of the electrosurgical device 410 shown in FIG. 27. FIG. 29 illustrates the body 416 may be formed from a first body component 417a and a second body component 417b attached together in a clamshell configuration (in some examples, the first body component 417a may be snapped together with the second body component 417b to form the body 416). Additionally, FIG. 29 illustrates the shroud 420, including a plurality of apertures 434 disposed around its distal end region. In some examples, the plurality of apertures 434 may extend around the entire circumference of the shroud 420. In other examples, the plurality of apertures 434 may be selectively positioned along the shroud 420 in any pattern or arrangement.

As described above, FIG. 29 further illustrates that a proximal end region 431 of the shroud 420 may be offset from a central longitudinal axis of a distal end region of the shroud 420. For example, FIG. 29 illustrates the electrode 424 generally aligned with the central longitudinal axis of the shroud 420. However, the proximal end region 431 of the shroud 420 may be offset from the central longitudinal axis of the electrode 424 and the distal end region of the shroud 420.

Additionally, FIG. 29 illustrates the electrosurgical actuator 426, including the actuation button 429, the first power button 427 and the second power button 428 positioned along a surface of the body 416. FIG. 29 further illustrates the shaft 430 aligned with the first magnetic component 480, the second magnetic component 482 and the third magnetic component 484. As described above, a distal end of region of the shaft 430 may be attached to the proximal end region 431 of the shroud 420, while the second magnetic component 482 may be attached to a proximal end region of the shaft 430.

Figure 30:
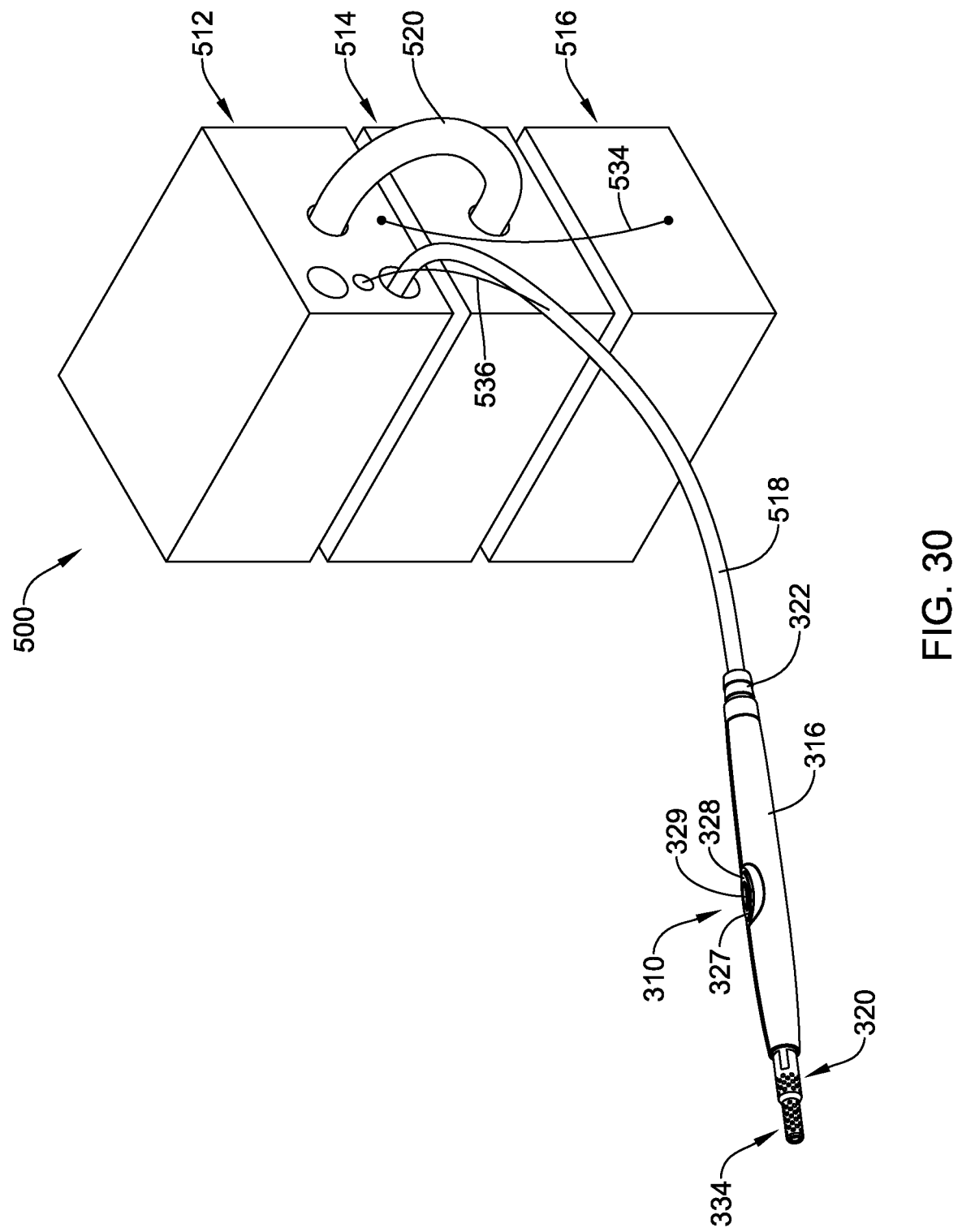
FIG. 30 a schematic illustration of an electrosurgical system including an electrosurgical device coupled to an interface console, a smoke evacuation device and an electrosurgical generator.

FIG. 30 illustrates an electrosurgical system 500. The electrosurgical system 500 may include an interface console 512, a smoke evacuator 514 and/or an electrosurgical generator 516. In some examples, the interface console 512, the smoke evacuator 514 and/or the electrosurgical generator 516 may be separate components positioned in a stacked (or other similar) configuration, such as the configuration illustrated in FIG. 30. It can be appreciated that, in this arrangement, the interface console 512, the smoke evacuator 514 and/or the electrosurgical generator 516 may be decoupled (e.g., disconnected) and utilized with any other component and/or other electrosurgical systems. Other arrangements and/or configurations are also contemplated. For example, the interface console 512, the smoke evacuator 514 and/or the electrosurgical generator 516 may be distinct components that are integrated into a single, unified housing.

FIG. 30 further illustrates the electrosurgical system 500 may further include the electrosurgical device 310. However, this is not intended to be limiting. Rather, it is contemplated that electrosurgical system 500 (and any components thereof) may include and be utilized with any of the example electrosurgical devices described herein. FIG. 30 illustrates the electrosurgical device 310 may be coupled to the interface console 512. As will be described in greater detail below, in some examples the electrosurgical device 310 may be connected directly to the smoke evacuator 514 and the electrosurgical generator 516. Additionally, in other examples the electrosurgical device 310 may be connected directly to the electrosurgical generator 516.

Figure 31A:
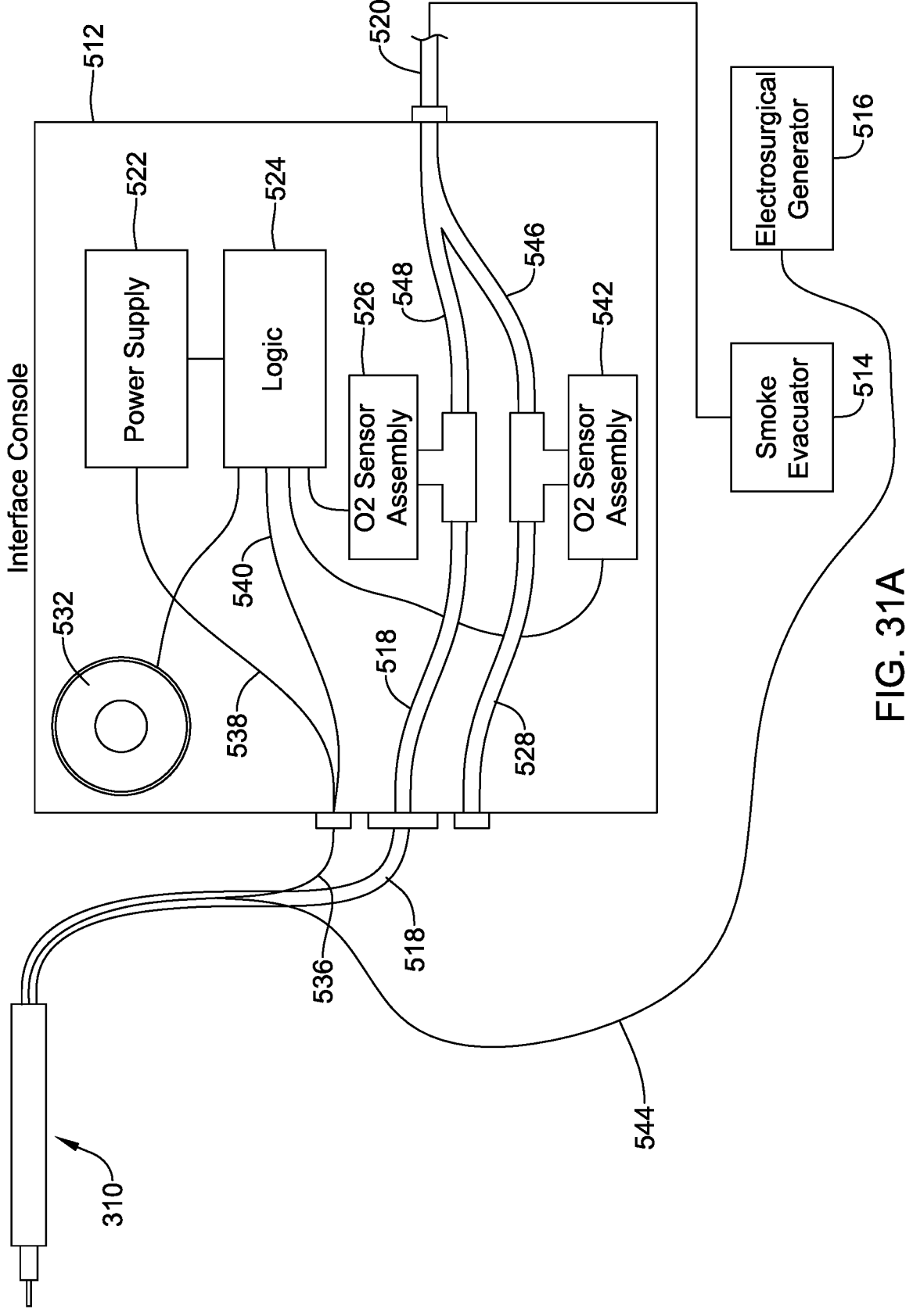
FIG. 31A is another schematic illustration of an electrosurgical device coupled to an interface console, a smoke evacuation device and an electrosurgical generator.
Figure 31B:
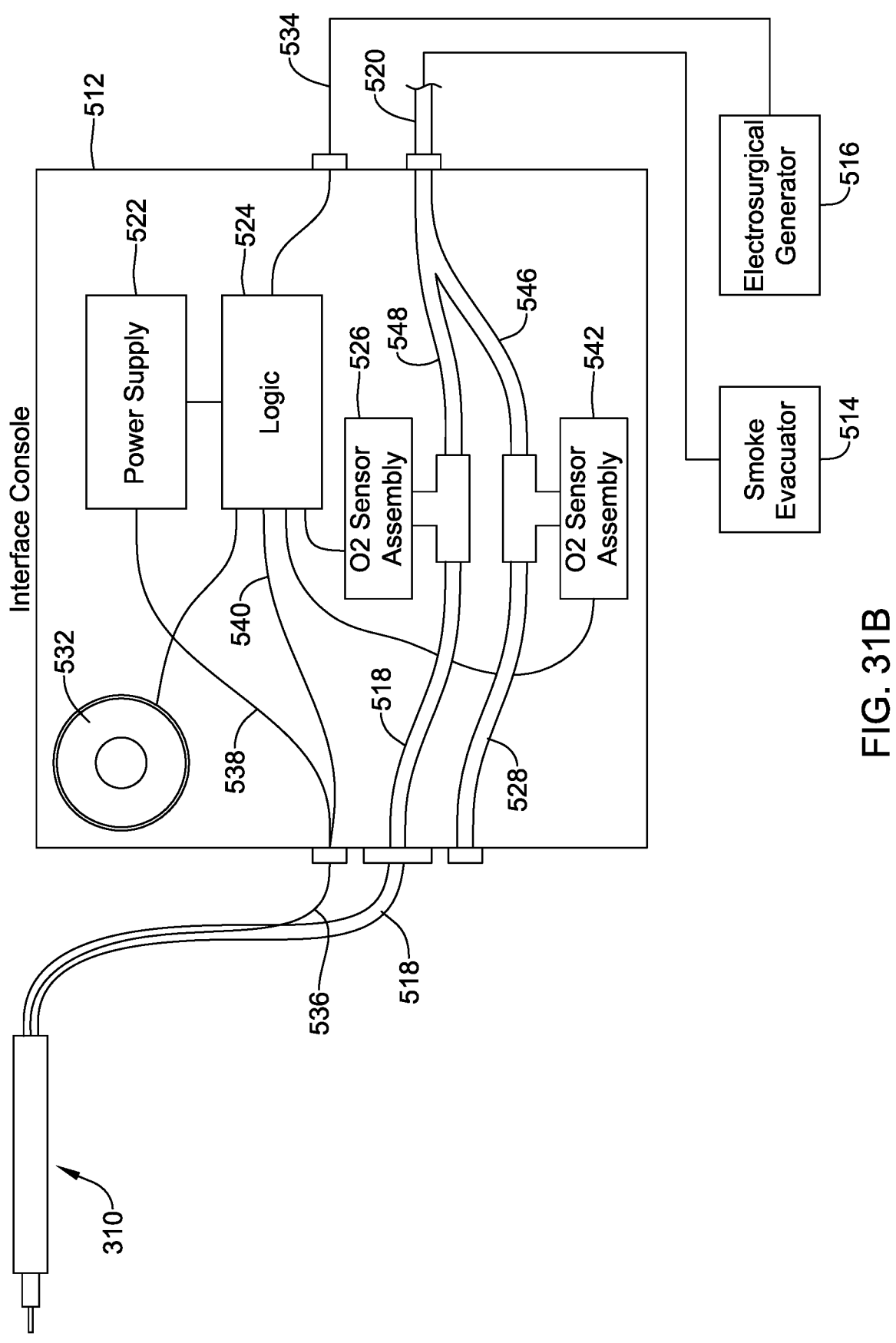
FIG. 31B is another schematic illustration of an electrosurgical device coupled to an interface console, a smoke evacuation device and an electrosurgical generator.

As will be described in greater detail below, the electrosurgical device 310 may be coupled to the interface console 512, the smoke evacuator 514 and/or the electrosurgical generator 516 via a connecting tube 518 and/or one or more connecting wire bundles (e.g., a first connecting wire bundle 536). In some instances, the connecting wire bundle 536 may include one or more wires bundled together which extend from the interface console 512 to the electrosurgical device 310. Referring to FIGS. 31A-31B, the connecting wire bundle 536 may include the electrical wire 538 and the electrical wire 540. It can be appreciated that in instances where the electrosurgical device 310 is connected directly to the electrosurgical generator 516, the system 500 may include an additional connecting wire connecting the electrosurgical device 310 directly to the electrosurgical generator 516.

In some examples, the connecting tube 518 may be referred to as a utility cable and/or a smoke evacuation line. Further, FIG. 30 illustrates that the interface console 512 may be coupled to the smoke evacuator 514 via an evacuation tube 520. Further yet, the interface console 512 may be coupled to the electrosurgical generator 516 via an electrical wire 534.

As described above, the electrosurgical device 310 shown in FIG. 30 may be used to cut or coagulate tissue during a medical surgery. However, the heat generated by the electrode 324 (e.g., shown in FIG. 19) of the electrosurgical device 310 may create surgical smoke, which may contain vaporized tissue particles, pathogens, toxic gases, etc. Therefore, protective measures may need to be taken to prevent the inhalation of the surgical smoke. Accordingly, the electrosurgical system 500 may utilize the smoke evacuator 514 to remove surgical smoke during a medical procedure. The smoke evacuator 514 may include a vacuum pump and/or a filter that captures and purifies surgical smoke generated during a medical surgery. Additionally, in some instances the smoke evacuator 514 may include a vacuum pump which generates negative pressure to evacuate smoke, etc., it is also contemplated that the system 500 may also include a separate device or component which generates negative pressure. Further, in some instances the system 500 may include a separate device which generates negative pressure while the smoke evacuator may not generate negative pressure. In yet other instances, both the smoke evacuator and a separate device may generate negative pressure.

FIG. 30 illustrates that the electrosurgical device 310 may include one or more apertures 334 positioned along the distal end of a shroud 320 of the electrosurgical device 310. Additionally, the electrosurgical device 310 may include a proximal connector 322 positioned along a proximal end region of the body 316 of the electrosurgical device 310. In some examples, the shroud 320 (including the apertures 334), the electrosurgical electrode 324 (positioned within the shroud 320 in FIG. 30) and the body 316 may be referred to as an electrosurgical handpiece.

As described above, the electrosurgical device 310 may include a fluid pathway extending from the apertures 334 into the lumen of the shroud 320, through the lumen of the shroud 320 and the lumen of the body 316, through the lumen of the proximal connector 322, through the connecting tube 518 and into the interface console 512. Additionally, and as will be described in detail below with respect to FIG. 31, this fluid pathway may further pass through an oxygen sensing assembly 526 (e.g., shown in FIG. 31) located in the interface console 512 before exiting the interface console 512 and passing into the smoke evacuator 514 via the evacuation tube 520. Hence, to evacuate smoke during a medical surgery, the smoke evacuator 514 may generate negative pressure (via a vacuum pump located in the smoke evacuator 514) which pulls smoke through the fluid pathway (including the oxygen sensing assembly 526) to the smoke evacuator 514.

Additionally, it can be appreciated the electrosurgical generator 516 may be coupled to the interface console 512 via an electrical wire 534. In some examples, the electrosurgical generator 516 may provide electrical energy to the electrode 324 (positioned within the shroud 320 in FIG. 30) of the electrosurgical device 310. In some examples, the electrical energy provided by the electrosurgical generator 516 may be sent directly to the electrosurgical device 310 to energize the electrode 324. However, in other examples, the electrical energy provided by the electrosurgical generator 516 may be initially sent to the interface console 512 whereby it subsequently travels to the electrosurgical device 310 to energize the electrode 324.

FIG. 31A is a schematic illustration showing an example interface console 512 (including several components positioned within the interface console 512), the electrosurgical device 310, the smoke evacuator 514 coupled to the interface console 512, and the electrosurgical generator 516 coupled directly to the electrosurgical device 310.

FIG. 31A illustrates that, in some examples, the interface console 512 may include a logic component 524 (e.g., a circuit board, logic processor, logic chip, etc.), an alarm 532, a power supply 522, a first oxygen sensing assembly 526 and a second oxygen sensing assembly 542. The alarm 532 may include an audible or visual indicator which alerts the user of the electrosurgical device 310 of a hazardous condition existing within the operating field. The logic component 524 may include logic circuitry (e.g., processing algorithms) that may control processes such as the actuation of the shroud 320 between a first position and a second position (via communication with the first oxygen sensing assembly 526, the second oxygen sensing assembly 542 and/or the power supply 522), controlling one or more lights located on the electrosurgical device 310 and/or the triggering of the audible or visual alarm 532 (in response to hazardous conditions present in the operating field).

As described herein, depending on the type of medical procedure being performed, operation of the electrosurgical device 310 may include energizing the electrosurgical electrode 324 to either cut or coagulate tissue. Further, as described above, the electrosurgical generator 516 (via the electrosurgical device 310) may permit a user to actuate a first power button 327 to cut tissue while, alternatively, permitting the user to actuate a second power button 328 to provide a different profile of energy (relative to the energy delivered to cut tissue) to coagulate tissue. Accordingly, the first power button 327 and the second power button 328 of the electrosurgical device 310 may be coupled to the electrosurgical generator 516 via the second connecting wire 544.

Additionally, it can be appreciated that, when a user actuates either the first power button 327 (to cut tissue) or the second power button 328 (to coagulate tissue), a signal may be sent from the electrosurgical device 310 to the logic component 524, whereby the logic component 524 communicates with the power supply 522 to provide energy to actuate the shroud 320.

It can be appreciated that to cut or coagulate tissue, the shroud 320 of the electrode surgical device 310 needs to be in a retracted position to expose the electrode 324 of the electrosurgical device 310. It can be further appreciated that, in various embodiments of the electrosurgical device 310 (including the electrosurgical device 310 and the electrosurgical device 410), a user may actuate the shroud 320 by depressing an actuation button 329 located on the electrosurgical device 310 (or by depressing an actuation button 429 on device 410). As discussed herein, depressing the actuation button 329 may send a signal to the logic component 524 indicating that a first magnetic component 380 and a third magnetic component 384 of the electrosurgical device 310 need to be momentarily energized (e.g., electrical power needs to be supplied to the first magnetic component 380 and the third magnetic component 384 of the electrosurgical device 310 to actuate the shroud 320). Accordingly, the logic component 524 may send a signal to the power supply 522, which, in turn, sends an electrical current to the first magnetic component 380 and the third magnetic component 384 via the electrical wire 538 (which may be part of the electrical wire bundle 536).

However, as described above, after the first magnetic component 380 and the third magnetic component 384 having been momentarily energized (thereby translating the shroud 320 from a first position to a second position) the logic component 524 may then send another signal to the power supply 522 to stop the flow of the electrical current to the first magnetic component 380 and the third magnetic component 384. It is noted that the logic component 524 may send the signal to the power supply 522 to stop the flow of electrical energy to the first magnetic component 380 and the third magnetic component 384 (even though the user continues to depress the actuation button 329). It is further noted that the shroud 320 remains held in the second position (e.g., the retracted position) due to the magnetic interaction of the second magnetic component 382 and the third magnetic component 384 as the logic component 524 has stopped the flow of electrical current to the first magnetic component 380 and the third magnetic component 384.

Additionally, it can be appreciated that when the user releases the actuation button 329, the logic component 524 may send a signal to the power supply 522 to send an electrical current back to the first magnetic component 380 and the third magnetic component 384 (even if the first power button 327 or the second power button 328 remain depressed by the user). Accordingly, the flow of electrical energy back to the first magnetic component 380 and the third magnetic component 384 may reenergize the first magnetic component 380 and the third magnetic component 384, thereby translating the shroud 320 from the second position back to the first position, in which it is covering the electrode 324.

It can be appreciated from the above discussion that the electrical energy utilized to power the first magnetic component 380 and the third magnetic component 384 may be derived from the power supply 522 located in the interface console 512 while the electrical energy utilized to power the electrode 324 may be derived from the electrosurgical generator 516. However, it is contemplated that, in other examples, the electrical energy utilized to power the first magnetic component 380 and the third magnetic component 384 may be derived from the electrosurgical generator 516 or some combination of the electrosurgical generator 516 and the power supply 522. In yet other examples, it is contemplated that the electrical energy utilized to power the electrode 324 may be derived from the power supply 522 or some combination of the electrosurgical generator 516 and the power supply 522.

As described herein, the interface console 512 may not only include the logic component 524 and the power supply 522, but may also include a first oxygen sensing assembly 526 and a second oxygen sensing assembly 542. Each of the oxygen sensing assemblies 526/542 may include an oxygen sensor 526/542 and a portion of the logic component 524. In other words, the oxygen sensing assemblies 526/542 may each include an oxygen sensor 526/542 in addition to some portion of the processing algorithms that may be part of the logic component 524. Further, in some examples, the logic component 524 and the first oxygen sensing assembly 526, the second oxygen sensing assembly 542 or both the first oxygen sensing assembly 526 and the second oxygen sensing assembly 542 may be integrated into one component. However, this is not intended to be limiting. In some examples, the first oxygen sensing assembly 526, the second oxygen sensing assembly 542 or both the first oxygen sensing assembly 526 and the second oxygen sensing assembly 542 may only include an oxygen sensor.

As described above, while in use, the electrode 324 of the electrosurgical device 310 may generate heat, and therefore, in the presence of certain conditions, may inadvertently cause a fire. For example, the electrode 324 of the electrosurgical device 310 may more susceptible to start a fire when in the presence of an increased level of oxygen. Therefore, it may be desirable to design the electrosurgical system 500 to continuously sample the oxygen level in the operating field (or any given oxygen sampling field), sense an increased level of oxygen (relative to a predetermined threshold) and send signals to various components of the electrosurgical system 500 in response to the increased level of oxygen.

FIG. 31A further illustrates that the oxygen sensing assembly 526 may be positioned in line with the connecting tube 518 and the evacuation tube 520. As described above, the oxygen sensing assembly 526 may continually monitor the oxygen level in the operating field (or any given oxygen sampling field), and compare the oxygen level to a threshold limit. For example, the oxygen sensing assembly 526 may sample the oxygen level in the operating field and communicate those levels with the logic component 524. Further, if the logic component 524 determines that the presence of increased oxygen in the operating field exceeds a threshold limit, it may send one or more signals to actuate the shroud 320 to cover the electrode 324 and/or maintain the shroud 320 in a position in which it is covering the electrode 324 (e.g., the logic component 524 may actuate the shroud 320 to cover the electrode 324 and continue to prevent the actuation of the shroud 320 until oxygen levels have been reduced below the threshold condition).

Additionally, in some examples, after the logic component 524 determines that the oxygen level has exceeded the threshold limit, the logic component 524 may send a signal to the power supply 522 which subsequently sends an electrical current to the first magnetic component 380 and the third magnetic component 384. As discussed above, sending the electrical current to the first magnetic component 380 and the third magnetic component 384 may translate the shroud 320 from the second position (e.g., a retracted position) to the first position, in which the shroud 320 is covering the electrode 324. Additionally, in some examples, the logic component 524 may not only translate the shroud 320 to cover the electrode 324, but it may also prevent further actuation of the shroud 320 from the first position to the second position until oxygen levels have been reduced below the threshold condition.

In some examples, such as the example illustrated in FIG. 31A, the electrosurgical generator 516 may continue to provide energy to the electrode 324 and or the electrosurgical handpiece despite the shroud 320 having been translated to cover the electrode 324 in response to oxygen levels exceeding the threshold limit. For example, after determining the presence of threshold-exceeding oxygen levels, the logic component 524 may actuate the shroud 320 to the first position while the electrosurgical generator continues to provide energy to the electrode 324. In other words, the electrode 324 may continue to receive electrical energy from the electrosurgical generator 516 despite being covered by the shroud 320, in response to the presence of threshold-exceeding oxygen levels. Further, the electrode 324 may continue to receive energy even if the logic component 524 is maintaining the shroud 320 in the first position.

Additionally, it can be appreciated that when the oxygen level is above the predetermined threshold, the logic component 524 may send a signal to the alarm 532, which may provide a visual indication (e.g., via an LED light or similar device) of the threshold-exceeding condition and/or may provide an audible indication (e.g., audible beep, etc.) of the threshold-exceeding condition.

FIG. 31A further illustrates that the interface console 512 may also include an auxiliary line 528. The auxiliary line 528 may permit the attachment of an auxiliary device (e.g., a facemask) to the interface console 512. Additionally, FIG. 31A illustrates that the second oxygen sensing assembly 542 may be positioned in line with the connecting tube 528 and the evacuation tube 520 (as shown in FIG. 31A, the first oxygen assembly 526 may include a first exit tube 548 which merges with a second exit tube 546 of the second oxygen assembly 542 which are both in communication with the evacuation tube 520). It can be appreciated that the second oxygen sensing assembly 542 may continually monitor the oxygen level in the oxygen sampling field (e.g., a patient facemask) and communicate with the logic component 524 to compare oxygen levels to a threshold limit. If oxygen levels exceed the threshold limit, the logic component 524 may send one or more signals to actuate the shroud 320 to cover the electrode 324 and/or maintain the shroud 320 in a position in which it is covering the electrode 324 (e.g., the logic component 524 may actuate the shroud 320 to cover the electrode 324 and continue to prevent the actuation of the shroud 320 until oxygen levels have been reduced below the threshold condition).

FIG. 31B is a schematic illustration showing another example configuration of the interface console 512 (including several components positioned within the interface console 512), the electrosurgical device 310 coupled to the interface console 512, the smoke evacuator 514 coupled to the interface console 512, and the electrosurgical generator 516 coupled to the interface console 512.

FIG. 31B illustrates that, in some examples, the interface console 512 may include a logic component 524 (e.g., a circuit board, logic processor, logic chip, etc.) coupled to the electrosurgical device 310, an alarm 532, the electrosurgical generator 516 (via the electrical wire 534), a power supply 522, a first oxygen sensing assembly 526 and a second oxygen sensing assembly 542. The alarm 532 may include an audible or visual indicator which alerts the user of the electrosurgical device 310 of a hazardous condition existing within the operating field. The logic component 524 may include logic circuitry (e.g., processing algorithms) that may control processes such as the actuation of the shroud 320 between a first position and a second position (via communication with the first oxygen sensing assembly 526, the second oxygen assembly 542 and/or the power supply 522) and/or the triggering of the audible or visual alarm 532 (in response to hazardous conditions present in the operating field).

As described herein, depending on the type of medical surgery being performed, operation of the electrosurgical device 310 may include energizing the electrosurgical electrode 324 to either cut or coagulate tissue. Further, as described above, the electrosurgical device 310 may permit a user to actuate a first power button 327 to cut tissue while, alternatively, permitting the user to actuate a second power button 328 to provide a different profile of energy (relative to the energy delivered to cut tissue) to coagulate tissue. Accordingly, the first power button 327 and the second power button 328 of the electrosurgical device 310 may be coupled to the logic component 524 via an electrical wire 540 (which may be part of the connecting wire bundle 536 that attaches to the logic component 524).

Additionally, as described above, the logic component 524 may also be coupled to the electrosurgical generator 516 via an electrical wire 534. Therefore, it can be appreciated that, when a user actuates either the first power button 327 (to cut) or the second power button 328 (to coagulate), an energy profile corresponding to that selection is delivered to the electrode 324.

It can be appreciated that to cut or coagulate tissue, the shroud 320 of the electrode surgical device 310 needs to be in a retracted position to expose the electrode 324 of the electrosurgical device 310. It can be further appreciated that, in various embodiments of the electrosurgical device 310 (including the electrosurgical device 310 and the electrosurgical device 410), a user may actuate the shroud 320 by depressing an actuation button 329 located on the electrosurgical device 310. Further, depressing the actuation button 329 may send a signal to the logic component 524 indicating that a first magnetic component 380 and a third magnetic component 384 of the electrosurgical device 310 need to be momentarily energized (e.g., energy needs to be supplied to the first magnetic component 380 and the third magnetic component 384 of the electrosurgical device 310 to actuate the shroud 320). Accordingly, the logic component 524 may send a signal to the power supply 522, which, in turn, sends an electrical current to the first magnetic component 380 and the third magnetic component 384 via the electrical wire 538.

However, as described above, after the first magnetic component 380 and the third magnetic component 384 having been momentarily energized (thereby translating the shroud 320 from a first position to a second position) the logic component 524 may then send another signal to the power supply 522 to stop the flow of the electrical current to the first magnetic component 380 and the third magnetic component 384. It is noted that the logic component 524 may send the signal to the power supply 522 to stop the flow of electrical energy to the first magnetic component 380 and the third magnetic component 384 (even though the user continues to depress the actuation button 329). It is further noted that the shroud 320 remains held in the second position (e.g., the retracted position) due to the magnetic interaction of the second magnetic component 382 and the third magnetic component 384 as the logic component 524 has stopped the flow of electrical current to the first magnetic component 380 and the third magnetic component 384.

Additionally, it can be appreciated that when the user releases the actuation button 329, the logic component 524 may send a signal to the power supply 522 to send an electrical current back to the first magnetic component 380 and the third magnetic component 384 (even if the first power button 327 or the second power button 328 remain depressed by the user). Accordingly, the flow of electrical energy back to the first magnetic component 380 and the third magnetic component 384 may reenergize the first magnetic component 380 and the third magnetic component 384, thereby translating the shroud 320 from the second position back to the first position, in which it is covering the electrode 324.

It can be appreciated from the above discussion that the electrical energy utilized to power the first magnetic component 380 and the third magnetic component 384 may be derived from the power supply 522 located in the interface console 512 while the electrical energy utilized to power the electrode 324 may be derived from the electrosurgical generator 516. However, it is contemplated that, in other examples, the electrical energy utilized to power the first magnetic component 380 and the third magnetic component 384 may be derived from the electrosurgical generator 516 or some combination of the electrosurgical generator 516 and the power supply 522. In yet other examples, it is contemplated that the electrical energy utilized to power the electrode 324 may be derived from the power supply 522 or some combination of the electrosurgical generator 516 and the power supply 522.

As described above, the interface console 512 may not only include the logic component 524 and the power supply 522 but may also include a first oxygen sensing assembly 526 and a second oxygen sensing assembly 542. Each of the oxygen sensing assemblies 526/542 may include an oxygen sensor 526/542 and a portion of the logic component 524. In other words, the oxygen sensing assemblies 526/542 may each include an oxygen sensor 526/542 in addition to some portion of the processing algorithms that may be part of the logic component 524. However, this is not intended to be limiting. In some examples, the oxygen sensing assemblies 526/542 may only include the oxygen sensor.

As described above, while in use, the electrode 324 of the electrosurgical device 310 may generate heat, and therefore, in the presence of certain conditions, may inadvertently cause a fire or unintentional bodily harm. For example, the electrode 324 of the electrosurgical device 310 may be more susceptible to start a fire when in the presence of an increased level of the oxygen. Therefore, it may be desirable to design the electrosurgical system 500 to continuously sample the oxygen level in the operating field (or any given oxygen sampling field), sense an increased level of oxygen (relative to a predetermined threshold) and send signals to various components of the electrosurgical system 500 in response to the increased level of oxygen.

FIG. 31B further illustrates that the oxygen sensing assembly 526 may be positioned in line with the connecting tube 518 and the evacuation tube 520. As described above, the oxygen sensing assembly 526 may continually monitor the oxygen level in the operating field and compare the detected oxygen level to a threshold limit. For example, the oxygen sensing assembly 526 may sample the oxygen level in the operating field and communicate those levels with the logic component 524. Further, if the logic component 524 determines that the presence of increased oxygen in the operating field exceeds a threshold limit, it may send one or more signals to actuate the shroud 520 to cover the electrode 324 and/or maintain the shroud 520 in a position in which it is covering the electrode 324 (e.g., the logic component 524 may actuate the shroud 320 to cover the electrode 324 and continue to prevent the actuation of the shroud 320 until oxygen levels have been reduced below the threshold condition).

Additionally, in some examples, after the logic component 524 determines the oxygen level has exceeded a threshold limit, the logic component 524 may stop the flow of electrical energy from the electrosurgical generator 516 to the electrode 324 (even though the shroud 320 is retracted and the electrosurgical device 310 is being utilized to cut or coagulate tissue). In other words, in the presence of hazardous oxygen levels, the logic component 524 may stop the flow of electrical energy from the electrosurgical generator 516 to the electrode 324 despite a user continuing to depress the actuation button 329, the first power button 327 and/or the second power button 328.

Additionally, in some examples, after the logic component 524 determines that the oxygen level has exceeded the threshold limit, the logic component 524 may send a signal to the power supply 522 which subsequently sends an electrical current to the first magnetic component 380 and the third magnetic component 384. As discussed above, sending the electrical current to the first magnetic component 380 and the third magnetic component 384 may translate the shroud 320 from the second position (e.g., a retracted position) to the first position, in which the shroud 320 is covering the electrode 324. Additionally, in some examples, the logic component 524 may not only translate the shroud 320 to cover the electrode 324, but it may also prevent further actuation of the shroud 320 from the first position to the second position until oxygen levels have been reduced below the threshold condition.

In some examples, the logic component 524 may continue to provide energy to the electrode 324 and or the electrosurgical handpiece despite having translated the shroud 320 to cover the electrode 324 in response to oxygen levels exceeding the threshold limit. For example, after determining the presence of threshold-exceeding oxygen levels, the logic component 524 may actuate the shroud 320 to the first position while also continuing to provide energy to the electrode 324. In other words, the electrode 324 may continue to receive electrical energy from the electrosurgical generator 516 despite being covered by the shroud 320, in response to the presence of threshold-exceeding oxygen levels. Further, the electrode 324 may continue to receive energy even if the logic component 524 is maintaining the shroud 320 in the first position.

Additionally, it can be appreciated that when detected oxygen levels exceed a threshold limit, the logic component 524 may send a signal to the alarm 532, which may provide a visual indication (e.g., via an LED light or similar device) of the threshold-exceeding condition and/or may provide an audible indication (e.g., audible beep, etc.) of the threshold-exceeding condition.

FIG. 31B further illustrates that the interface console 512 may also include an auxiliary line 528. The auxiliary line 528 may permit the attachment of an auxiliary device (e.g., a facemask) to the interface console 512. Additionally, FIG. 31B illustrates that the second oxygen sensing assembly 542 may be positioned in line with the connecting tube 528 and the evacuation tube 520 (as shown in FIG. 31B, the first oxygen assembly 526 may include a first exit tube 548 which merges with a second exit tube 546 of the second oxygen assembly 542 which are both in communication with the evacuation tube 520. It can be appreciated that the second oxygen sensing assembly 542 may continually monitor the oxygen level in the oxygen sampling field (e.g., a patient facemask) and communicate with the logic component 524 to compare oxygen levels to a threshold limit. If oxygen levels exceed the threshold limit, the logic component 524 may send one or more signals to actuate the shroud 320 to cover the electrode 324 and/or maintain the shroud 320 in a position in which it is covering the electrode 324 (e.g., the logic component 524 may actuate the shroud 320 to cover the electrode 324 and continue to prevent the actuation of the shroud 320 until oxygen levels have been reduced below the threshold condition).

Additionally, it can be appreciated that any of the electrosurgical devices disclosed herein may include one of more lights (e.g., LED or similar). For example, electrosurgical devices disclosed herein may include one or more lights designed to illuminate a portion of the target operating site. In some examples, the lights (e.g., LED) may be powered by the power supply 522. Additionally, in some examples, the electrosurgical devices disclosed herein may include a separate button disposed along the electrosurgical device which sends a signal to the power supply to power the lights on the electrosurgical device.

Additionally, it can be appreciated that the electrosurgical devices disclosed herein may include a light (e.g., LED or similar) disposed along the electrosurgical device which is designed to illuminate when the detected level of oxygen has exceeded the threshold limit. The light may be powered by the power supply 522. Accordingly, it can be appreciated that the light may be connected to both the logic component 524 and/or the power supply 522. In this embodiment, the light may illuminate simultaneously with the alarm 532.

In addition to the above examples which include electrosurgical devices having a shroud which is actuatable relative to a stationary electrode, it is further contemplated that any of the example electrosurgical devices disclosed herein may be designed to include an electrode which is actuatable relative to a stationary shroud. In other words, one of skill in the art may contemplate electrosurgical pens which are designed to include an electrode which translates relative to a stationary shroud (e.g., a shroud which is fixedly attached to the body of the electrosurgical pen).

Figure 32:
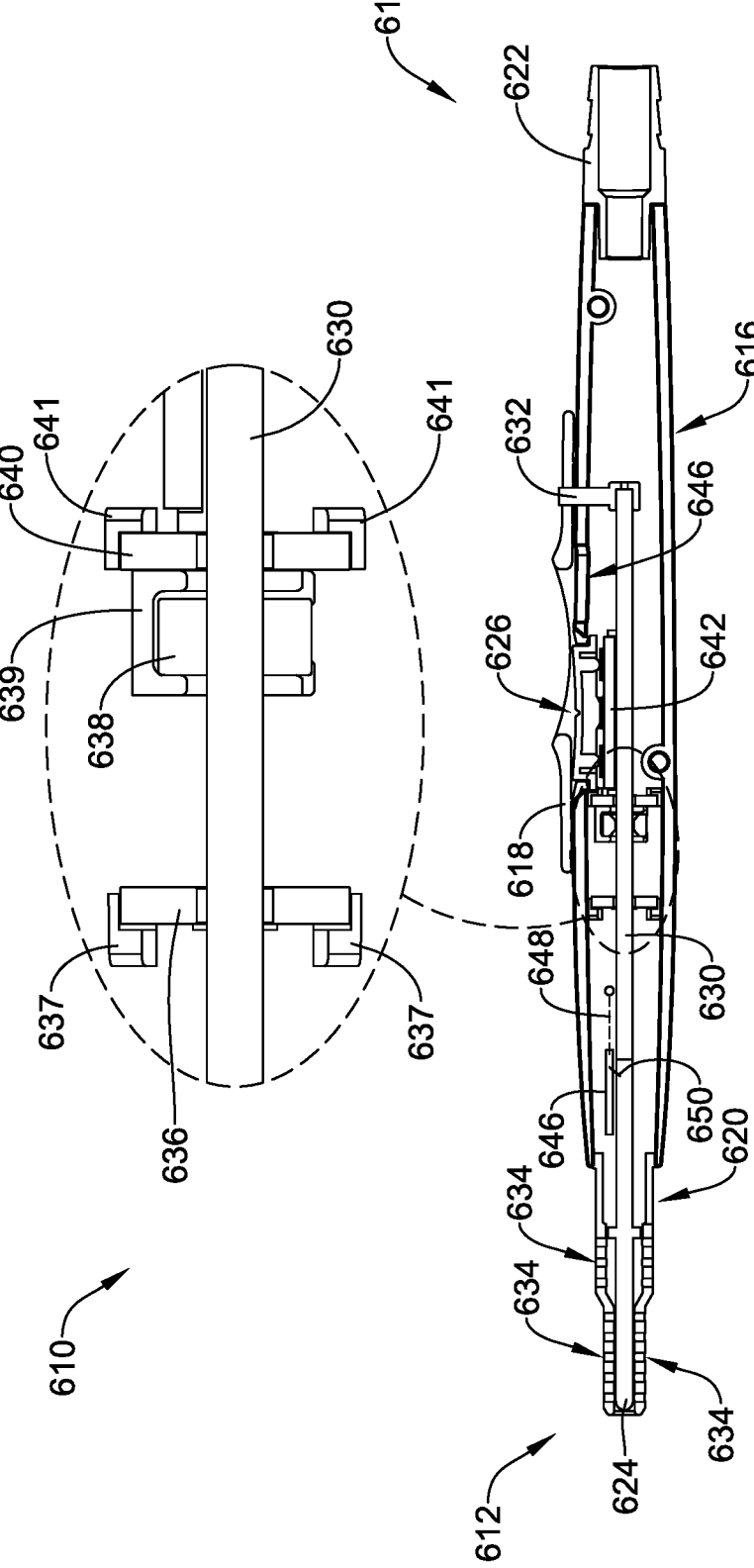
FIG. 32 illustrates an example electrosurgical device in a first position.

For example, FIG. 32 illustrates a cross-sectional view of an example electrosurgical device 610. FIG. 32 illustrates that the electrosurgical device 610 may include a moveable electrode 624 in a first position, whereby the distal end of the moveable electrode 624 is positioned within the lumen of a stationary shroud 620. It can be appreciated the shroud 620 may be fixedly attached to the body 616 of the electrosurgical device 610. In other words, the shroud 620 shown in FIG. 32 is not translatable relative to the body 616 of the electrosurgical device 610.

FIG. 32 further illustrates that proximal end of the electrode 624 may be coupled to a distal end of a shaft 630. Further yet, FIG. 32 illustrates that a portion of the shaft 630 may be coupled to a linkage 632. Additionally, the linkage 632 may be coupled to a sliding cover 618. FIG. 32 illustrates that the sliding cover 618 may cover at least a portion of a switch 626, thereby preventing actuation of the switch 626 to energize the electrode 624. The position of the sliding cover 618 shown in FIG. 32 illustrates a configuration in which the sliding cover 618 is in a proximal-most position relative to the body 616.

The electrosurgical device 610 may be designed such that actuation (e.g., sliding, etc.) of the sliding cover 618 may simultaneously translate the electrode 624. For example, actuation of the sliding cover 618 in a proximal-to-distal direction will simultaneously translate the electrode 624 in a proximal-to-distal direction. Similarly, actuation of the sliding cover 618 in a distal-to-proximal direction will actuate the electrode 624 in a distal-to-proximal direction. The simultaneous actuation of the sliding cover 618 and the electrode 624 occurs because the sliding cover 618 and the electrode 624 are attached to one another via the combination shaft 630 and the linkage 632. As shown in FIG. 32, the linkage 632 may generally extend vertically, thereby connecting the shaft 630 to the sliding cover 618.

Further, FIG. 32 illustrates that the linkage 632 may pass from an interior cavity of the body 616 through an aperture 646 and attach to the proximal end region of the sliding cover 618. It can be appreciated from FIG. 32 that the aperture 646 may extend longitudinally along the body 616 which permits the linkage 632 to shift longitudinally (relative to the body 616) within the aperture 646. Accordingly, to expose the electrode 624 as described above, a user may slide the sliding cover 618 in a proximal-to-distal direction, which also shifts the linkage 632 in a proximal-to-distal direction, which, in turn, advances the shaft 630 and the electrode 624 in a proximal-to-distal direction, thereby advancing the distal end region of the electrode 624 out of the distal end of the shroud 620 (which is held stationary relative to the body 616).

Further, as described above, actuating the sliding cover 618 in a proximal-to-distal direction may also uncover the switch 626, thereby permitting the user to power the electrode 624 to cut and/or coagulate tissue. To energize the electrode 624, energy must be supplied to the electrode 624 from an energy source (e.g., an electrosurgical generator located away from the electrosurgical device 610). FIG. 32 illustrates that both the body 616 and a proximal connector 622 may generally include hollow cavities which may permit one or more electrical wires to extend from the energy source, through the hollow cavities of the proximal connector 622 and/or the body 616, whereby the electrical wires may be attached to a circuit board 642 aligned with the underside of the switch 626.

Further, from the circuit board 642, a conductive member 648 (e.g., conductive wire, flex circuit, metal trace) may extend distally from the circuit board 642 to a conductive element 646 (e.g., band, strip, bar, ribbon, rod) extending along an inner surface of the body 616. As shown in FIG. 32, in some examples, a portion of the conductive member 648 may extend within (or along) one or more cavities in the body 616. One skilled in the art can appreciate that the electrosurgical device 610 may include a variety of wiring configurations which couple the circuit board 642 to the conductive element 646.

Figure 33:
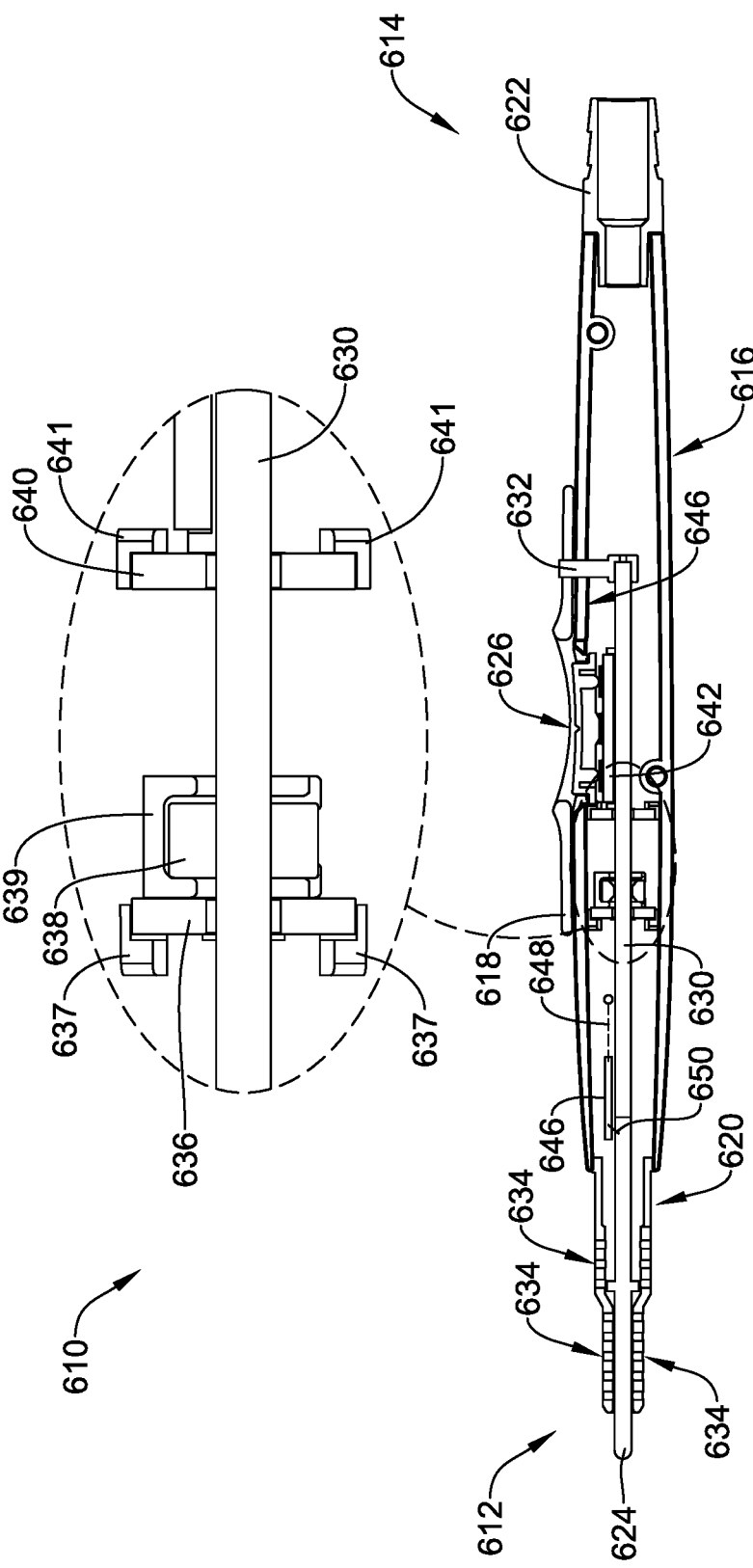
FIG. 33 illustrates the example electrosurgical device shown in FIG. 32 in a second position.

As discussed herein, the conductive element 646 may extend longitudinally along in inner surface of body 616. Additionally, FIG. 32 illustrates that the proximal end region of the electrode 624 may include a conductive projection 650 which is designed to maintain contact with the conductive element 646 as the electrode 624 translates relative to the shroud 620 and body 616. In some instances, the conductive projection 650 may be extend radially away from the electrode 624 such that it is biased in a configuration to maintain continuous electrical contact with the conductive element 646 as the electrode 624 translates relative to the shroud 620 and body 616. For example, FIG. 33 illustrates the electrode 624 being translated in a proximal-to-distal direction such that the distal end region of the electrode 624 extends out of the distal end of the shroud 620. As shown in FIG. 33, the conductive projection 650 maintains electrical contact with the conductive element 646 as the electrode 624 is translated relative to the shroud 620. It can be appreciated that the continuous contact of the conductive projection 650 with the conductive element 646 permits electrical energy to flow from an energy source to the electrode 624 even as the electrode 624 is translating relative to the shroud 620. As discussed herein, this electrical energy may flow from an electrosurgical generator to supply energy to the electrode 624 to cut, coagulate, desiccate, ablate, fulgurate, etc. tissue during an electrosurgery.

FIG. 32 further illustrates that the shroud 620 may include one or more apertures 634 (e.g., holes, openings, fluid pathways, channels, etc.) extending from an outer surface of the shroud 620, through the wall of the shroud 620 to the interior lumen of the shroud 620. The apertures 634 may be designed to permit fluid, air, smoke, etc. to flow from a position outside the shroud 620 through the interior lumen of the shroud 620 (which may be occupied by the electrode 624). Further, the interior lumen of the shroud 620 may be in fluid communication with the hollow cavity (e.g., lumen) of the body 616. Further yet, as described above, the hollow cavity of the body 616 may be in fluid communication with the lumen of the proximal connector 622. It can be appreciated that, in some examples, it may be desirable to pass fluid through the apertures 634 and into the lumen of the shroud 620, along the electrode 624 (where it acts to cool the electrode 624) and out of the electrosurgical device 610 via a continuous fluid pathway extending through the hollow cavity (e.g., inner lumen) of the body 616 and the lumen of the proximal connector 622. Similarly, in some instances, smoke created during the cut/coagulation process may be evacuated from the surgical site through the same fluid pathway.

FIG. 32 further illustrates that the electrosurgical device 610 may include one or more features which are designed to maintain the electrode 624 in either the first (e.g., covered) or second (e.g., extended) position until the user opts to manually actuate the electrode 624 between the first/second position to the second/first position, respectively. Specifically, FIG. 32 includes a magnetic assembly which may maintain the electrode 624 in given position (e.g., positioned within the shroud 620 or extending out of the shroud 620) until the user opts to move the electrode 624 to an alternative position (e.g., positioned within the shroud 620 or extending out of the shroud 620).

The detailed view of FIG. 32 illustrates a magnetic assembly including a first magnetic component 636 held in a stationary position by one or more engagement features 637 located on the interior surface of the body 616. The detailed view of FIG. 32 further illustrates that the magnetic assembly may include a second magnetic component 638 which may be attached to the shaft 630 via a housing 639 (e.g., bracket, attachment structure, support structure, etc.). In other words, the second magnetic component 638 may be supported by the housing 639, whereby the housing 639 may be fixedly attached to the shaft 630 such that actuation of the shaft 630 translates both the housing 639 and the second magnetic component 638 supported by the housing 639.

FIG. 32 further illustrates that each of the first magnetic component 636, the second magnetic component 638 and the housing 639 may include an aperture which is designed to permit the shaft 630 to extend therethrough. As described above, the housing 639 may be fixedly attached to the shaft 630, and therefore, may translate relative to the body 616 and the first magnetic component 636 when the shaft 630 translates (during actuation of the sliding cover 618 and the electrode 624, for example). However, FIG. 32 illustrates that the shaft 630 may pass through an opening in the first magnetic component 636 when translating relative thereto. In other words, the first magnetic component 636 may remain stationary when the shaft 630 and the second magnet component 638 are translated relative to the body 616.

FIG. 32 further illustrates that the electrosurgical device 610 may include a third magnetic component 640 held in a stationary position by one or more engagement features 641 located on the interior surface of the body 616. Like that described above with respect to the first magnetic component 636 and the second magnetic component 638, the second magnetic component 638 may interact with the third magnetic component 640 to maintain a magnetic connection between the second magnetic component 638 and the third magnetic component 640 to maintain the electrode 624 in the first position. For example, actuating the sliding cover 618 in a proximal-to-distal direction will shift the shaft 630 in a proximal-to-distal direction which may disengage the second magnetic component 638 from the third magnet component 640 (because the second magnetic component 638 is fixedly attached to the shaft 630) and may also reposition the second magnetic component 638 such that it interacts with the first magnetic component 636 (this position may correspond to the position in which the electrode 624 is extended out of the distal end of the shroud 620, thereby exposing the electrode 624 as described above).

Additionally, when in the position shown in FIG. 32 (e.g., the first position in which the electrode 624 is positioned within the shroud 620), the second magnetic component 638 may interact with the third magnetic component 640 to maintain the magnetic interaction between the second magnetic component 638 and the third magnetic component 640. It can be appreciated that the magnetic interaction between the second magnetic component 638 and the third magnetic component 640 may maintain the electrode 624 in the first position until a user moves them into a different position, such as when a user translates the sliding cover 618 to disengage the second magnetic component 638 from the third magnetic component 640 and translates the second magnetic component 638 distally to the second position in which it engages the first magnetic component 636, as illustrated in FIG. 33.

As described above, the first magnetic component 636 may be arranged in a distal-most position compared to the second magnetic component 638 and the third magnetic component 640. Further, the second magnetic component 638 may be arranged in an intermediate position between the first magnetic component 636 and the third magnetic component 640. Additionally, the third magnetic component may be arranged in a proximal position to both the first magnetic component 636 and the second magnetic component 638. However, this is not intended to be limiting. Rather, it is contemplated that any of the first magnetic component 636, the second magnetic component 638 and/or the third magnetic component 640 may be positioned in the distal-most, intermediate or proximal positions.

Additionally, it can be appreciated that, in some examples, the electrosurgical device 610 may only include second magnetic component 638 interacting with the third magnetic component 640 to maintain the electrode 624 in the first position, while in other examples, the electrosurgical device 610 may only include the second magnetic component 638 interacting with the first magnetic component 636 to maintain the electrode in the second position. However, in yet other examples, the electrosurgical device 610 may include the first magnetic component 636, the second magnetic component 638 and the third magnetic component 640 which interact to maintain the electrode 624 in the first position or the second position.

Figure 34:
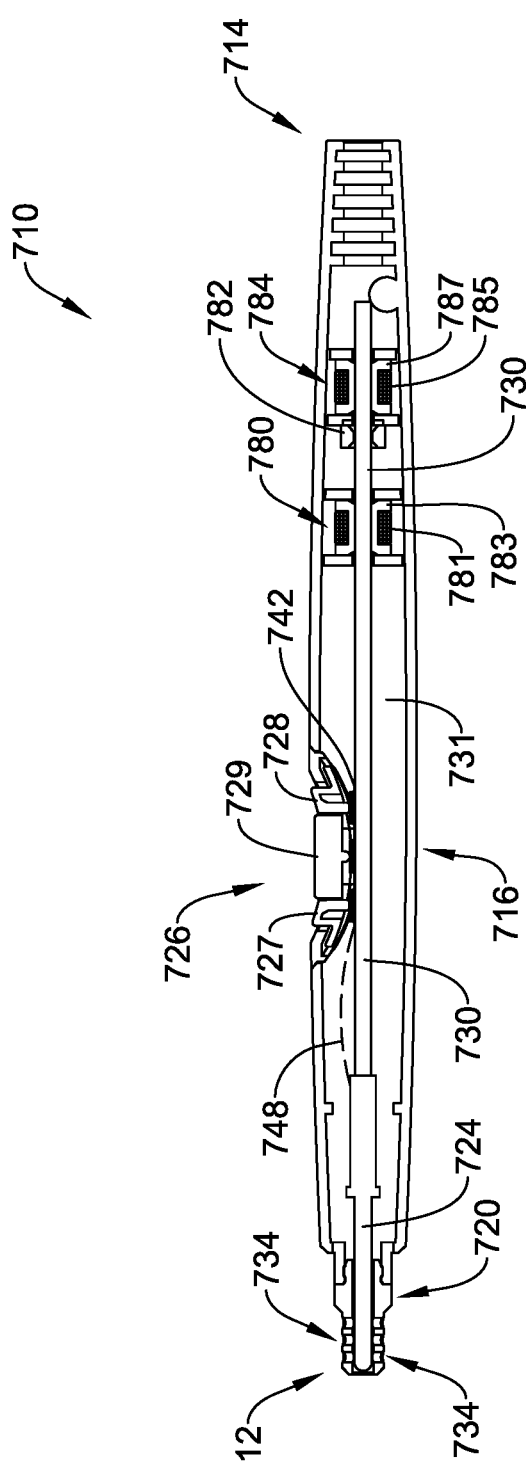
FIG. 34 illustrates an example electrosurgical device in a first position.

FIG. 34 illustrates a cross-sectional view of another example electrosurgical device 710. FIG. 34 illustrates that the electrosurgical device 710 may include an actuatable electrode 724 in a first position, whereby the distal end of the actuatable electrode 724 is positioned within the lumen of a stationary shroud 720. It can be appreciated the shroud 720 may be fixedly attached to the body 716 of the electrosurgical device 710. In other words, the shroud 720 shown in FIG. 34 is not translatable relative to the body 716 of the electrosurgical device 710. Additionally, the electrosurgical device 710 may include an electrosurgical actuator 726 including an actuation button 729. The actuation button 729 may be depressed to translate the electrode 724 from a first position (in which the distal end of the electrode 724 is positioned within the shroud 720 as shown in FIG. 34) to a second position (in which a portion of the electrode 724 is extending out of the distal end of the shroud 720 as shown in FIG. 35).

Additionally, the electrosurgical actuator 726 may also include a first power button 727 positioned distal to the actuation button 729 and a second power button 728 positioned proximal to the actuation button 729. When depressed, each of the first power button 727 and the second power button 728 may engage a circuit board 742 which permits an electrical current to flow from an electrosurgical generator, through a conductive member 748 (e.g., conductive wire, flex circuit, metal trace) and to the electrode 724. In some examples, the first power button 727 may be utilized to cut tissue, while the second power button 728 may be utilized to coagulate tissue. Further, in some examples, the energy delivered to the electrode 724 to cut tissue may be different than the energy delivered to the electrode 724 to coagulate tissue. Further, the operation of the actuation button 729 in conjunction with the first power button 727 and the second power button 728 may be similar to the operation of the actuation button 329, the first power button 327 and the second power button 328 of the electrosurgical device 310 described above.

Additionally, FIG. 34 illustrates that the electrosurgical device 710 may include a second magnetic component 782 attached to a shaft 730. The second magnetic component 782 may magnetically interact with a third magnetic component 784 (as shown in FIG. 34) or a first magnetic component 780 (as shown in FIG. 35). The first magnetic component 780 and the third magnetic component 784 may include electromagnets, while the second magnetic component 782 may include a permanent magnet. However, other configurations are contemplated. For example, as described herein with respect to other electrosurgical devices, any one of the first magnetic component 780, the second magnetic component 782 and the third magnetic component 784 may include a permanent magnet, a magnetic material or an electromagnet arranged in any order with respect to one another. Further, FIG. 34 illustrates that the first magnetic component 780 may include a wire 781 coiled around a magnetic core 783, while the third magnetic component 784 may include a wire 785 coiled around a magnetic core 787.

Figure 35:
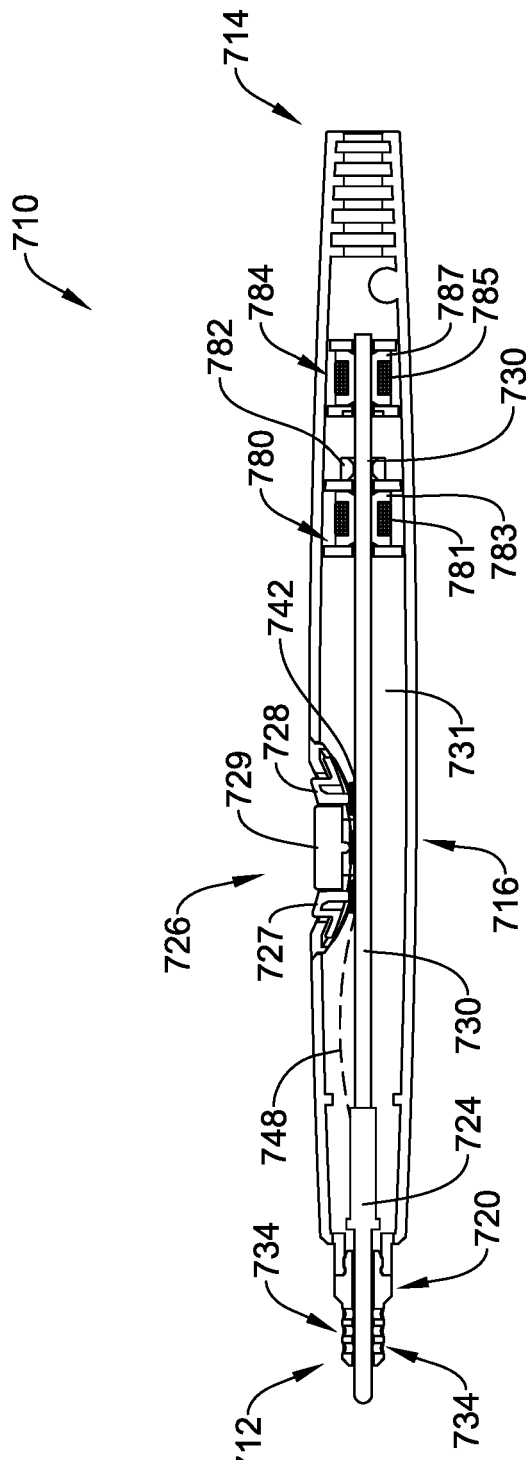
FIG. 35 illustrates the example electrosurgical device shown in FIG. 34 in a second position.

It can be appreciated that depressing the actuation button 729 may send momentary electrical currents to the first magnetic component 780 and the third magnetic component 784, thereby creating magnetic fields in both the first magnetic core 783 and the third magnetic core 787 which may either repel or attract the second magnetic component 782 to translate the electrode 724 from a first position (in which it is positioned within the shroud 720 and body 716 as shown in FIG. 34) to a second position (in which it is extended out of the distal end of the shroud as shown in FIG. 35). Release of the actuation button 729 may reverse the magnetic fields in the first magnetic component 780 and the third magnetic component 784, thereby translating the second magnetic component 782 and the electrode 724 from the second position back to the first position (thereby positioning the electrode 724 within the shroud 720 and body 716 when a user releases the actuation button 729).

It can be appreciated that the circuit board 742 shown in FIG. 34 may be coupled to one or more wires which may be further attached to an electrosurgical generator. Additionally, the circuit board 742 and/or the electrosurgical generator may be coupled to the electrode via the conductive member 748, which may transfer an electrical current from the circuit board 742 and/or the electrosurgical generator to energize the electrode 724 to cut, coagulate, desiccate, ablate, fulgurate, etc. tissue during the electrosurgery. It can be appreciated that, in some examples, the conductive member 748 may be coupled to the electrosurgical generator via the circuit board 742, while in other examples the conductive member 748 may be directly coupled to the electrosurgical generator via one or more conductive wires. It can be further appreciated that the conductive member 748 may include enough length to accommodate the translation of the electrode 724 between the first position and the second position, as described above.

Like that described above with respect to other electrosurgical devices, FIG. 34 further illustrates that the shroud 720 may include one or more apertures 734 (e.g., holes, openings, fluid pathways, channels, etc.) extending from an outer surface of the shroud 720, through the wall of the shroud 720 to an inner lumen of the shroud 720. The apertures 734 may be designed to permit fluid, air, smoke, etc. to flow from a position outside the shroud 720 into the inner lumen of the shroud 720 (which may be occupied by the electrode 724). Further, the inner lumen of the shroud 720 may be in fluid communication with the cavity of the body 716.

The materials that can be used for the various components of the electrosurgical devices disclosed herein may include those commonly associated with medical devices.

The electrosurgical devices may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An electrocautery pencil, comprising:
a body;
a non-movable monopolar electrocautery electrode fixedly secured to the body, the non-moveable monopolar electrocautery electrode including a distal tip;
a heat shroud defining an internal lumen and a distal end, the heat shroud being translatable relative to the non-moveable monopolar electrocautery electrode between a first position wherein the distal tip of the non-movable monopolar electrocautery electrode is disposed entirely within the internal lumen and proximal to the distal end of the heat shroud, and a second position wherein the distal tip of the non-moveable monopolar electrocautery electrode is disposed distal to the distal end of the heat shroud, and wherein the heat shroud is constructed of a heat-resistant material configured to shield the distal tip of the non-movable monopolar electrocautery electrode when in the first position;
a first electromagnet which is operably connected to the body;

a second electromagnet which is operably connected to the body;
a permanent magnet disposed between the first and second electromagnets and operably connected to the heat shroud;
wherein the first electromagnet and the permanent magnet magnetically interact to releasably maintain the heat shroud in the first position;
wherein the second electromagnet and the permanent magnet magnetically interact to releasably maintain the heat shroud in the second position;
wherein the permanent magnet is configured to shift between the first electromagnet and the second electromagnet in response to an electrical current being applied to the first electromagnet, the second electromagnet or both the first electromagnet and the second electromagnet;
wherein the first electromagnet is free of the electrical current when the permanent magnet and the first electromagnet magnetically interact to releasably maintain the heat shroud in the first position;
wherein the second electromagnet is free of the electrical current when the permanent magnet and the second electromagnet magnetically interact to releasably maintain the heat shroud in the second position; and
a multi-function control actuator coupled to the body, wherein actuating the multi-function control actuator to a first configuration translates the heat shroud from the first position to the second position, wherein actuating the multi-function control actuator to a second configuration energizes the non-movable monopolar electrocautery electrode, and wherein releasing the multi-function control actuator translates the heat shroud from the second position to the first position.

2. The electrocautery pencil of claim 1, wherein the first electromagnet includes a first core of magnetic material surrounded by a first coil through which an electric current is passed to magnetize the first core, wherein the first core and first coil are positionally fixed relative to one another.

3. The electrocautery pencil of claim 2, wherein the second electromagnet includes a second core of magnetic material surrounded by a second coil through which an electric current is passed to magnetize the second core, wherein the second core and second coil are positionally fixed relative to one another.

4. The electrocautery pencil of claim 1, further comprising an electrical component coupled to the first electromagnet and the second electromagnet;
wherein the electrical component is configured to permit an electrical current to flow to the first electromagnet, the second electromagnet or both the first electromagnet and the second electromagnet for a momentary time period;
wherein the electrical current is configured to energize the first electromagnet, the second electromagnet or both the first electromagnet and the second electromagnet during the momentary time period;
wherein energizing the first electromagnet, the second electromagnet or both the first electromagnet and the second electromagnet shifts the permanent magnet between the first electromagnet and the second electromagnet.

5. The electrocautery pencil of claim 4, wherein shifting the permanent magnet between the first electromagnet and the second electromagnet shifts the heat shroud between the first position and the second position.

6. The electrocautery pencil of claim 4, wherein the electrical component is a circuit board.

7. The electrocautery pencil of claim 1, wherein the multi-function control actuator includes a first multi-stage actuation button and a second multi-stage actuation button.

8. The electrocautery pencil of claim 7, wherein the first multi-stage actuation button is configured to actuate between a first depressed position and a second depressed position different from the first depressed position, and wherein actuating the first multi-stage actuation button to the first depressed position is configured to translate the heat shroud from the first position to the second position, wherein actuating the first multi-stage actuation button to the second depressed position is configured to energize the non-movable monopolar electrocautery electrode, and wherein releasing the first multi-stage actuation button translates the heat shroud from the second position to the first position.

9. The electrocautery pencil of claim 1, wherein the multi-function control actuator includes a first button, a second button and an actuation button, and wherein the actuation button is positioned between the first button and the second button.

10. The electrocautery pencil of claim 1, wherein releasing the multi-function control actuator stops energizing the non-movable monopolar electrocautery electrode.

11. The electrocautery pencil of claim 1, wherein energizing the non-movable monopolar electrocautery electrode is prevented unless the multi-function control actuator is actuated to translate the heat shroud from the first position to the second position.

12. An electrocautery pencil comprising:

a body;

a non-movable monopolar electrocautery electrode secured to the body, the non-movable monopolar electrocautery electrode including a distal tip;

a heat shroud defining an internal lumen and a distal end, the heat shroud being translatable relative to the non-moveable monopolar electrocautery electrode between a first position wherein the distal tip of the non-movable monopolar electrocautery electrode is disposed entirely within the internal lumen and proximal to the distal end of the heat shroud, and a second position wherein the distal tip of the non-moveable monopolar electrocautery electrode is disposed distal to the distal end of the heat shroud, and wherein the heat shroud is constructed of a heat-resistant material configured to shield the distal tip of the non-movable monopolar electrocautery electrode when in the first position;

an electromagnet operably connected to one of the body and the heat shroud, the electromagnet including a core of magnetic material surrounded by a coil of wire through which an electric current is passed to magnetize the core, a permanent magnet operably connected to the other one of the body and the heat shroud, wherein the electromagnet is configured such that when electrical current is passed through the coil to thereby magnetize the core, the electromagnet magnetically interacts with the permanent magnet to selectively translate the heat shroud from the first position to the second position; and a multi-function control actuator coupled to the body, wherein actuating the multi-function control actuator to a first configuration translates the heat shroud from the first position to the second position, wherein actuating the multi-function control actuator to a second configuration energizes the non-movable monopolar electrocautery electrode, and wherein releasing the multi-function control actuator translates the heat shroud from the second position to the first position.

13. The electrocautery pencil of claim 12, wherein the heat shroud further includes a plurality of cooling apertures extending through a wall of the heat shroud, wherein each of the plurality of cooling apertures provide for fluid communication from an outer surface of the heat shroud to the internal lumen.

14. The electrocautery pencil of claim 13, wherein the electromagnet is configured to magnetically push the permanent magnet to translate the heat shroud from the first position to the second position.

15. The electrocautery pencil of claim 13, wherein the electromagnet is configured to magnetically pull the permanent magnet to translate the heat shroud from the first position to the second position.

16. The electrocautery pencil of claim 13, wherein the plurality of cooling apertures includes a first set of cooling apertures positioned along a first region of the heat shroud and a second set of cooling apertures positioned along a second region of the heat shroud, wherein the first set of cooling apertures are positioned distal to the second set of cooling apertures, wherein the first set of cooling apertures are radially offset from the second set of cooling apertures, wherein the first set of cooling apertures are positioned outside of the body in the second position, and wherein the second set of cooling apertures are positioned within the body in the second position.

* * * * *